US012180516B2

(12) United States Patent
Bowie et al.

(10) Patent No.: US 12,180,516 B2
(45) Date of Patent: *Dec. 31, 2024

(54) BIOSYNTHETIC PLATFORM FOR THE PRODUCTION OF CANNABINOIDS AND OTHER PRENYLATED COMPOUNDS

(71) Applicant: The Regents of the University of California, Oakland, CA (US)

(72) Inventors: James U. Bowie, Los Angeles, CA (US); Meaghan Valliere, Leominster, MA (US); Tyler P. Korman, Sierra Madre, CA (US); Nicholas Woodall, Knoxville, TN (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,221

(22) Filed: Oct. 24, 2022

(65) Prior Publication Data

US 2023/0193221 A1 Jun. 22, 2023

Related U.S. Application Data

(63) Continuation of application No. 17/264,758, filed as application No. PCT/US2019/044752 on Aug. 1, 2019, now Pat. No. 11,479,760.

(Continued)

(51) Int. Cl.
*C12N 9/10* (2006.01)
*C12P 7/22* (2006.01)
(Continued)

(52) U.S. Cl.
CPC .............. *C12N 9/1085* (2013.01); *C12P 7/22* (2013.01); *C12P 7/42* (2013.01); *C12P 9/00* (2013.01);

(Continued)

(58) Field of Classification Search
CPC .. C12N 9/1085; C12N 9/0008; C12N 9/1029; C12N 15/81; C12P 7/22; C12P 7/42;
(Continued)

(56) References Cited

U.S. PATENT DOCUMENTS

| 11,479,760 B2 * | 10/2022 | Bowie .................. C12N 9/1085 |
| 2010/0285502 A1 | 11/2010 | Kuzuyama et al. |
| 2021/0309975 A1 | 10/2021 | Bowie et al. |

FOREIGN PATENT DOCUMENTS

| CN | 113355300 A | 9/2021 |
| DE | 102010011601 A1 | 9/2011 |

(Continued)

OTHER PUBLICATIONS

Muntendam, R. Metabolomics and bioanalysis of terpenoid derived secondary metabolites: Analysis of *Cannabis sativa* L. metabolite production and prenylases for cannabinoid production. 2015. University of Groningen. p. 72, 111-113. (Year: 2015).*

(Continued)

*Primary Examiner* — Soren Harward
*Assistant Examiner* — Naghmeh Nina Moazzami
(74) *Attorney, Agent, or Firm* — Gavrilovich, Dodd & Lindsey LLP

(57) ABSTRACT

Provided is an enzyme useful for prenylation and recombinant pathways for the production of cannabinoids, cannabinoid precursors and other prenylated chemicals in a cell free system as well and recombinant microorganisms that catalyze the reactions.

15 Claims, 13 Drawing Sheets

Specification includes a Sequence Listing.

Related U.S. Application Data

(60) Provisional application No. 62/713,348, filed on Aug. 1, 2018.

(51) Int. Cl.
    *C12P 7/42*           (2006.01)
    *C12P 9/00*           (2006.01)
    *C12P 17/06*         (2006.01)

(52) U.S. Cl.
    CPC ....... *C12P 17/06* (2013.01); *C12Y 102/03003* (2013.01); *C12Y 205/01039* (2013.01)

(58) Field of Classification Search
    CPC .... C12P 9/00; C12P 17/06; C12Y 205/01039; C12Y 102/03003; C12Y 203/01008
    See application file for complete search history.

(56) References Cited

FOREIGN PATENT DOCUMENTS

| | | | | |
|---|---|---|---|---|
| JP | 2008-528036 A | 7/2008 | | |
| JP | 2018-519844 A | 8/2021 | | |
| WO | WO-2004009528 A1 * | 1/2004 | ............ | C07C 65/21 |
| WO | WO-2006081537 A2 * | 8/2006 | ........... | C12N 9/1085 |
| WO | WO-2017015429 A2 * | 1/2017 | ................ | C12P 7/16 |
| WO | 2018/200888 A1 | 11/2018 | | |
| WO | 2019/173770 A1 | 9/2019 | | |
| WO | 2019/183152 A1 | 9/2019 | | |
| WO | 2020/210810 A1 | 10/2020 | | |

OTHER PUBLICATIONS

Seffernick et al.,Melamine Deaminase and Atrazine Chlorohydrolase: 98 Percent Identical but Functionally Different, 2001. J. Bacteriol. 183(8):2405-2410. (Year: 2001).*

Witkowski et al.,Conversion of a â-Ketoacyl Synthase to a Malonyl Decarboxylase by Replacement of the Active-Site Cysteine with Glutamine, 1999. Biochemistry. 38:11643-11650. (Year: 1999).*

Harada et al.,Efficient synthesis of functional isoprenoids from acetoacetate through metabolic pathway-engineered *Escherichia coli,* 2009. Appl Microbiol Biotechnol 81:915-925 (Year: 2009).*

Carvalho et al., Designing microorganisms for heterologous biosynthesis of cannabinoids. 2017. FEMS Yeast Research, 17. (Year: 2017).*

National Center for Biotechnology Information (2023). PubChem Compound Summary for CID 5793, D-Glucose. Retrieved Oct. 19, 2023 from https://pubchem.ncbi.nlm.nih.gov/compound/D-Glucose. (Year: 2023).*

National Center for Biotechnology Information (2023). PubChem Compound Summary for CID 445995, Geranyl diphosphate. Retrieved Oct. 19, 2023 from https://pubchem.ncbi.nlm.nih.gov/compound/Geranyl-diphosphate. (Year: 2023).*

National Center for Biotechnology Information (2023). PubChem Compound Summary for CID 2826719, Olivetolic acid. Retrieved Oct. 19, 2023 from https://pubchem.ncbi.nlm.nih.gov/compound/Olivetolic-acid. (Year: 2023).*

Bridgmohan C, Wang L. DFT studies of proton transfer of 2, 4-dihydroxybenzoic acid derivatives. 2023. ChemRxiv. Cambridge: Cambridge Open Engage. 1-25. (Year: 2023).*

Jadrijević-Mladar Takac M, Vikić Topić D. FT-IR and NMR spectroscopic studies of salicylic acid derivatives. II. Comparison of 2-hydroxy- and 2,4- and 2,5-dihydroxy derivatives. Sep. 2004. Acta Pharm.54(3):177-91. PMID: 15610615. (Year: 2004).*

Booth, J. (2020). Terpene and isoprenoid biosynthesis in *Cannabis sativa* (T). University of British Columbia. Retrieved from https://open.library.ubc.ca/collections/ubctheses/24/items/1.0394478 (Year: 2020).*

Jonson et al., A critical view on conservative mutations, 2001, Protein Engin. Design & Sel., vol. 14, Iss 6, p. 397-402. (Year: 2001).*

International Search Report and Written Opinion, PCT/US2019/044752, United States Patent & Trademark Office, Jan. 9, 2020.

Muntendam, Remco, "Metabolomics and bioanalysis of terpenoid derived secondary metabolites: Analysis of *Cannabis sativa* L. metabolite production and prenylases for cannabinoid production", Jan. 1, 2015.

Nakamura, Yukari, International Preliminary Report on Patentability and Written Opinion, PCT/US2019/044752, The International Bureau of WIPO, Feb. 11, 2021.

Schonwasser, D., Partial Supplementary European Search Report, European Patent Office, Application No. 19843397.1, Apr. 11, 2022.

Schonwasser, D., Partial Supplementary European Search Report, European Patent Office, Application No. 19843397.1, Jun. 27, 2022.

Valliere et al., "A cell-free platform for the prenylation of natural products and application to cannabinoid production," Nature Communicatons, vol. 10, p. 565, Feb. 4, 2019.

Valliere et al., "A bio-inspired cell-free system for cannabinoid production from inexpensive inputs", Nature Chemical Biology, Aug. 24, 2020, vol. 16, No. 12, pp. 1427-1433.

Yang et al., "Catalytic Mechanism of Aromatic Prenylation by NphB," Biochemistry, 51(12):2606-2618, 2012.

Zirpel et al., "Engineering yeasts as platform organisms for cannabinoid biosynthesis", Journal of Biotechnology, Jul. 8, 2017, vol. 259, pp. 204-212.

Zocher et al., "Structure-Based Engineering Increased the Catalytic Turnover Rate of a Novel Phenazine Prenyltransferase," PLoS ONE, 7(10):e48427, 2012.

Fukuma, Nobuko, Office Action, Japan Patent Office, Application No. 2021-504498, Jul. 25, 2023.

* cited by examiner

BIOSYNTHETIC PLATFORM FOR THE PRODUCTION OF CANNABINOIDS AND OTHER PRENYLATED COMPOUNDS

CROSS REFERENCE TO RELATED APPLICATIONS

This application is a continuation of U.S. application Ser. No. 17/264,758, filed Jan. 29, 2021, which application claims priority under 35 U.S.C. § 371 to International Application No. PCT/US2019/044752, filed Aug. 1, 2019, which application claims priority to U.S. Provisional Application Ser. No. 62/713,348, filed Aug. 1, 2018, the disclosures of which are incorporated herein by reference in their entirety

STATEMENT REGARDING FEDERALLY SPONSORED RESEARCH

This invention was made with government support under Grant Number DE-FC02-02ER63421, awarded by the U.S. Department of Energy, and Grant Number GM008496, awarded by the National Institutes of Health. The government has certain rights in the invention.

SEQUENCE LISTING

The instant application contains a Sequence Listing which has been submitted electronically in .xml format and is hereby incorporated by reference in its entirety. Said XML copy, created on Oct. 24, 2022, is named 00011-089US2.xml and is 118,602 bytes in size.

TECHNICAL FIELD

Provided are methods of producing cannabinoids and other prenylated chemicals and compounds by contacting a suitable substrate with a metabolically-modified microorganism or enzymatic preparations of the disclosure.

BACKGROUND

Prenylation of natural compounds adds structural diversity, alters biological activity, and enhances therapeutic potential. Prenylated compounds often have low natural abundance or are difficult to isolate. Some prenylated natural products include a large class of bioactive molecules with demonstrated medicinal properties. Examples include prenyl-flavanoids, prenyl-stilbenoids, and cannabinoids Cannabinoids are a large class of bioactive plant derived natural products that regulate the cannabinoid receptors (CB1 and CB2) of the human endocannabinoid system. Cannabinoids are promising pharmacological agents with over 100 ongoing clinical trials investigating their therapeutic benefits as antiemetics, anticonvulsants, analgesics and antidepressants. Further, three cannabinoid therapies have been FDA approved to treat chemotherapy induced nausea, MS spasticity and seizures associated with severe epilepsy.

Despite their therapeutic potential, the production of pharmaceutical grade (>99%) cannabinoids still face major technical challenges. Cannabis plants like marijuana and hemp produce high levels of tetrahydrocannabinolic (THCA) and cannibidiolic acid (CBDA), along with a variety of lower abundance cannabinoids. However, even highly expressed cannabinoids like CBDA and THCA, are challenging to isolate due to the high structural similarity of contaminating cannabinoids and the variability of cannabinoid composition with each crop. These problems are magnified when attempting to isolate rare cannabinoids. Moreover, current cannabis farming practices present serious environmental challenges. Consequently, there is considerable interest in developing alternative methods for the production of cannabinoids and cannabinoid analogs.

SUMMARY

The disclosure provides a recombinant polypeptide comprising a sequence selected from the group consisting of: (a) SEQ ID NO:30 and having at least a Y288X mutation, wherein X is A, N, S, V or a non-natural amino acid; (b) SEQ ID NO: 30 having at least a Y288X mutation, wherein X is A, N, S, V or a non-natural amino acid and at least one other mutation selected from V49$Z_1$, F213$Z_2$, A232S, I234T, V271$Z_3$ and/or G286S, wherein $Z_1$ S, N, T or G, $Z_2$ is H, N or G and $Z_3$ is N or H; (c) any of the mutations combination set forth in Table 1; (d) any of (a), (b) or (c) comprising from 1-20 conservative amino acid substitutions and having NphB prenyltransferase activity; (e) a sequence that is at least 85%, 90%, 95%, 98% or 99% identical to SEQ ID NO:30 and which has at least the mutations recited in (a), (b) or (c); (f) a sequence recited in SEQ ID NOs: 1-28 or 29 beginning at amino acid 21; and (g) any sequence that is at least 99% identical to any of SEQ ID NOs: 1-28 or 29, wherein the polypeptide of any of (a)-(g) perform prenylation reactions. In one embodiment, the prenylation reaction comprises the production of cannabigerolic acid (CBGA) from geranyl pyrophosphate (GPP) and Olivetolate or cannabigerovarinic acid (CBGVA) from GPP and divarinic acid or CBGXA from a 2,4-dihydroxy benzoic acid or derivative thereof with a chemical group at the C6 position (see, e.g., Formula I).

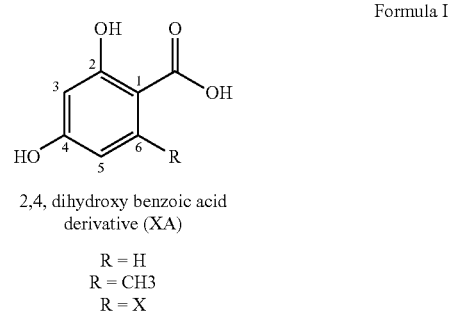

Formula I 2,4, dihydroxy benzoic acid derivative (XA)

R = H
R = CH3
R = X

Where 'X' can be a halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted ($C_1$-$C_{10}$)alkyl, an optionally substituted ($C_2$-$C_{10}$)alkenyl, an optionally substituted ($C_2$-$C_{10}$)alkynyl, an optionally substituted ($C_1$-$C_{10}$)hetero-alkyl, an optionally substituted ($C_2$-$C_{10}$) hetero-alkenyl, an optionally substituted ($C_2$-$C_{10}$)hetero-alkynyl, an optionally substituted ($C_3$-$C_{10}$)cycloalkyl, an optionally substituted aryl, and an optionally substituted heterocycle. In one embodiment, X is a substituted or unsubstituted alkyl containing 2 to 10 carbons.

The disclosure also provides a recombinant pathway comprising a polypeptide having a sequence a sequence selected from the group consisting of: (a) SEQ ID NO:30 and having at least a Y288X mutation, wherein X is A, N, S, V or a non-natural amino acid; (b) SEQ ID NO:30 having at least a Y288X mutation, wherein X is A, N, S, V, or a non-natural amino acid and at least one other mutation selected from V49$Z_1$, F213$Z_2$, A232S, I234T, V271$Z_3$ and/or G286S, wherein $Z_1$ S, N, T or G, $Z_2$ is H, N or G and $Z_3$ is N or H; (c) any of the mutations combination set forth in Table 1; (d) any of (i), (ii) or (iii) comprising from 1-20 conservative amino acid substitutions and having NphB activity; (e) a sequence that is at least 85%, 90%, 95%, 98% or 99% identical to SEQ ID NO:30 and which has at least the mutations recited in (i), (ii) or (iii); (f) a sequence recited in SEQ ID NOs:1-28 or 29 beginning at amino acid 21; (g) any sequence that is at least 99% identical to any of SEQ ID NOs: 1-28 or 29, and a plurality of enzymes that convert glucose to Geranylpyrophosphate; and (h) any sequence that is at least 99% identical to any of SEQ ID NOs:1-28 or 29 and a plurality of enzymes that convert (iso)prenol to geranylpyrophosphate. In another embodiment, the method further comprises a pyruvate dehydrogenase bypass enzymatic pathway comprising a pyruvate oxidase and an acetyl phosphate transferase. In another or further embodiment, the pathway comprises a "purge valve" that recycles NADH/NAD and NADPH/NADP. In another or further embodiment of any of the foregoing, the pathway comprises the following enzymes: (i) hexokinase (Hex); (ii) Glucose-6-phosphate isomerase (Pgi); (iii) Phosphofructokinase (Pfk); (iv) Fructose-1,6-bisphosphate aldolase (Fba); (v) Triose phosphate isomerase (Tpi); (vi) Gald-3-P dehydrogenase (Gap); (vii) a mutant Gald-3-P dehydrogenase (mGap); (viii) NADH Oxidase (Nox); (ix) Phosphoglycerate Kinase (Pgk); (x) Phosphoglycerate Mutase (2,3 BPG dependent) (dPgm); (xi) Enolase (eno); (xii) Pyruvate Kinase (FBP dependent); (xiii) Pyruvate Oxidase (PyOx); (xiv) Acetyl-phosphate transferase (PTA); (xv) Acetyl-CoA acetyltransferase (PhaA); (xvi) HMG-CoA Synthase (HMGS); (xvii) HMG-CoA Reductase (HMGR); (xviii) Mevalonate Kinase (MVK); (xix) Phosphomevalonate Kinase (PMVK); (xx) Diphosphomevalonate decarboxylase (MDC); (xxi) isopentenyl diphosphate isomerase (IDI); (xxii) geranyl-PP synthase (GPPS); and; (xxiii) a mutant aromatic prenyltransferase. In yet a further embodiment of any of the foregoing embodiments, the pathway comprises the enzymes (i) to (xviii) and (xxii) to (xxiii) above in addition to phosphomevalonate decarboxylase (PMDC) and isopentenyl-phosphate kinase (IPK). In yet another or further embodiment, the pathway comprises a 4-step pathway to convert isoprenol or prenol to GPP using ATP and one or more steps to recycle ADP/ATP. In another or further embodiment of any of the foregoing, the pathway comprises (a) (iso)prenol kinase (PRK); (b) isopentenyl phosphate kinase (IPK); (c) isopentenyl diphosphate isomerase (IDI); and (d) geranyl pyrophosphate synthase (GPPS). In still another or further embodiment, the pathway is supplemented with ATP and olivetolate (or 2,4-dihydroxy benzoic acid or derivative thereof) and the pathway produces a cannabinoid precursor. In a further embodiment, the pathway further comprises a cannabidiolic acid synthase. In still another or further embodiment, the pathway produces cannabidiolic acid.

The disclosure also provides a method of producing a prenylated compound comprising contacting a substrate with a prenyl-group having the general structure:

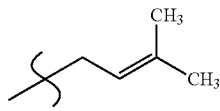

in the presence of a recombinant polypeptide having a sequence selected from the group consisting of: (a) SEQ ID NO:30 and having at least a Y288X mutation, wherein X is A, N, S, V or a non-natural amino acid; (b) SEQ ID NO:30 having at least a Y288X mutation, wherein X is A, N, S, V or a non-natural amino acid, and at least one other mutation selected from V49$Z_1$, F213$Z_2$, A232S, I234T, V271$Z_3$ and/or G286S, wherein $Z_1$ S, N, T or G, $Z_2$ is H, N or G and $Z_3$ is N or H; (c) any of the mutations combination set forth in Table 1; (d) any of (i), (ii) or (iii) comprising from 1-20 conservative amino acid substitutions and having NphB activity; (e) a sequence that is at least 85%, 90%, 95%, 98% or 99% identical to SEQ ID NO:30 and which has at least the mutations recited in (i), (ii) or (iii); (f) a sequence recited in SEQ ID NOs:1-28 or 29 beginning at amino acid 21; and (g) any sequence that is at least 99% identical to any of SEQ ID NOs: 1-28 or 29, wherein the prenyl group is added to the substrate.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

Figure 1A:
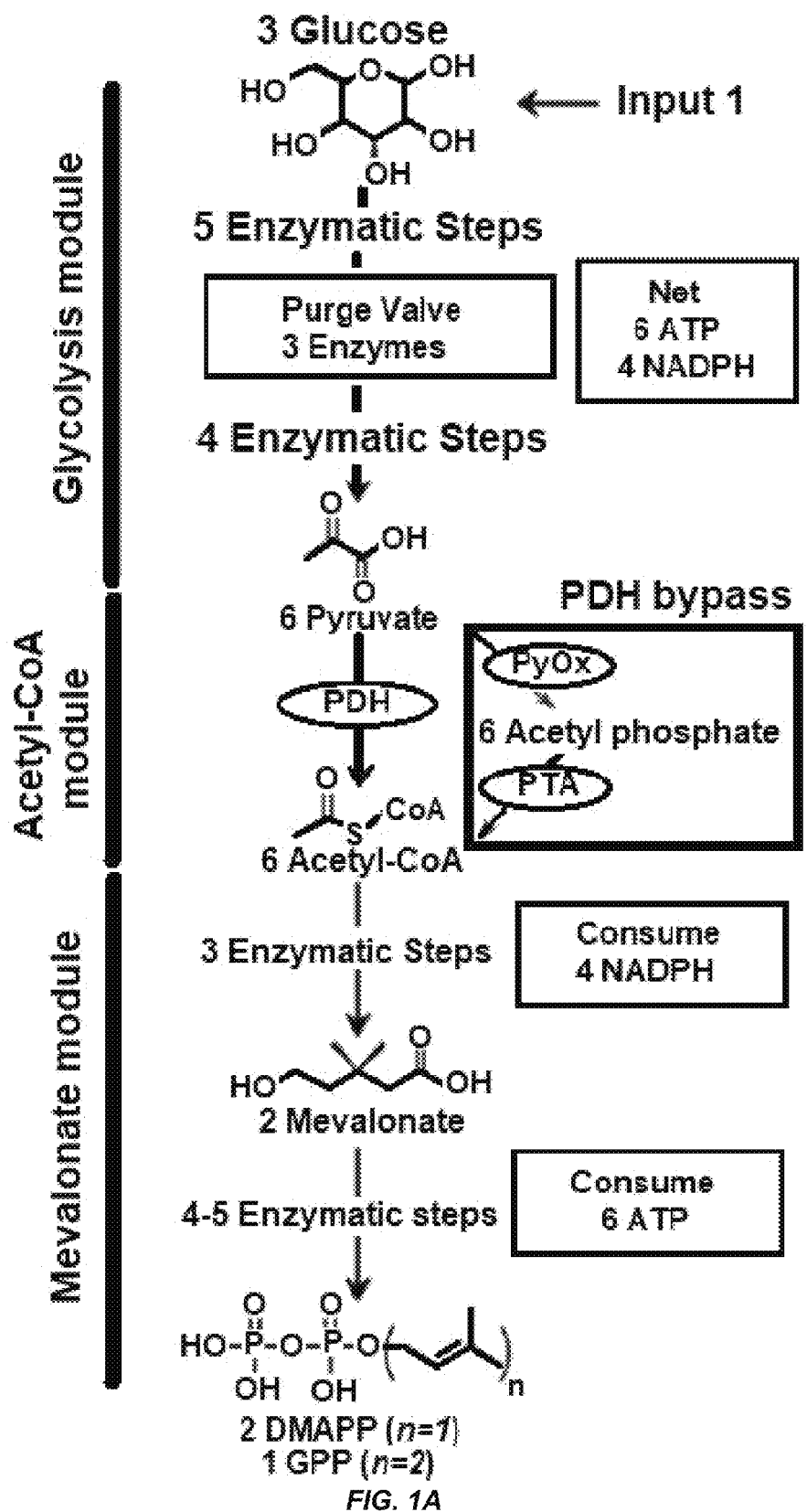
FIG. 1A-B depicts exemplary biosynthetic pathways of the disclosure. (A) The synthetic biochemistry platform for the production of prenylnatural products. First, glucose is broken down into pyruvate through a glycolysis pathway modified to regulate NADPH levels (12 enzymatic steps). Then, either PDH or the PDH bypass converts pyruvate into acetyl-CoA. Acetyl-CoA is converted into GPP via the mevalonate pathway (eight enzymatic steps). By varying the aromatic prenyltransferase (aPT) and aromatic substrate various prenyl-flavonoids and prenyl-stilbenoids using the same central pathway can be produced. Variants of the prenyltransferase NphB (dNphB) were developed to produce CBGA or CBGVA. CBGA is converted to cannabidiolic acid (CBDA) and CBGVA is converted to cannabidivaric acid (CBDVA) via cannabidiolic acid synthase (CBDAS). It is possible to produce other cannabinoids by using different cannabinoid synthases (THCAS and CBCAS). (B) Depicts a more detailed view of the pathway of (A). Glucose is broken down into pyruvate through glycolysis (dark blue). The purge valve outlined in dark blue allows carbon flux to continue through the glycolysis pathway without building up excess NADPH. Pyruvate is converted to acetyl-CoA through the PDH bypass outlined in light blue. Acetyl-CoA is built up into high energy phosphate molecules through the mevalonate pathway (aqua) to produce GPP. Then, the GPP from the mevalonate pathway is used to prenylate an aromatic polyketide. Shown here is the prenylation of olivetolate to produce CBGA; however, olivetolate could be replaced with a wide range of substrates (aromatic and non-aromatic) to generate various prenylated products. Finally, CBGA is converted to CBDA with CBDAS. A spontaneous decarboxylation completes the biosynthetic pathway to CBDA. The production of CBDA completes the cannabinoid module shown in green.

As used herein and in the appended claims, the singular forms "a," "an," and "the" include plural referents unless the context clearly dictates otherwise. Thus, for example, reference to "a polynucleotide" includes a plurality of such polynucleotides and reference to "the enzyme" includes reference to one or more enzymes, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

Prenylation (also known as isoprenylation or lipidation) is the addition of hydrophobic molecules to a protein or chemical compound. It is usually assumed that prenyl groups (3-methylbut-2-en-1-yl) facilitate attachment to cell membranes, similar to lipid anchors like the GPI anchor. Prenyl groups have been shown to be important for protein-protein binding through specialized prenyl-binding domains.

Prenylated natural products are a large class of bioactive molecules with demonstrated medicinal properties. Examples include prenyl-flavanoids, prenyl-stilbenoids, and cannabinoids. Plant-derived prenylcompounds are difficult to isolate due to the structural similarity of contaminating molecules, and the variable composition between crops. These challenges are further exacerbated when attempting to isolate low abundance compounds. Many chemical syntheses have been developed to address the challenges associated with making prenylated natural products, but they are generally impractical for drug manufacturing due to the degree of complexity and low yields.

Microbial production is a useful alternative to natural extraction for prenylated natural products, but comes with many challenges such as the need to divert carbon flux from central metabolism and product toxicity to name a few. For example, prenyl-natural products like prenyl-naringenin, prenyl-resveratrol, and cannabidiolic acid (CBDA) are derived from a combination of the metabolic pathways for fatty acid, isoprenoid, and polyketide biosynthesis. So, high-level production requires efficient rerouting of long, essential and highly regulated pathways. Despite the challenges, many groups have engineered microbes to produce unprenylated polyketides, like naringenin, resveratrol, and olivetolate, but at relatively low levels (110, 391, and 80 mg/L, respectively). Obtaining prenylated products is even more challenging because geranyl-pyrophosphate (GPP) is an essential metabolite that is toxic to cells at moderate concentrations, creating a significant barrier for high-level microbial production.

Cannabinoids in particular show immense therapeutic potential with over 100 ongoing clinical trials as antiemetics, anticonvulsants, antidepressants, and analgesics. Nevertheless, despite the therapeutic potential of prenyl-natural products, their study and use is limited by the lack of cost-effective production methods.

The two main alternatives to plant-based cannabinoid production are organic synthesis and production in a metabolically engineered host (e.g., plant, yeast, or bacteria). Total syntheses have been elucidated for the production of some cannabinoids, such as THCA and CBDA, but they are often not practical for drug manufacturing. Additionally, the synthetic approach is not modular, requiring a unique synthesis for each cannabinoid. A modular approach could be achieved by using the natural biosynthetic pathway.

The three major cannabinoids (THCA, CBDA and cannabichromene or CBCA) are derived from a single precursor, CBGA. Additionally, three low abundance cannabinoids are derived from CBGVA (FIG. 1A). Thus, the ability to make CBGA and CBGVA in a heterologous host would open the door to the production of an array of cannabinoids. Unfortunately, engineering microorganisms to produce CBGA and CBGVA has proven extremely challenging.

Cannabinoids are derived from a combination of fatty acid, polyketide, and terpene biosynthetic pathways that generate the key building blocks geranyl pyrophosphate (GPP) and olivetolic acid (OA) (FIG. 1A). High level CBGA biosynthesis requires the re-routing of long, essential and highly regulated pathways. Moreover, GPP is toxic to cells, creating a notable barrier to high level production in microbes. While Gagne et al. (Proc. Natl. Acad. Sci., 109: 12811, 2012) engineered a pathway to produce OA in yeast, the titers were very low (0.5 mg $L^{-1}$), suggesting that high level production of intermediates on the pathway is not straightforward. In a separate study, Zirpel et al. produced THCA in a yeast lysate containing the promiscuous prenyltransferase (NphB) and THCA synthase, supplemented with GPP and olivetolic acid (OA) (J. Biotechnol., 259:204-212, 2017). Yet, there are still no published reports of cannabinoid production in engineered live cells from low cost feedstocks.

Synthetic biochemistry, in which complex biochemical conversions are performed cell-free using a mixture of enzymes, affords potential advantages over traditional metabolic engineering including: a higher level of flexibility in pathway design; greater control over component optimization; more rapid design-build-test cycles; and freedom from cell toxicity of intermediates or products. The disclosure provides a cell-free system for the production of cannabinoids.

This disclosure provides enzyme variants and pathways comprising such variants for the prenylation of compounds including the production of cannabinoids. In addition, the biosynthetic pathways described herein use "purge valves" to regulate NAD(P)H levels. Such "purge valves" have demonstrated high level production of monoterpenes from glucose indicating that significant GPP can be produced cell-free (see, International Pat. Publ. WO2017/015429, the disclosure of which is incorporated herein by reference). These purge valves were used to upgrade and diversify the original system to produce complex natural products like cannabinoids. A synthetic biochemistry approach is outlined in FIGS. 1A, 1B, 5A and 5B. In one embodiment, the disclosure provides a cell-free system for prenylation using GPP derived from glucose (see, FIGS. 1A, 1B, 5A, 5B and 7). In another embodiment, the disclosure provides a cell-free system for prenylation using GPP derived from (iso) prenol or prenol (see, FIG. 6). The pathway of FIG. 6 can be coupled to any ATP generating system to produce the ATP needed for a reaction. For example, the pathway can be coupled with a creatine kinase ATP generating system; an acetate kinase system; a glycolysis system as well as others. Enzymes (nucleic acid coding sequences and polypeptides) of FIG. 6 are provided in SEQ ID NOs: 54-65 (e.g., PRK enzymes are provided in SEQ ID NOs: 54-57; IPK enzymes are provided in SEQ ID NOs: 58-61; IDI enzymes are provided in SEQ ID NOs:62-63; and FPPS enzymes are provided in SEQ ID NOs: 64-65).

NphB is an aromatic prenyltransferase that catalyzes the attachment of a 10-carbon geranyl group to aromatic substrates. NphB exhibits a rich substrate selectivity and product regioselectivity. NphB, identified from *Streptomyces*, catalyzes the addition of a 10-carbon geranyl group to a number of small organic aromatic substrates. NphB has a spacious and solvent accessible binding pocket in to which two substrates molecules, geranyl diphosphate (GPP) and 1,6-dihydroxynaphthalene (1,6-DHN), can be bound. GPP is stabilized via interactions between its negatively charged diphosphate moiety and several amino acid sidechains, including Lys119, Thr171, Arg228, Tyr216 and Lys284, in addition to $Me^{2+}$. A $Mg^{2+}$ cofactor is required for the activity of NphB. NphB from *Streptomyces* has a sequence as set forth in SEQ ID NO:30.

NovQ (accession no. AAF67510, incorporated herein by reference) is a member of the CloQ/NphB class of prenyltransferases. The novQ gene can be cloned from *Streptomyces niveus*, which produces an aminocoumarin antibiotic, novobiocin. Recombinant NovQ can be expressed in *Escherichia coli* and purified to homogeneity. The purified enzyme is a soluble monomeric 40-kDa protein that catalyzed the transfer of a dimethylallyl group to 4-hydroxyphenylpyruvate (4-HPP) independently of divalent cations to yield 3-dimethylallyl-4-HPP, an intermediate of novobiocin. In addition to the prenylation of 4-HPP, NovQ catalyzed carbon-carbon-based and carbon-oxygen-based prenylations of a diverse collection of phenylpropanoids, flavonoids and dihydroxynaphthalenes. Despite its catalytic promiscuity, the NovQ-catalyzed prenylation occurred in a regiospecific manner. NovQ is the first reported prenyltransferase capable of catalyzing the transfer of a dimethylallyl group to both phenylpropanoids, such as p-coumaric acid and caffeic acid, and the B-ring of flavonoids. NovQ can serve as a useful biocatalyst for the synthesis of prenylated phenylpropanoids and prenylated flavonoids.

*Aspergillus terreus* aromatic prenyltransferase (AtaPT; accession no. AMB20850, incorporated herein by reference), which has recently been discovered and characterized, is responsible for the prenylation of various aromatic compounds. Recombinant AtaPT can be overexpressed in *Escherichia coli* and purified. *Aspergillus terreus* aromatic prenyltransferase (AtaPT) catalyzes predominantly C-monoprenylation of acylphloroglucinols in the presence of different prenyl diphosphates.

Figure 2A:
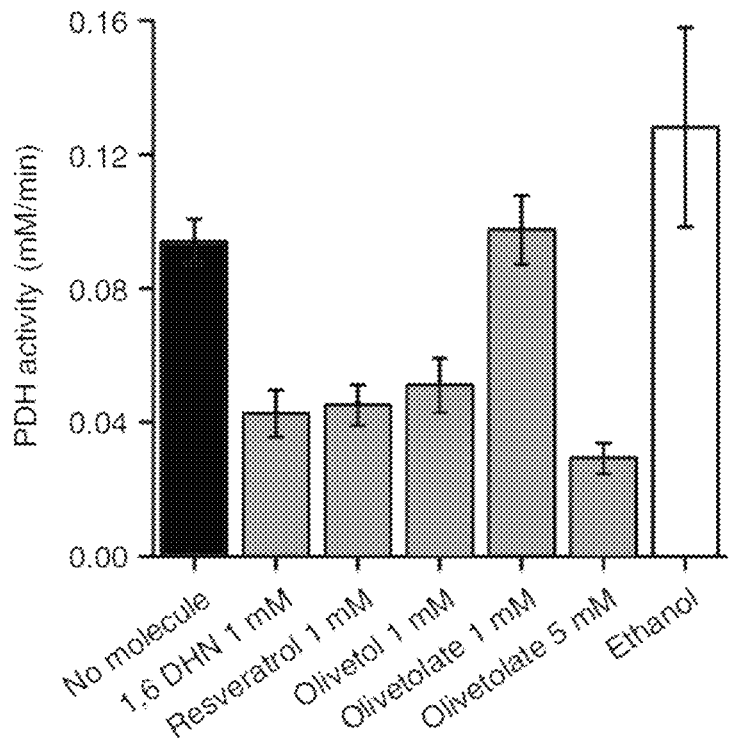
FIG. 2A-D shows development of PDH bypass for the prenylation of aromatic polyketides. (A) The activity of pyruvate dehydrogenase (Ec PDH) was measured in the presence of various aromatic polyketides and 2% ethanol (vehicle) (n=3). (B) A comparison of the final titers achieved with the full pathway utilizing PDH (PDH system—gray trace) and the PDH bypass system (blue trace) at different concentrations of 1,6 DHN. Error bars represent the standard deviation between samples (n=3). (C) The amount of 5-prenyl-1,6-DHN blue trace and CBGA green trace produced over time with the PDH bypass system using WT NphB. The error bars represent the standard deviation between samples (n=3). (D) Various aromatic substrates were added to the pathway with either NphB, AtaPT, or NovQ prenyltransferase (biological replicates, n=3). The result is a variety of C5 and C10 prenyl-natural products. (* Indicates titer not determined).
Figure 2B:
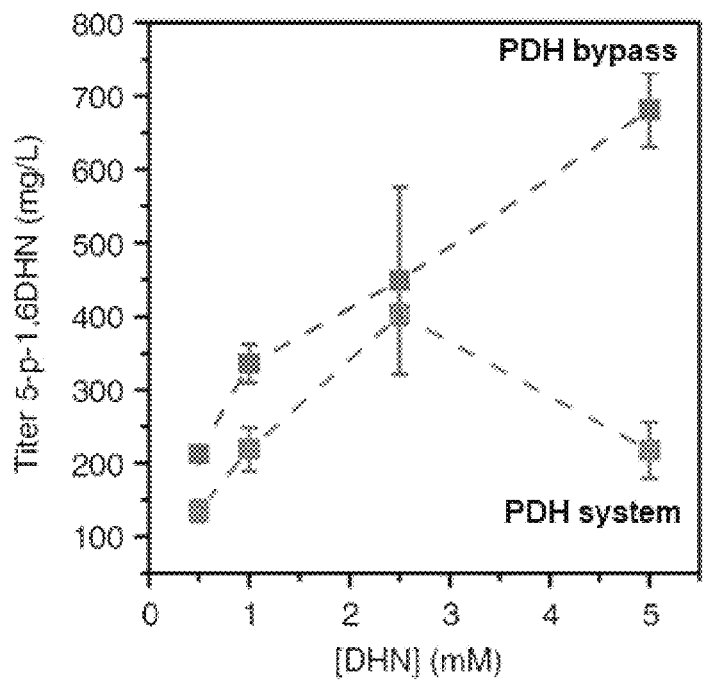
Figure 2C:
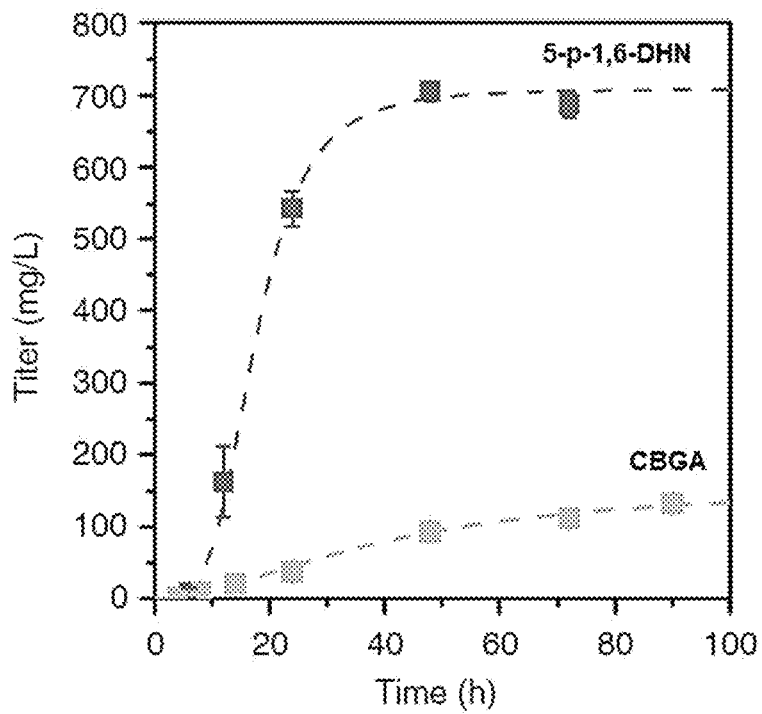
Figure 2D:
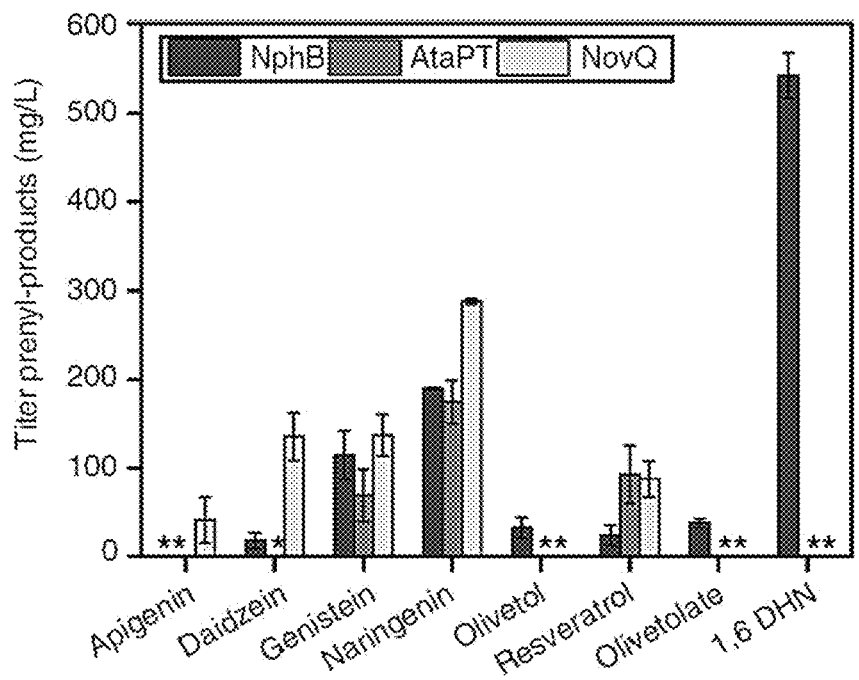

Olivetolic acid (OA) is a relatively poor substrate for wild-type NphB. As a result, the ability of the cell-free system to prenylate a co-substrate was tested by using a more preferred NphB substrate, 1,6 dihydroxynapthalene (1,6 DHN). About 400 mg/L (1.3 mM) of prenylated product was obtained when starting with 2.5 mM 1,6 DHN and 500 mM glucose. However, when the starting 1,6 DHN concentration was increased from 2.5 to 5 mM, final titers decreased 2-fold suggesting that 1,6 DHN was inhibiting one or more enzymes. Enzyme assays revealed that *E. coli* pyruvate dehydrogenase (EcPDH) was inhibited by not only 1,6 DHN, but several other aromatic polyketides (FIG. 2B). At 1 mM of either 1,6 DHN, olivetol, or resveratrol the activity of PDH decreased 2-fold (FIG. 2B). Thus, experiments were designed to eliminate PDH by implementing a PDH bypass (see FIGS. 1A and 2B). In the PDH bypass, pyruvate was converted to acetyl-CoA using pyruvate oxidase (PyOx) and acetyl-phosphate transferase (PTA) thereby eliminating PDH (FIG. 1A). As shown in FIG. 2A the new system removed the inhibition seen at higher concentrations of 1,6 DHN and increased titers of 5-prenyl-1,6 DHN 4-fold over the PDH system when starting at 5 mM 1,6 DHN (FIG. 2B). FIG. 2C shows a time course of 5-prenyl-1,6 DHN biosynthesis starting with 5 mM 1,6 DHN utilizing the PDH bypass. Approximately 50% of the 1,6 DHN was converted in the first 24 hours, ultimately reaching a final titer of 705±12 mg/L.

Figure 3A:
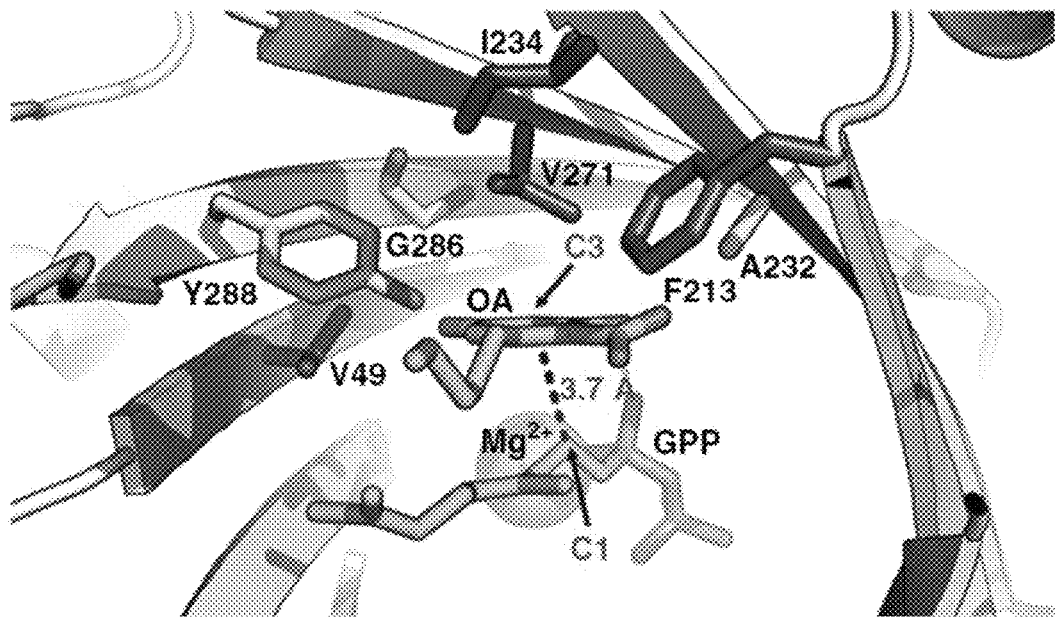
FIG. 3A-C shows the engineering of NphB to improve CBGA production. (A) A model of olivetolate in the active site of WT NphB. Residues A288, G286 and A232 and 1234, V271 and V49 were allowed to vary during the design process. Residues A288, G286 and A232 had the largest effects on activity with OA and were the positions targeted in the focused library. (B) The results of an activity assay to determine the approximate activity of NphB mutants with olivetolate as the substrate. The fold-improvement is an average of triplicate reactions with GPP (2.5 mM) olivetolate (5 mM), $MgCl_2$ (5 mM) and 1 mg/mL of WT NphB and mutants. (C) GC-MS chromatograms of the full pathway reaction products using of M23 and WT NphB compared to a CBGA standard. The M23 mutant dramatically improves specificity for the correct product.

The prenylation of aromatic polyketides by NphB is thought to proceed through a carbocation intermediate in which the first step is dissociation of diphosphate from GPP to create a carbocation on the C1 carbon of GPP, which subsequently attacks a nearby nucleophile. To improve the regiospecificity of prenyl-transfer, OA was modeled into the active site of NphB using the crystal structure of NphB in complex with 1,6 DHN, $Mg^{2+}$ and a nonhydrolyzable analog of GPP (geranyl S-thiolodiphosphate) as a starting point (PDBID 1ZB6; Protein Data Bank reference 1ZB6). For the design, OA was placed into the binding pocket using 1,6 DHN as a guide, situating the desired prenylation site, the C3 carbon of OA, 3.7 Å above the nascent geranyl C1 carbocation (FIG. 3A). The distance chosen was based on the distance of the C5 carbon of 1,6 DHN to the C1 carbon of GPP. Residues in contact with OA were then varied using ROSETTA software to optimize the active site of NphB for binding OA. Side chains in contact with GPP or that potentially provide catalytic function were left fixed. The result was an ensemble of suggested NphB variants.

To reduce the number of variants to test experimentally, changes likely to have the most significant impact on OA binding were ranked using a scoring system. A representative group of variants were picked (Table 1) and each residue was systematically changed back to the wild-type side chain in the background of the other mutations, and the change evaluated in the energy score (Table 2). Y288 replacements had the largest impact on the energy score so Y288A or the Y288N mutation were used in every construct evaluated experimentally. The frequency of mutation, how multiple mutations might work in concert, and the computational energy score to further shape the NphB library were all considered. With these considerations, a library comprised of 29 constructs ranging from a single point mutant to up to 6 mutations per construct was generated as set forth in Table 1 (see also SEQ ID NOs: 1-29; note SEQ ID NOs: 1-29 include a hexahistidine leader from the expression construct, i.e., amino acids 1-20, which are not necessary for biological activity).

TABLE 1 provides exemplary mutations and the fold improvement relative to wild type (i.e., a polypeptide of SEQ ID NO: 30). NphB library constructs and mutations (amino acid positions referenced to SEQ ID NO: 30).

| NphB Construct | Mutations | Fold Improvement over WT |
|---|---|---|
| M1 | Y288A | 26 |
| M2 | Y288N | 11 |
| M3 | Y288A, F213H | 12 |
| M4 | Y288A, F213N | 2 |
| M5 | Y288N, V49S | 5 |
| M6 | Y288S, V49N | 11 |
| M7 | Y288A, V49S | 9 |
| M8 | Y288N, V49T | 1 |
| M9 | Y288N, I234T | 1 |
| M10 | Y288N, G286S | 150 |
| M11 | Y288N, F213N, V49G | 3 |
| M12 | Y288A, F213N, I234T | 3 |
| M13 | Y288S, F213N, V49N | 2 |
| M14 | Y288N, F213G, I234T | 1 |
| M15 | Y288A, F213N, A232S | 17 |
| M16 | Y288N, F213N, A232S | 2 |
| M17 | Y288N, F213G, V49T | 2 |
| M18 | Y288N, V49S, V271N | 1 |
| M19 | Y288N, F213N, V49S, V271N | 2 |
| M20 | Y288N, F213G, V49T, V271H | 4 |
| M21 | Y288N, F213N, V49S, I234T, A232S, V271N | 0.5 |
| M22 | Y288N, F213G, V49T, I234T, V271H, L298I | 0.5 |
| M23* | Y288A, G286S | 185 |
| M24* | Y288A, G286S, A232S | 150 |
| M25* | Y288A, G286S, A232S, F213H | 110 |
| M27* | Y288V, G286S | 155 |
| M28* | Y288V, G286S, A232S | 1.5 |
| M30* | Y288A, A232S | 175 |
| M31* | Y288V, A232S | 180 |
| M32[b] | V49I | ND |
| M33[b] | M162C | ND |
| M34[b] | M162R | ND |
| M35[b] | A232N | ND |
| M36[b] | V271S | ND |
| M37[b] | V271A | ND |
| M38[b] | Y288D | ND |
| M39[b] | Y288H | ND |
| M40[b] | L298R | ND |
| M41[b] | L298A | ND |
| M42[b] | L298G | ND |
| M43[b] | L298V | ND |
| M44[b] | L298N | ND |

*Second round focused library
[b]Mutation predicted by Rosetta, but not tested
ND—Not determined

TABLE 2

Kinetic parameters for NphB mutants

| Construct | $k_{cat}$ (min$^{-1}$) | $K_M$ (mM) | $k_{cat}/K_M$ (min$^{-1}$ mM$^{-1}$) |
|---|---|---|---|
| WT NphB | 0.0021 ± 0.00008 | 0.64 ± 0.08 | 0.0033 ± 0.0005 |
|  | 0.0047 ± 0.0003 [b] | 0.88 ± 0.2 [b] | 0.005 ± 0.001 [b] |
| NphB M1 | 0.061 ± 0.003 | 0.58 ± 0.11 | 0.11 ± 0.02 |
| NphB M10 | 0.79 ± 0.02 | 0.34 ± 0.02 | 2.4 ± 0.2 |
| NphB M23 | 1.58 ± 0.05 | 0.45 ± 0.05 | 3.5 ± 0.4 |
|  | 0.48 ± 0.07 [b] | 2.4 ± 0.6 [b] | 0.2 ± 0.06 [b] |
| NphB M30 | 1.07 ± 0.05 | 0.25 ± 0.05 | 4.2 ± 0.9 |
| NphB M31 | 1.30 ± 0.05 | 0.12 ± 0.02* | 10.8 ± 2.1 |
|  | 6.0 ± 0.8 [b] | 1.8 ± 0.5 [b] | 3.3 ± 1 [b] |

[b] Kinetic parameters for divarinic acid

Recombinant methods for producing and isolating modified NphB polypeptides of the disclosure are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154;

each of which is incorporated by reference). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

Figure 3B:
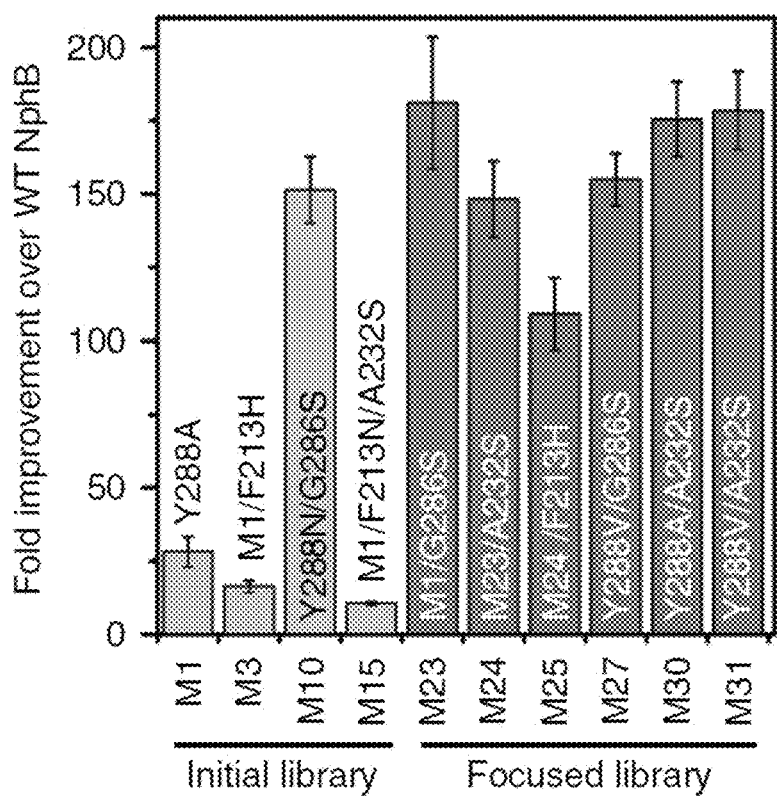

Crudely purified NphB mutants were obtained and an initial screen was performed for CBGA production using GPP and OA at concentrations that were saturating for wild-type NphB. Six constructs were identified that had >10-fold apparent increase in activity (M1, M2, M3, M6, M10 and M15) and 4 constructs that had 2-10-fold apparent improvement (M5, M7, M12 and M20) when compared to WT NphB, while the remaining constructs had similar activity to WT NphB. The top hits from the initial screen (M1, M3, M10 and M15) were purified and more carefully characterized (FIG. 3B). Several observations were apparent from the initial screen: (1) Y288A (M1) and Y288N (M2) by themselves dramatically enhanced activity, as predicted by computation; (2) the presence of Y288N in any construct decreased the purification yield suggesting Y288N may be a destabilizing mutation making Y288A a more desirable mutation; (3) the addition of G286S in the Y288N (M10) background appeared to improve activity further over Y288N (M2), suggesting that G286S could be another favorable mutation; (4) a slight activity improvement of Y288A/F213N/A232S (M15) over Y288A (M1), even though F213N had a neutral or deleterious effect in the Y288A/F213N (M5) construct suggesting that A232S may also be a favorable mutation.

From these initial observations a focused library was designed that included variants Y288A, GS86S and A232S in various combinations. Other combinations with Y288V were added with the rationale that it may improve stability while still reducing the size of the Y288 side chain. All but one of the constructs in the second library exhibited activity at least 100-fold higher than WT NphB in a one hour endpoint assay. A comparison of the best mutants from round one and the best mutants from round two are shown in FIG. 3B. Clearly, the combination of beneficial mutations from round 1 improved CBGA production. Additionally the Y288A and Y288V constructs improved expression of NphB compared to Y288N without sacrificing activity.

The best two mutants from the initial screen were further characterized as well as the best three constructs from the focused library. The kinetic parameters are summarized in Table 2. While all of the mutants have relatively modest effects on $K_m$, a dramatic improvements in $k_{cat}$ values was observed. M23 (the NphB of SEQ ID NO:23) in particular improved $k_{cat}$ 750-fold from $0.0021\pm0.00008$ min$^{-1}$ to $1.58\pm0.05$ min$^{-1}$. The catalytic efficiency ($k_{cat}/K_m$) for both M23 and M31 were improved over 1000-fold compared to the wild-type enzyme. Although M31 had a higher $k_{cat}/K_m$ than M23, M23 was employed rather than M31 because M23 had a higher $k_{cat}$ and the synthetic biochemistry system generally operates at saturating OA conditions.

Figure 3C:
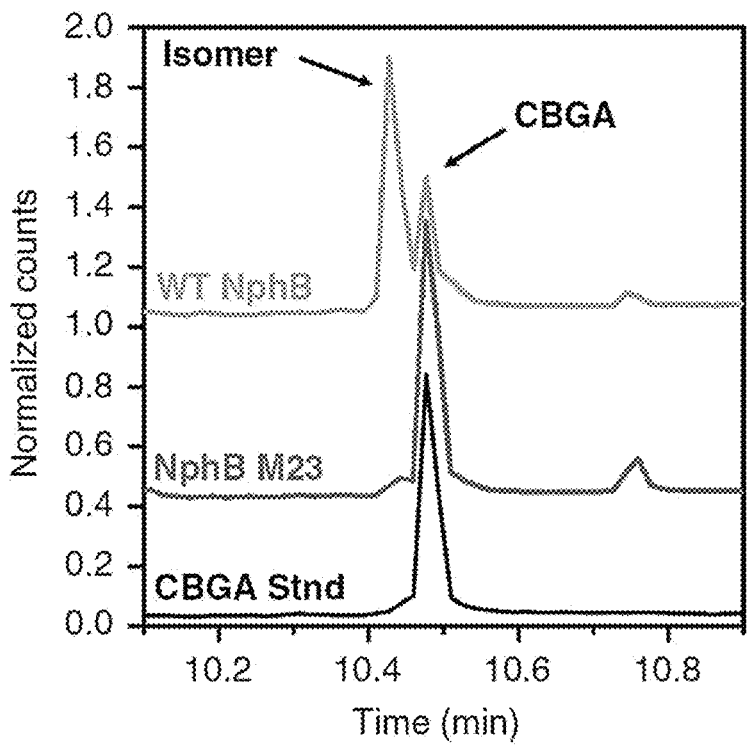

The designed mutant M23 not only shows dramatically improved catalytic efficiency for prenylation of OA, it is also extremely specific, producing only the correct CBGA product. WT NphB produces CBGA, but the dominant product is a prenylated isomer (FIG. 3C). In contrast the designed mutant M23 makes CBGA almost exclusively. Overall, the designed enzyme is a much more effective CBGA synthase than the non-specific prenylating wild-type enzyme.

The disclosure thus provides mutant NphB variants comprising (i) SEQ ID NO:30 and having at least a Y288X mutation, wherein X is A, N, S, V or a non-natural amino acid; (ii) SEQ ID NO:30 having at least a Y288X mutation, wherein X is A, N, S, V or a non-natural amino acid, and at least one other mutation selected from V49$Z_1$, F213$Z_2$, A232S, I234T, V271$Z_3$ and/or G286S, wherein $Z_1$ S, N, T or G, $Z_2$ is H, N or G and $Z_3$ is N or H; (iii) any of the mutations combination set forth in Table 1; (iv) any of (i), (ii) or (iii) comprising from 1-20 (e.g., 2, 5, 10, 15 or 20; or any value between 1 and 20) conservative amino acid substitutions and having NphB activity; (v) a sequence that is at least 85%, 90%, 95%, 98% or 99% identical to SEQ ID NO:1-29 or 30 and which has at least the mutations recited in (i), (ii) or (iii); (vi) an NphB mutation comprising any of the sequence recited in SEQ ID NOs:1-28 or 29 beginning at amino acid 21; or (vii) any sequence that is at least 99% identical to any of SEQ ID NOs: 1-28 or 29 and having NphB activity. By "NphB activity" means the ability of the enzyme to prenylate a substrate and more specifically to generate CBGA from OA.

As used herein a non-natural amino acid refers to amino acids that do not occur in nature such as N-methyl amino acids (e.g., N-methyl L-alanine, N-methyl L-valine etc.) or alpha-methyl amino acids, beta-homo amino acids, homo-amino acids and D-amino acids. In a particular embodiment, a non-natural amino acid useful in the disclosure includes a small hydrophobic non-natural amino acid (e.g., N-methyl L-alanine, N-methyl L-valine etc.).

In addition, the disclosure provides polynucleotides encoding any of the foregoing NphB variants. Due to the degeneration of the genetic code, the actual coding sequences can vary, while still arriving at the recited polypeptide for NphB mutants and variants. Exemplary polynucleotide sequence are provided in SEQ ID NOs: 66, 67 and 68 (corresponding to the polypeptide sequences of SEQ ID NO:23, 29 and 69 respectively). It will again be readily apparent that the degeneracy of the genetic code will allow for wide variation in the percent identity to SEQ ID NOs: 66, 67 and 68, while still encoding a polypeptide of SEQ ID NO:23, 29 and 69.

The disclosure also provide recombinant host cells and cell free systems comprising any of the NphB variant enzymes of the disclosure. In some embodiments, the recombinant cells and cell free systems are used carry out prenylation processes.

One objective of the disclosure is to produce the precursor GPP from glucose or prenol and/or isoprenol, which can then be used to prenylate added OA with a mutant NphB of the disclosure, thereby generating CBGA.

The disclosure thus provides a cell-free system comprising a plurality of enzymatic steps that converts glucose to geranyl pyrophosphate, wherein the pathway includes a purge valve and a PDH bypass enzymatic process.

Figure 1A:
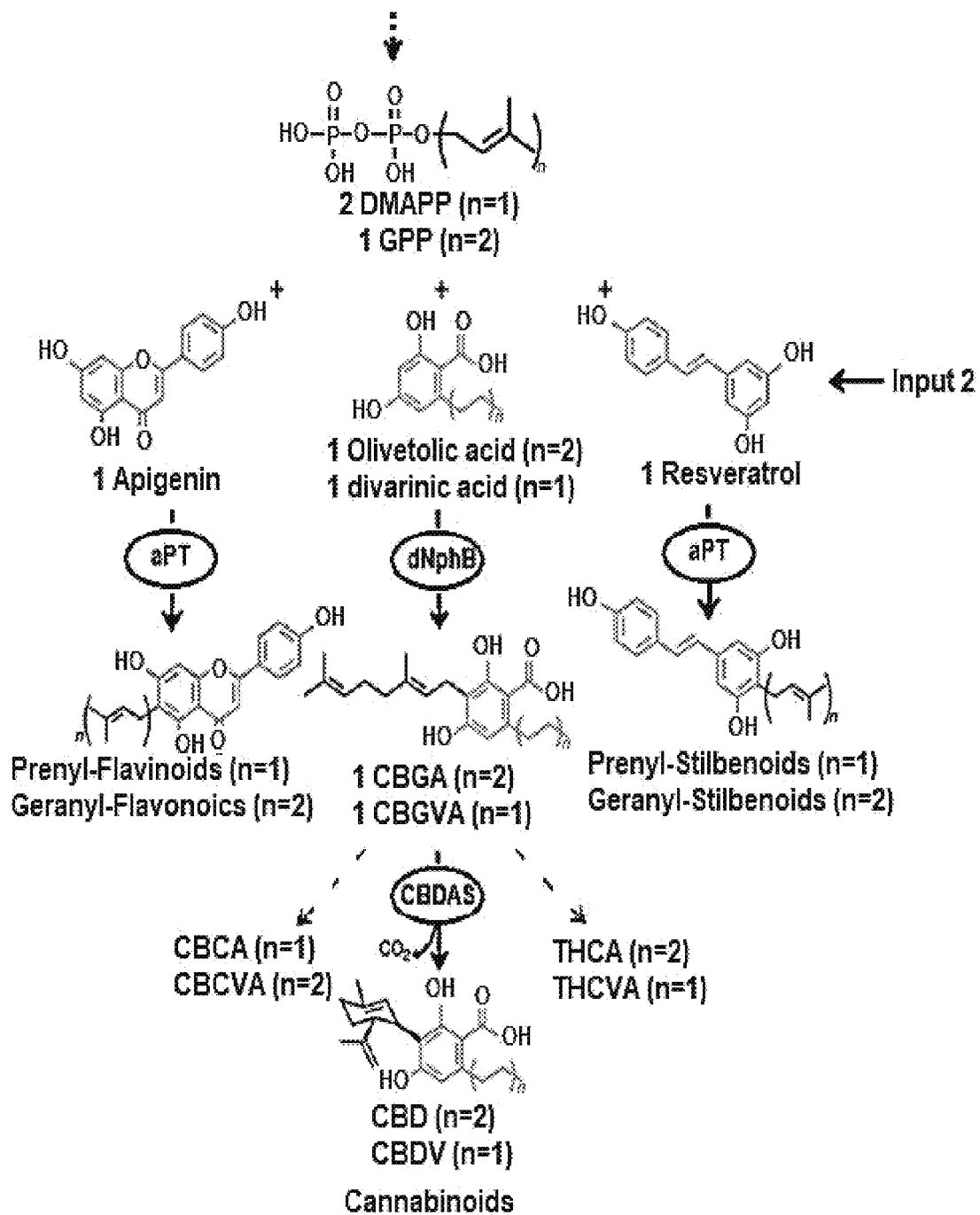
Figure 1B:

As depicted in FIG. 1B, one pathway of the disclosure comprises converting glucose to glucose-6-phosphate using a hexokinase. A hexokinase (EC 2.7.1.1) is an enzyme that phosphorylates hexoses (six-carbon sugars), forming hexose phosphate. Hexokinase possesses the ability to transfer an inorganic phosphate group from ATP to a substrate. Numerous hexokinase proteins from various organisms have been cloned and expressed. In some embodiments, the hexokinase comprises the sequence set forth in UniProtKB accession number P04806 from *Saccharomyces cerevisiae* (Sc)(incorporated herein by reference) as well as sequences that are at least 60%, 70%, 80%, 85%, 90%, 95%, 98%, 99% identical thereto and have hexokinase activity.

The glucose-6-phosphate is then converted to fructose-6-phosphate by phosphoglucoseisomerase (Pgi) (EC 5.3.1.9). Accordingly, in addition to the foregoing, the terms "phosphoglucoisomerase" or "Pgi" refer to proteins that are capable of catalyzing the formation of fructose-6-phosphate from glucose-6-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:31, or at least about 50%, 60%, 70%, 80%, 90%, 95%, 96%, 97%, 98%, 99% or greater sequence similarity, as calculated by NCBI BLAST, using default parameters and wherein the enzyme has phosphoglucoisomerase activity.

In another or further embodiment, a system or recombinant microorganism provided herein includes expression of a phosphofructokinase (Pfk, polyphosphate-dependent Pfk or homolog or variants thereof). This expression may be combined with other enzymes in the metabolic pathway. The Pfk can be derived from G. stearothermophilus (SEQ ID NO:32). In another embodiment, an engineered variant of Pfk can be used so long as it has phosphofructokinase activity and can convert fructose-6-phosphate to fructose-1,6-bisphosphate. Such engineered variants can be obtained by site-directed mutagenesis, directed evolutions and the like. Thus included within the disclosure are polypeptides that are at least 85-99% identical to a sequence as set forth in SEQ ID NO:32 and having phosphofructokinase activity (see, e.g., SEQ ID NOs:33-34).

In addition to the foregoing, the terms "fructose 1,6 bisphosphate aldolase" or "Fba" refer to proteins that are capable of catalyzing the formation of dihydroxyacetone phosphate and glyceraldehyde-3-phosphate from fructose 1,6-bisphosphate, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:35. Additional homologs include: *Synechococcus elongatus* PCC 6301 YP_170823.1 having 26% identity to SEQ ID NO:35; *Vibrio nigripulchritudo* ATCC 27043 ZP 08732298.1 having 80% identity to SEQ ID NO:35; *Methylomicrobium album* BG8 ZP_09865128.1 having 76% identity to SEQ ID NO:35; *Pseudomonas fluorescens* Pf0-1 YP_350990.1 having 25% identity to SEQ ID NO:35; and *Methylobacterium nodulans* ORS 2060 YP_002502325.1 having 24% identity to SEQ ID NO:35. Thus, the disclosure includes the use of polypeptides having from 26% to 100% identity to SEQ ID NO:35, wherein the polypeptide has bisophosphate aldolase activity. The sequences associated with the foregoing accession numbers are incorporated herein by reference.

In addition to the foregoing, the terms "triose phosphate isomerase" or "Tpi" refer to proteins that are capable of catalyzing the formation of glyceraldehyde-3-phosphate from dihydroxyacetone phosphate (DHAP), and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:36. Additional homologs include: *Rattus norvegicus* AAA42278.1 having 45% identity to SEQ ID NO:36; *Homo sapiens* AAH17917.1 having 45% identity to SEQ ID NO:36; *Bacillus subtilis* BEST7613 NP 391272.1 having 40% identity to SEQ ID NO:36; *Synechococcus elongatus* PCC 6301 YP_171000.1 having 40% identity to SEQ ID NO:36; and *Salmonella enterica* subsp. *enterica* serovar *Typhi* str. AG3 ZP_06540375.1 having 98% identity to SEQ ID NO:36. Thus, the disclosure incudes the use of polypeptides that have from 40% to 100% identity to SEQ ID NO:36 and have triose phosphate isomerase activity. The sequences associated with the foregoing accession numbers are incorporated herein by reference.

In a further step of the pathway, glyceraldehyde-3-phosphate can be converted to 1,3-bisphosphoglycerate. This enzymatic step can include a "purge valve system" (as discussed elsewhere herein). For example, glyceraldehyde-3-phosphate dehydrogenase (Gap, Tdh) converts glyceraldehyde-3-phosphate to 1,3-bisphospho-glycerate. In one embodiment, a wild-type Gap is used that uses NAD$^+$ as a cofactor (see, e.g., SEQ ID NO:37) or a mutant Gap comprising a P191D mutation (relative to the sequence of SEQ ID NO:37 and as shown in SEQ ID NO: 38). In another embodiment, a mutant Gap (mGap; e.g., having a D34A/L35R/T36K mutation; relative to the sequence of SEQ ID NO:37 and as shows in SEQ ID NO:39) is used that uses NADP$^+$ as a cofactor. In yet another embodiment, a combination of Gap and mGap (GapM6) are used. A molecular purge valve comprising a water generating NADH oxidase (NoxE) that specifically oxidizes NADH, but not NADPH can be used to recycle ("purge") NADH when a wild-type gap or P118D mutant gap is used that preferentially uses NAD$^+$.

In addition to the foregoing, the terms "NADH oxidase" or "NoxE" refer to proteins that are capable of oxidizing NADH to NAD$^+$, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to SEQ ID NO:18.

The pathway can further convert 1,3-bisphosphoglycerate to 3-phosphoglycerate by use of phosphoglycerate kinase (EC 2.7.2.3) (PGK; e.g., as provided in SEQ ID NO:40, or a homolog or variant thereof that is at least 80% identical thereto) which catalyzes the reversible transfer of a phosphate group from 1,3-bisphosphoglycerate (1,3-BPG) to ADP producing 3-phosphoglycerate (3-PG) and ATP. A molecular purge valve for ATP can be present to recycle ADP using, for example, a GTPase or other enzyme or a homolog or variant thereof).

The 3-phosphoglycerate can then be converted by a phosphoglycerate mutase (pgm; e.g., as provided in SEQ ID NO:41, or a homolog or variant thereof that is at least 80% identical thereto) to 2-phosphoglycerate.

An enolase (eno; e.g., as provided in SEQ ID NO:42, or a homolog or variant thereof that is at least 80% identical thereto) can then convert the 2-phosphoglycerate to phosphenolpyruvate (PEP).

A pyruvate kinase (pyk; e.g., as provided in SEQ ID NOs:43, 44, and 45, or a homolog or variant thereof that is at least 80% identical to any of SEQ ID NO:43, 44 or 45) converts PEP to pyruvate.

As mentioned above pyruvate dehydrogenase (PDH) is inhibited by products of the pathway. Thus, a PDH Bypass can be used to covert pyruvate to acetyl-coA. The PDH Bypass comprises two enzymatic steps: (i) pyruvate→acetyl phosphate catalyzed by pyruvate oxidase (e.g., PyOx from *Aerococcus viridans*; EC 1.2.3.3; see SEQ ID NO:46); and (ii) acetyal phosphate 4 acetyl-coA catalyzed by an acetyl phosphate transferase (aka phosphate acetyltransferase) (e.g., PTA from G. *stearothermophilus*).

As used herein a PyOx used in the composition and methods of the disclosure include sequences that are at least 85%, 90%, 95%, 98%, 99% identical to SEQ ID NO:46 and have pyruvate oxidase activity.

Phosphate acetyltransferase (EC 2.3.1.8) is an enzyme that catalyzes the chemical reaction of acetyl-CoA+phosphate to CoA+acetyl phosphate and vice versa. Phosphate acetyltransferase is encoded in *E. coli* by pta. PTA is involved in conversion of acetate to acetyl-CoA. Specifically, PTA catalyzes the conversion of acetyl-coA to acetyl-phosphate. PTA homologs and variants are known. There are approximately 1075 bacterial phosphate acetyltransferases available on NCBI. For example, such homologs and variants include phosphate acetyltransferase Pta (*Rickettsia felis* URRWXCal2) gi|67004021|gb|AAY60947.1|(67004021); phosphate acetyltransferase (*Buchnera aphidicola* str. Cc (*Cinara cedri*)) gi|116256910|gb|ABJ90592.1| (116256910); pta (*Buchnera aphidicola* str. Cc (*Cinara cedri*)) gi|116515056|ref|YP_802685.1|(116515056); pta (*Wigglesworthia glossinidia* endosymbiont of *Glossina brevipalpis*) gi|25166135|dbj|BAC24326.1|(25166135); Pta (*Pasteurella multocida* subsp. *multocida* str. Pm70) gi|12720993|gb|AAK02789.1|(12720993); Pta (*Rhodospirillum rubrum*) gi|25989720|gb|AAN75024.1| (25989720); pta (*Listeria welshimeri* serovar 6b str. SLCC5334) gi|116742418|emb|CAK21542.1|(116742418); Pta (*Mycobacterium avium* subsp. *paratuberculosis* K-10) gi|41398816|gb|AAS06435.1|(41398816); phosphate acetyltransferase (pta) (*Borrelia burgdorferi* B31) gi|15594934|ref|NP_212723.1|(15594934); phosphate acetyltransferase (pta) (*Borrelia burgdorferi* B31) gi|2688508|gb|AAB91518.1|(2688508); phosphate acetyltransferase (pta) (*Haemophilus influenzae* Rd KW20) gi|1574131|gb|AAC22857.1|(1574131); Phosphate acetyltransferase Pta (*Rickettsia bellii* RML369-C) gi|91206026|ref|YP_538381.1|(91206026); Phosphate acetyltransferase Pta (*Rickettsia bellii* RML369-C) gi|91206025|ref|YP_538380.1|(91206025); phosphate acetyltransferase pta (*Mycobacterium tuberculosis* F11) gi|148720131|gb|ABR04756.1|(148720131); phosphate acetyltransferase pta (*Mycobacterium tuberculosis* str. Haarlem) gi|134148886|gb|EBA40931.1|(134148886); phosphate acetyltransferase pta (*Mycobacterium tuberculosis* C) gi|124599819|gb|EAY58829.1|(124599819); Phosphate acetyltransferase Pta (*Rickettsia bellii* RML369-C) gi|91069570|gb|ABE05292.1|(91069570); Phosphate acetyltransferase Pta (*Rickettsia bellii* RML369-C) gi|91069569|gb|ABE05291.1|(91069569); phosphate acetyltransferase (pta) (*Treponema pallidum* subsp. *pallidum* str. Nichols) gi|15639088|ref|NP_218534.l|(15639088); and phosphate acetyltransferase (pta) (*Treponema pallidum* subsp. *pallidum* str. Nichols) gi|3322356|gb|AAC65090.1| (3322356), each sequence associated with the accession number is incorporated herein by reference in its entirety.

Turning again to FIG. 1B, the pathway includes the conversion of acetyl-coA to acetoacetyl-coA. The conversion of acetyl-coA to acetoacetyl-CoA is performed by an acetyl-CoA acetyltransferase (e.g., PhaA). Numerous acetyl-coA acetyltransferases are known in the art. For example, acetyl-coA acetyltransferase from *R. eutropha*. In another embodiment, the acetyl-coA acetyl transferase has an amino acid sequence that is at least 85%, 90%, 95%, 98%, 99% or 100% identical to SEQ ID NO:47.

Acetoacetyl-CoA and acetyl-Coa can be converted to HMG-CoA by the enzyme HMG-CoA synthase having an A110G mutation (see, e.g., SEQ ID NO:48) or a homolog or variant thereof having 85%-99% sequence identity thereto.

The HMG-CoA is then reduced to mevalonate by the actions of NADPH and HMG-CoA reductase (see, e.g., SEQ ID NO:49) or a homolog or variant thereof having from 85%-99% sequence identity thereto.

Mevalonate is then phosphorylated by ATP and the action of mevalonate kinase (MVK) to produce mevalonate-5-phosphate and ADP. Melavonate kinases are known in the art and include sequence that are at least 85-100% (e.g., 85%, 90%, 95%, 98%, 99%) identical to the sequence of SEQ ID NO:50 and which have mevalonate kinase activity.

The mevalonate-5-phosphate is further phosphorylated by ATP and the actions of phosphomevalonate kinase (PMVK) to produce mevalonate-5-diphosphate and ADP. Phosphomevalonate kinases are known in the art and include sequence that are at least 85-100% (e.g., 85%, 90%, 95%, 98%, 99%) identical to the sequence of SEQ ID NO:51 and which have phosphomevalonate kinase activity.

Mevalonate-5-diphosphate is decarboxylated by ATP and the actions of diphosphomevalonate decarboxylase (MDC) to produce ADP, $CO_2$ and isopentyl pyrophosphate. Diphosphomevalonate decarboxylases are known in the art and include sequence that are at least 85-100% (e.g., 85%, 90%, 95%, 98%, 99%) identical to the sequence of SEQ ID NO:52 and which have diphosphomevalonate kinase activity.

Figure 7:
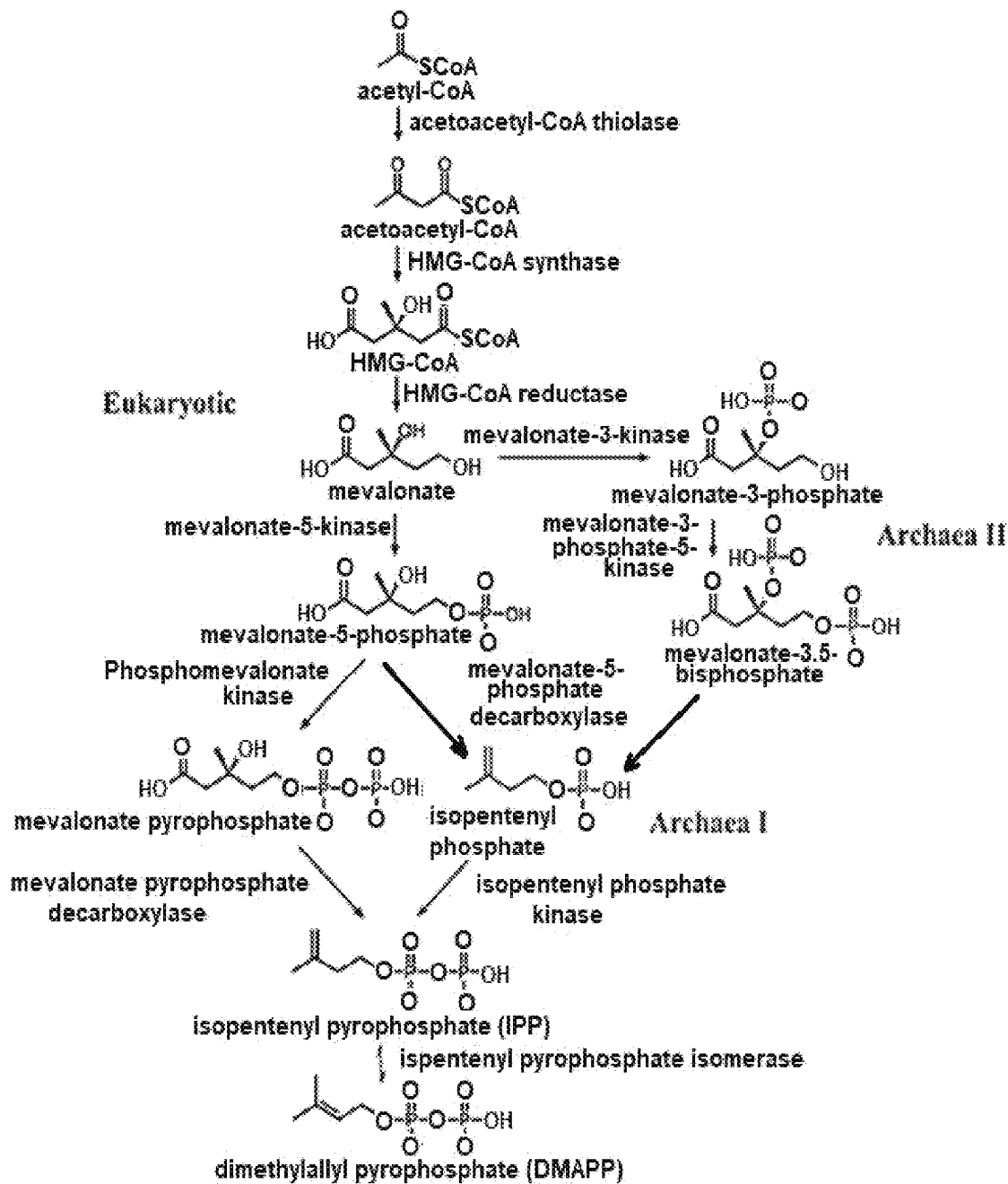
FIG. 7 shows the various canonical (Eukaryotic) and non-canonical (Archael I and II) mevalonate pathways that can be used to generate IPP/DMAPP from acetyl-CoA (or mevalonate).

Various other mevalonate pathways can be used (see, e.g., FIG. 7).

Geranyl pyrophosphate (GPP) is then formed from the combination of DMAPP and isopentyl pyrophosphate in the presence of farnesyl-PP synthase having an S82F mutation relative to SEQ ID NO:53. In one embodiment, the farnesyl-diphosphate synthase has a sequence that is at least 95%, 98%, 99% or 100% identical to SEQ ID NO:53 having an S82F mutation and which is capable of forming geranyl pyrophosphate from DMAPP and isopentyl pyrophosphate.

GPP can then be used as a substrate for a number of pathways leading to prenyl-flavanoids, geranyl-flavonoics, prenyl-stilbenoids, geranyl-stilbenoids, CBGA, CBGVA, CBDA, CBDVA, CBGVA, CBCVA, THCA and THCVA (see, e.g., FIG. 1A)

For example, with the NphB mutant, as described above, in hand (e.g., an M23 mutant), the ability to produce CBGA directly from glucose and OA was tested using the full synthetic biochemistry system, including the PDH bypass (see, FIG. 1A and FIG. 1B). The initial productivity using M23 in the system was 67 mg $L^{-1}hr^{-1}$ with a final titer of 744±34 mg $L^{-1}$ of CBGA. This was 100-fold faster than CBGA production using WT NphB, and reached a titer 21-fold higher. It is noted that with the mutant NphB enzyme, maximum titers were reached within 24 hours and the production stopped, yet with the wild-type enzyme, the system ran continuously for up to 4 days suggesting that enzymes and cofactors remain active and viable for longer periods of time. It was noted that once ~500 mg $L^{-1}$ CBGA was produced, the reactions turned cloudy. The precipitate was collected and a mix of enzymes was identified in the precipitate by SDS-PAGE analysis, indicating that high-levels of CBGA in solution causes enzymes to precipitate. A more effective system was developed to remove product during the reaction.

Figure 4A:
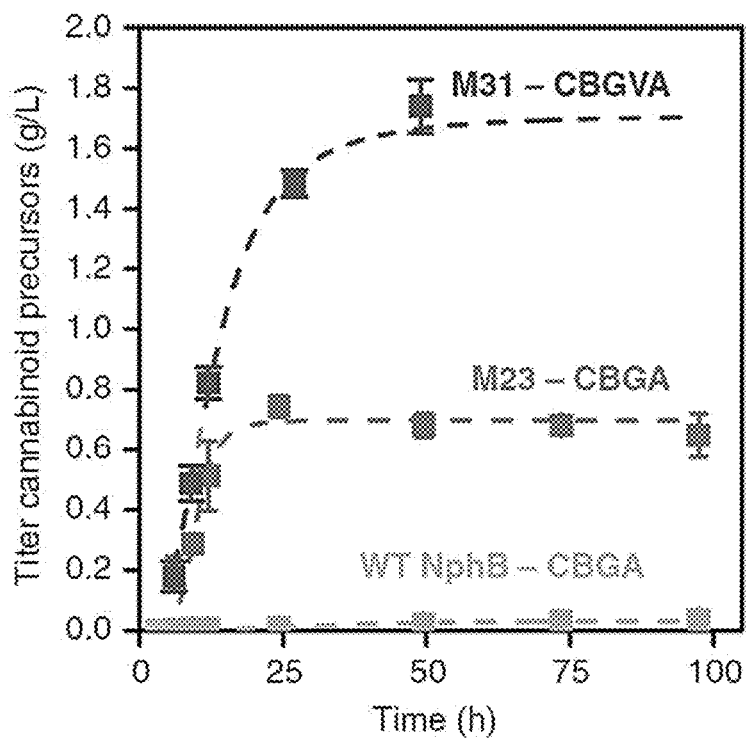
FIG. 4A-C shows the evaluation of the cell-free prenylation system for the production of various cannabinoids. (A) The cell-free enzymatic production (from glucose) of cannabinoid precursors over time. CBGA production using M23 is shown in the light green trace and WT NphB in the dark green trace. The production of CBGVA using M31 is shown in the light blue trace. The concentration of NphB for WT, M23 and M31 was fixed at 0.5 mg/mL (n=3). (B) Using a nonane flow CBGA capture system, a higher titer of CBGA (1.2 g/L) was obtained. The nonane layer was exchanged using a peristaltic pump, which circulated the nonane in the direction indicated by the arrows. This system is able to dilute the CBGA into multiple milliliters of nonane and buffer, which decreases the amount of CBGA in the reaction. (C) Production of cannabinoids over time using CBDAS. CBDA production is shown in the dark purple trace, and CBDVA production is shown in the light purple trace.
Figure 4B:
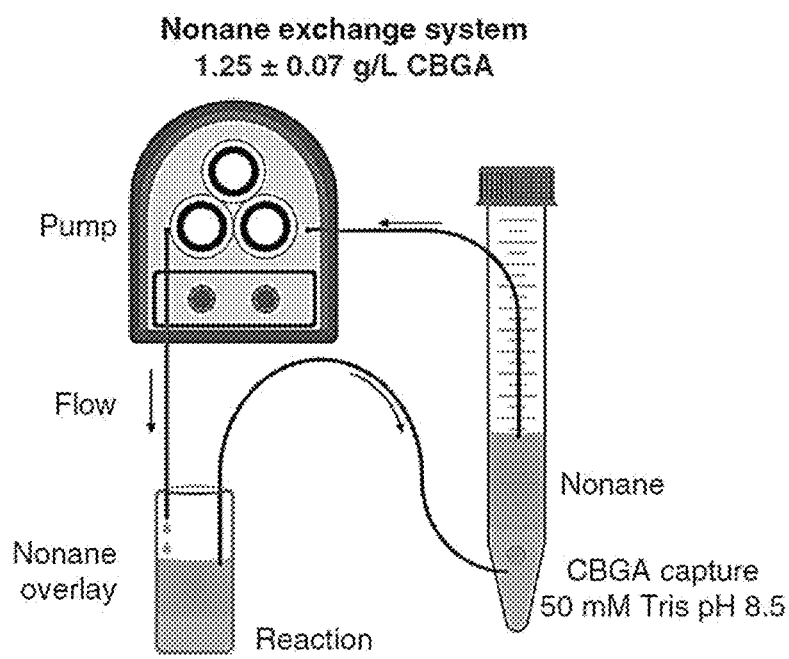
Figure 4C:
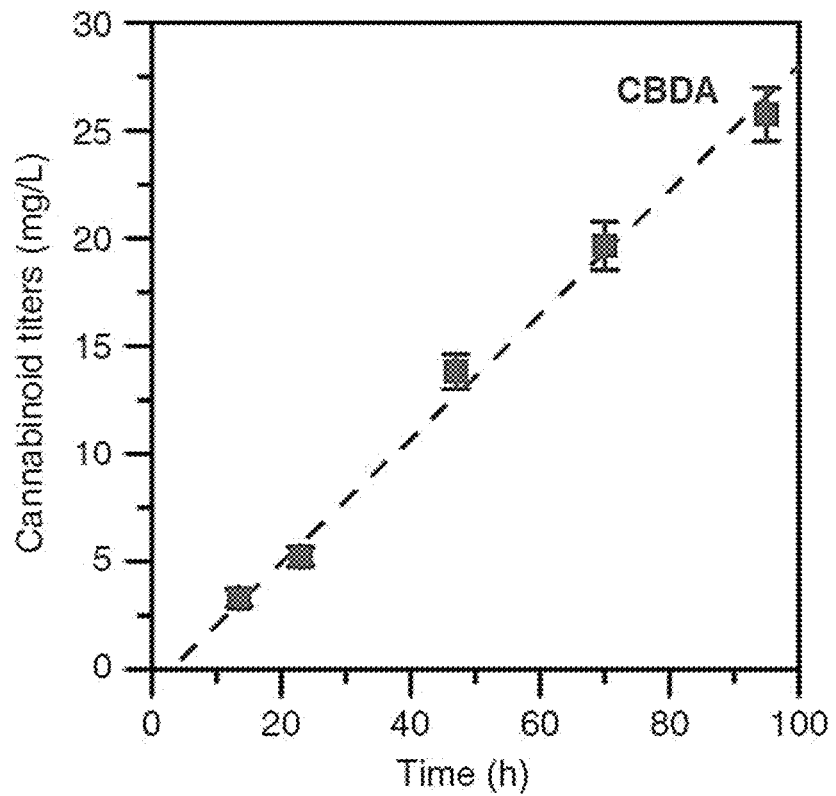

Although a nonane overlay was used in the reactions to extract CBGA, CBGA is more soluble in water than nonane, which limits the amount of CBGA that can be extracted with a simple overlay. Thus, a flow system was designed that would capture CBGA from the nonane layer and trap it in a separate water reservoir (FIG. 4b). By implementing this flow system a lower concentration of CBGA was maintained in the reaction vessel to mitigate enzyme precipitation. The flow system indeed improved the final titers to 1.2 g/L.

Experiments were then performed to produce the precursor of many rare cannabinoids, CBGVA, by replacing OA in the system with divirinic acid (DA) (see, e.g., FIG. 1B). The designed enzymes were first tested to determine if they would be active on a DA substrate. The two best mutants M23 and M31 were tested as well as WT NphB for their ability to produce CBGVA. The kinetic data shown in Table 2 indicated that M31 was far superior, with catalytic efficiencies 15-fold higher than M23 and 650-fold higher than WT NphB. Thus, further efforts utilized M31 to produce CBGVA from glucose and divarinic acid. As shown in FIG. 4A, CBGVA was produced at a max productivity of ~107 mg $L^{-1}$ $hr^{-1}$, and reached a final titer of 1.74±0.09 g $L^{-1}$, converting 92% of the divarinic acid added to CBGVA. The nonane flow system was not needed for the production of CBGVA because CBGVA was less potent in precipitating enzymes.

To demonstrate that the approach can ultimately be used to prepare additional cannabinoids, CBDA synthase was employed to convert CBGA into CBDA and CBGVA into CBDVA. For CBDA, the nonane overlay contained a significant quantity of CBGA, so by simply transferring the nonane overlay to a solution containing CBDA synthase, CBGA was converted into CBDA at a constant rate of 14.4±0.8 mg $L^{-1}$ $hr^{-1}$ mg total $protein^{-1}$ for 4 days.

Due to the limited solubility of CBGVA in nonane, the CBGVA was extracted and added to a reaction containing CBDA synthase. The product of the CBDA synthase was in fact CBDVA using GC-MS.

The disclosure thus provides a cell free system for the production of GPP. Further the disclosure provides a cell free approach for the production of an array of pure cannabinoids and other prenylated natural products using the GPP pathway in combination with a mutant NphB or using substrates for the mutant NphB of the disclosure. The success of this method uses the engineered prenyltransferase of the disclosure (e.g., NphB mutants as described above), which was active, highly specific and eliminated the need for the native transmembrane prenyltransferase. The modularity and flexibility of the synthetic biochemistry platform provided herein has the benefits of a bio-based approach, but removes the complexities of satisfying living systems. For example, GPP toxicity did not factor into the design process. Moreover, OA is not taken up by yeast so the approach of adding it exogenously would not necessarily be possible in cells. Indeed, the flexibility of cell free systems can greatly facilitate the design-build-test cycles required for further optimization, additional pathway enzymes and reagent and co-factor modifications.

Turning to the overall pathway of FIG. 1, the disclosure provides a number of steps catalyzed by enzymes to covert a "substrate" to a product. In some instances a step may utilize a co-factor, but some steps do not use co-factors (e.g., NAD(P)H, ATP/ADP etc.). Table 3 provides a list of enzymes, organisms and reaction amounts used as well as accession numbers (the sequences associated with such accession numbers are incorporated herein by reference).

TABLE 3

Enzymes used in the enzymatic platform

|  | Enzyme Abb. | Full Name | Organism | Amount Added to Rxn (mg/mL) | Acquisition Number |
|---|---|---|---|---|---|
| 1 | Hex | Hexokinase | S. cerevisiae | 0.02 | Sigma Aldrich |
| 2 | Pgi | Glucose-6-phosphate isomerase | G. thermodenitrificans | 0.48 | ABO6822 or ARA98689.1 |
| 3 | PfkA | Phosphofructokinase | G. stearothermophilus | 0.18 | KOR92562 or P00512.2 |
| 4 | Fba | Fructose-1,6-bisphosphate aldolase | S. aureus | 0.03 | BAR10119 or PSN28048.1 |
| 5 | TpiA | Triose phosphate isomerase | G. stearothermophilus | 0.16 | KOR95273 or P00943.2 |
| 6 | Gap | Gald-3-P dehydrogenase | E. coli K12 | 0.07 | NP_416293 |
| 7 | mGap | Gald-3-P dehydrogenase D34A/L35R/T36K | G. stearothermophilus | 0.18 | NP_416293 |
| 8 | NoxE | NADH Oxidase | L. lactis | 0.25 | WP_015425842 |
| 9 | Pgk | Phosphoglycerate Kinase | G. stearothermophilus | 0.06 | NP_415276 |
| 10 | dPgm | Phosphoglycerate Mutase (2,3 BPG dependent) | E. coli K12 | 0.29 | NP_417259 |
| 11 | Eno | Enolase | E. coli K12 | 0.08 | KOR95272 or BAE76853.1 |
| 12 | PykF | Pyruvate Kinase (FBP dependent) | E. coli K12 | 0.37 | NP_416191 |
|  | PDH | Pyruvate Dehydrogenase AceE AceF Lpd | E. coli K12 | 0.99 | NP_414656 NP_414657 NP_414658 |
| 13 | PyOx | Pyruvate Oxidase | A. viridans | 1 U | AG Scientific |
| 14 | PTA | Acetyl-phosphate transferase | G. stearothermophilus | 0.06 | WP_053532564 |
| 15 | PhaA | Acetyl-CoA acetyltransferase | R. eutropha | 0.12 | CAJ92573 |
| 16 | HMGS A110G | HMG-CoA Synthase A110G | E. faecalis | 0.18 | WP_010785222 |
| 17 | HMGR | HMG-CoA Reductase | E. faecalis | 0.16 | AAG02439 |
| 18 | MVK | Mevalonate Kinase | M. mazei | 0.14 | AAM31458 |
| 19 | PMVK | Phosphomevalonate Kinase | S. pneumonia | 0.2 | WP_000562411 |
| 20 | MDC | Diphosphomevalonate Kinase | S. pneumonia | 0.19 | NP_357933 |

TABLE 3-continued

Enzymes used in the enzymatic platform

| | Enzyme Abb. | Full Name | Organism | Amount Added to Rxn (mg/mL) | Acquisition Number |
|---|---|---|---|---|---|
| 21 | IDI | Isopentyl-PP Isomerase | *E. coli* K12 | 0.3 | NP_417365 |
| 22 | FPPS S82F | Farnesyl-PP synthase S82F | *G. stearothermophilus* | 0.09 | KOR95521 |
| 23 | NphB | Aromatic prenyltransferase | *Streptomyces* sp. CL190 | Variable | BAE00106.1 |
| 24B | CBDAS | Cannabidiolic Acid Synthase | *C. sativa* | | AKC34419 |
| 25 | Ppase | Pyrophosphatase | *G. stearothermophilus* | 0.11 | O05724 |
| 26 | Cat | Catalase | *C. glutamicum* | 0.1 U | Sigma Aldrich |
| | GorA | Glutathione Reductase | *E. coli* K12 | 0.06 | NP_417957 |

As described above, prenylation of olivetolate by GPP is carried out by the activity of the mutant NphB polypeptides described herein and above.

The disclosure provides an in vitro method of producing prenylated compounds and moreover, an in vitro method for producing cannabinoids and cannabinoid precursors (e.g., CBGA, CBGVA or CBGXA where 'X' refers to any chemical group). In one embodiment, of the disclosure cell-free preparations can be made through, for example, three methods. In one embodiment, the enzymes of the pathway, as described herein, are purchased and mixed in a suitable buffer and a suitable substrate is added and incubated under conditions suitable for production of the prenylated compound or the cannabinoids or cannabinoid precursor (as the case may be). In some embodiments, the enzyme can be bound to a support or expressed in a phage display or other surface expression system and, for example, fixed in a fluid pathway corresponding to points in the metabolic pathway's cycle.

Figure 5A:
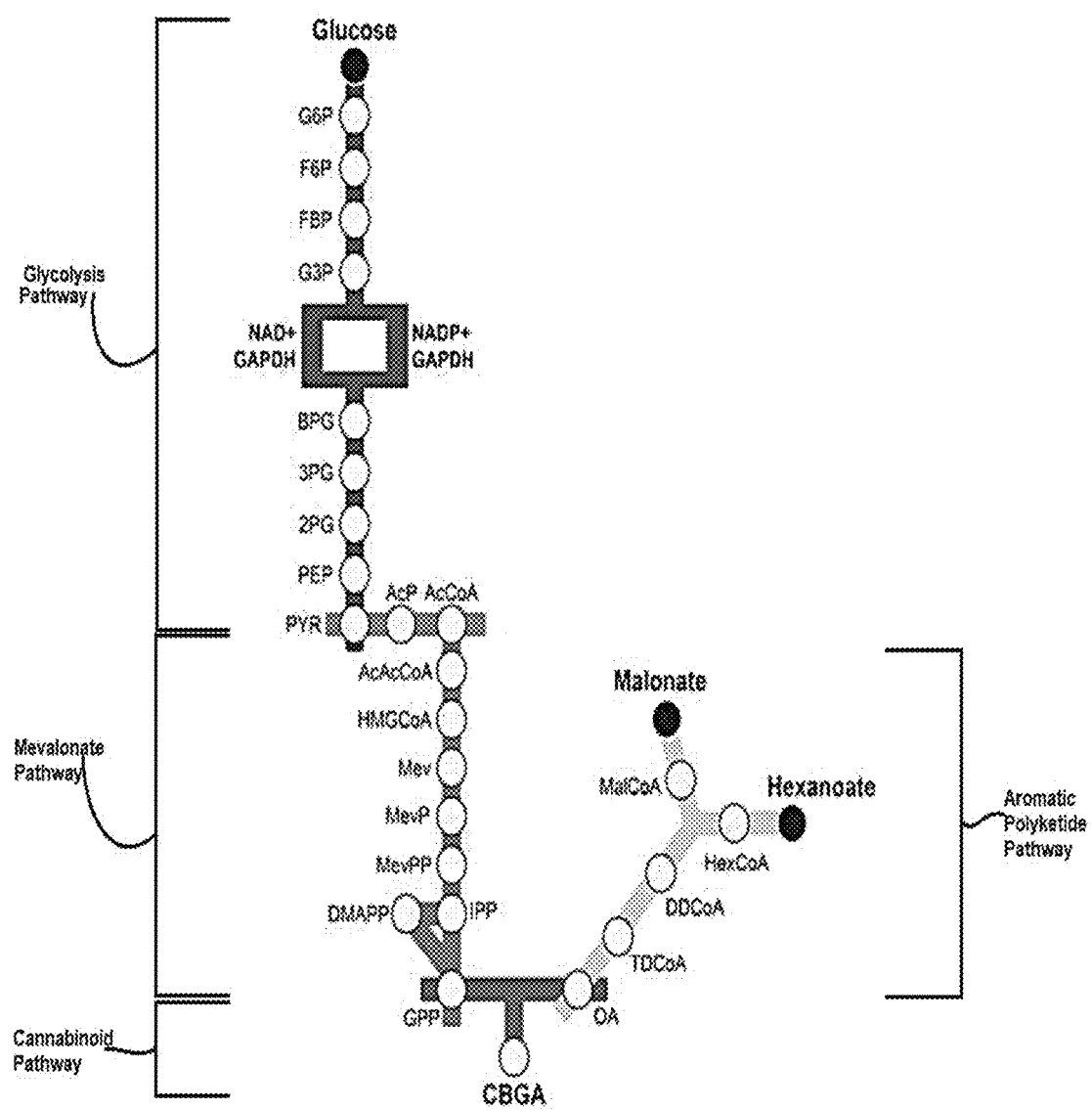
FIG. 5A-C shows Pathway schematics for the MatB and MdcA (transferase) paths. (A) This is the schematic for the MatB path. The malonyl-CoA production is ATP dependent, but otherwise not connected with the pathway. A titer is the the pathway is 12 mg/L. (B) This is the schematic for the MdcA transferase path. The malonyl-CoA production is no longer ATP dependent, and is tied in to the pyruvate oxidation path, and the mevalonate path. A titer for the system is 42 mg/L. (C) shows additional detail of exemplary steps in the polyketide module of the pathway shows in (A) and (B).
Figure 5B:
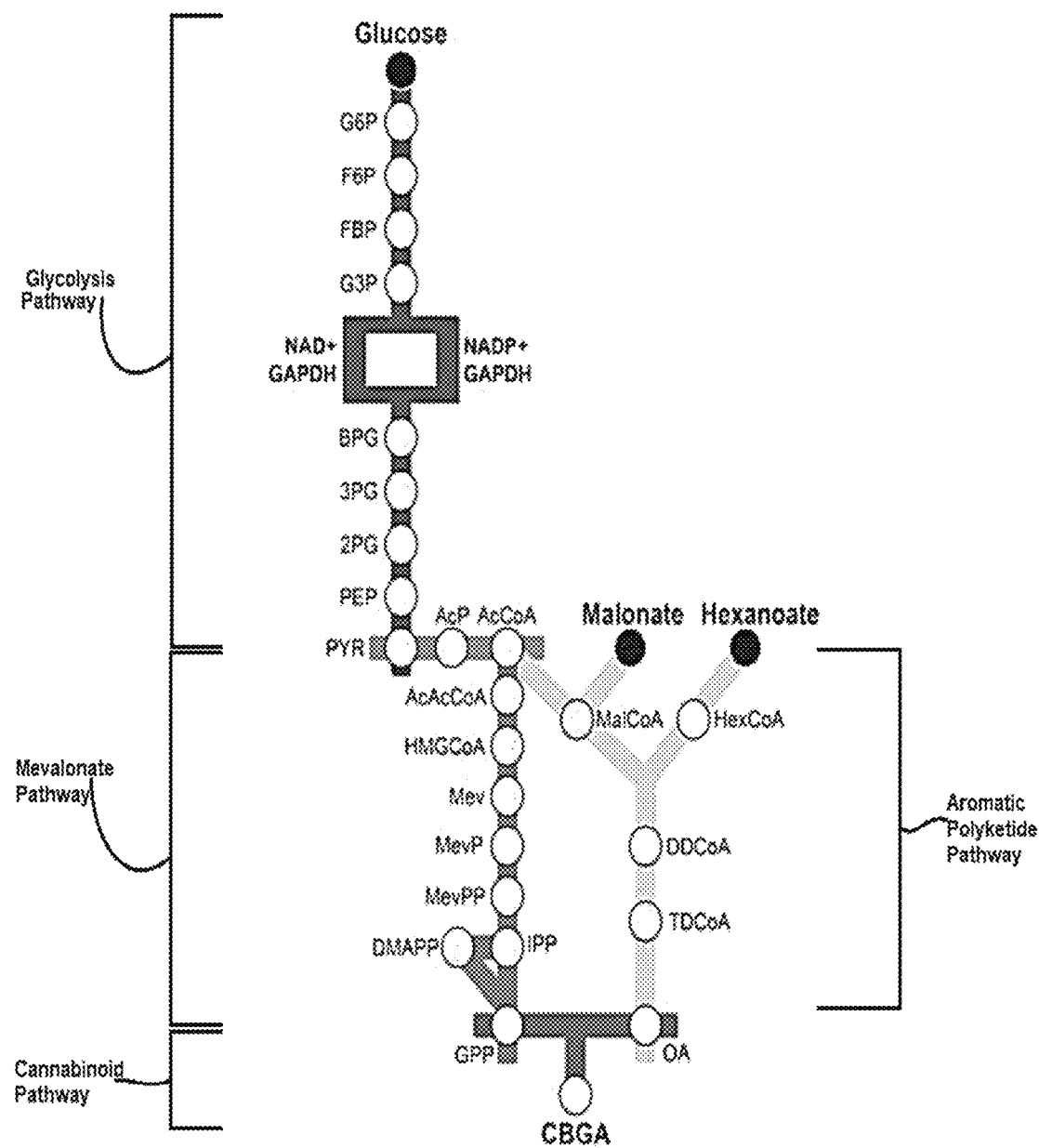
Figure 5C:
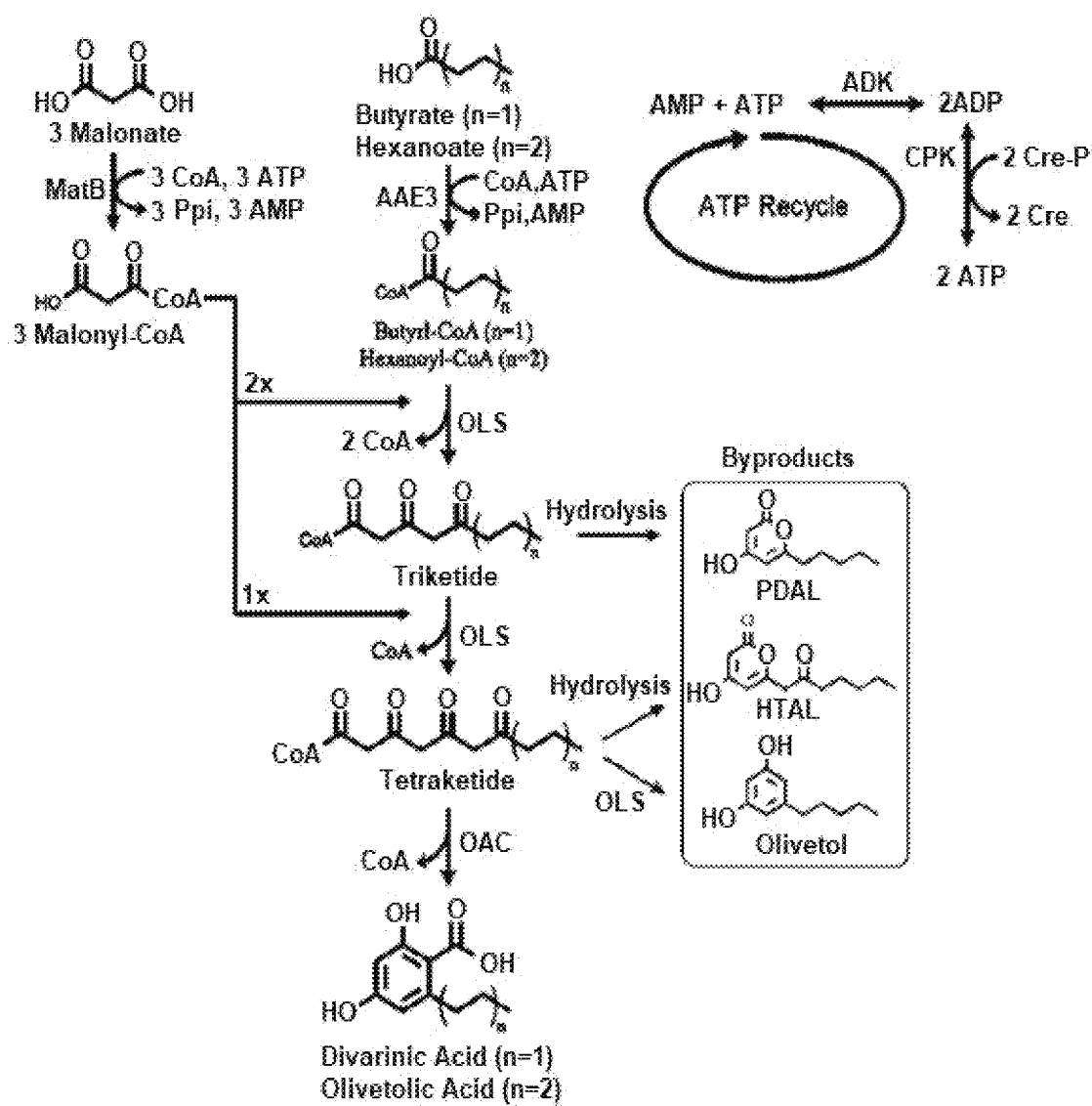
Figure 6:
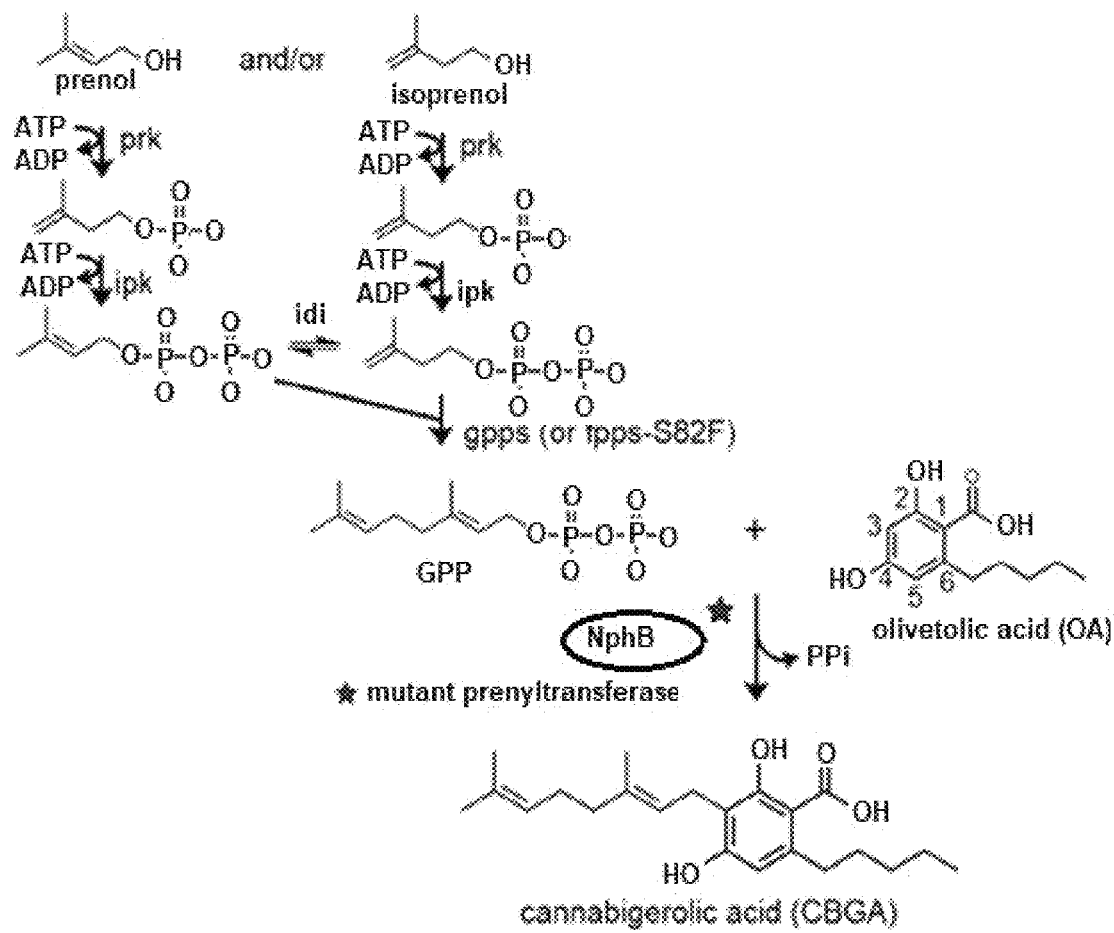
FIG. 6 shows a pathway schematic for the (iso)prenol to GPP paths. Isoprenol or prenol can be turned in to geranylpyrophosphate using ATP and necessary kinases.

FIG. 5A-B depict the pathway as various "modules" (e.g., glycolysis module, mevalonate/isoprenoid module, cannabinoid module, polyketide module). For example, the isoprenoid module produces the isoprenoid geranyl pyrophosphate (GPP) from acetyl-CoA via the mevalonate pathway. The aromatic polyketide module utilizes a Type III polyketide synthase (PKS) to convert hexanoyl-CoA and malonyl-CoA (derived from acetyl-CoA) into olivetolic acid (OA). The cannabinoid module, uses products from the isoprenoid module and the polyketide module to yield cannabigerolic acid, which is then converted into the final cannabinoid by a cannabinoid synthase.

In another embodiment, one or more polynucleotides encoding one or more enzymes of the pathway are cloned into one or more microorganism under conditions whereby the enzymes are expressed. Subsequently the cells are lysed and the lysed preparation comprising the one or more enzymes derived from the cell are combined with a suitable buffer and substrate (and one or more additional enzymes of the pathway, if necessary) to produce the prenylated compound or the cannabinoids or cannabinoid precursor. Alternatively, the enzymes can be isolated from the lysed preparations and then recombined in an appropriate buffer. In yet another embodiment, a combination of purchased enzymes and expressed enzymes are used to provide a pathway in an appropriate buffer. In one embodiment, heat stabilized polypeptide/enzymes of the pathway are cloned and expressed. In one embodiment, the enzymes of the pathway are derived from thermophilic microorganisms. The microorganisms are then lysed, the preparation heated to a temperature wherein the heat stabilized polypeptides of the pathway are active and other polypeptides (not of interest) are denatured and become inactive. The preparation thereby includes a subset of all enzymes in the microorganism and includes active heat-stable enzymes. The preparation can then be used to carry out the pathway to produce the prenylated compound or the cannabinoids or cannabinoid precursor.

For example, to construct an in vitro system, all the enzymes can be acquired commercially or purified by affinity chromatography, tested for activity, and mixed together in a properly selected reaction buffer.

An in vivo system is also contemplated using all or portions of the foregoing enzymes in a biosynthetic pathway engineered into a microorganism to obtain a recombinant microorganism.

The disclosure also provides recombinant organisms comprising metabolically engineered biosynthetic pathways that comprise a mutant nphB for the production of prenylated compounds and may further include one or more additional organisms expressing enzymes for the production of cannabinoids (e.g., a co-culture of one set of microorganism expressing a partial pathway and a second set of microorganism expression yet a further or final portion of the pathway etc.).

In one embodiment, the disclosure provides a recombinant microorganism comprising elevated expression of at least one target enzyme as compared to a parental microorganism or encodes an enzyme not found in the parental organism. In another or further embodiment, the microorganism comprises a reduction, disruption or knockout of at least one gene encoding an enzyme that competes with a metabolite necessary for the production of a desired metabolite or which produces an unwanted product. The recombinant microorganism expresses an enzymes that produces at least one metabolite involved in a biosynthetic pathway for the production of, for example, the prenylated compound or the cannabinoids or cannabinoid precursor. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of, for example, a prenylated compound or cannabinoids or cannabinoid precursors. The target enzyme is encoded by, and expressed from, a polynucleotide derived from a suitable biological source. In some embodiments, the polynucleotide comprises a gene derived from a bacterial or yeast source and recombinantly engineered into the microorganism of the disclosure. In another embodiment, the polynucleotide encoding the desired target enzyme is naturally occurring in the organism but is recombinantly engineered to be overexpressed compared to the naturally expression levels.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; and (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another (see, e.g., FIG. 1A-B). Gene products belong to the same "metabolic pathway" if they, in parallel or in series, act on the same substrate, produce the same product, or act on or produce a metabolic intermediate (i.e., metabolite) between the same substrate and metabolite end product. The disclosure provides recombinant microorganism having a metabolically engineered pathway for the production of a desired product or intermediate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite or to express a polypeptide nor normally expressed. In an illustrative embodiment, the introduction of genetic material into a parental microorganism results in a new or modified ability to produce acetyl-phosphate and/or acetyl-CoA through through a PDH bypass using pyruvate oxidase and acetylphosphate transferase. The genetic material introduced into the parental microorganism contains gene(s), or parts of gene(s), coding for one or more of the enzymes involved in a biosynthetic pathway for the production of prenylated compounds or cannabinoids or cannabinoid precursors, and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable by-products) or eliminates the enzyme from cell free preparations that may compete with a biosynthetic pathway developed from lysed preparations.

An "enzyme" means any substance, typically composed wholly or largely of amino acids making up a protein or polypeptide that catalyzes or promotes, more or less specifically, one or more chemical or biochemical reactions.

A "protein" or "polypeptide", which terms are used interchangeably herein, comprises one or more chains of chemical building blocks called amino acids that are linked together by chemical bonds called peptide bonds. A protein or polypeptide can function as an enzyme.

As used herein, the term "metabolically engineered" or "metabolic engineering" involves rational pathway design and assembly of biosynthetic genes, genes associated with operons, and control elements of such polynucleotides, for the production of a desired metabolite, such as an acetyl-phosphate and/or acetyl-CoA, higher alcohols or other chemical, in a microorganism. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., glucose etc.), an intermediate in (e.g., acetyl-coA), or an end product (e.g., CBDA) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon. A mutation that gives rise to a different primary sequence of a protein can be referred to as a mutant protein or protein variant.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e. a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a hexokinase. This microorganism can act as a parental microorganism in the generation of a microorganism modified to express or over-express a second target enzyme e.g., a fructose-1,6-bisphosphate aldolase. In turn, that microorganism can be modified to express or over express e.g., an NADH oxidase and a Gald-3-phosphate dehydrogenase (and mutants thereof), which can be further modified to express or over express a third target enzyme, e.g., a phosphoglycerate kinase etc. As used herein, "express" or "over express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules into the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme into a parental microorganism.

Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells. The sequences provided herein and the accession numbers provide those of skill in the art the ability to obtain and obtain coding sequences for various enzymes of the disclosure using readily available software and basis biology knowledge.

The sequence listing appended hereto provide exemplary polypeptides useful in the methods described herein. It is understood that the addition of sequences which do not alter the activity of a polypeptide molecule, such as the addition of a non-functional or non-coding sequence (e.g., polyHIS tags), is a conservative variation of the basic molecule.

It is understood that a polynucleotide described herein include "genes" and that the nucleic acid molecules described above include "vectors" or "plasmids."

The term "polynucleotide," "nucleic acid" or "recombinant nucleic acid" refers to polynucleotides such as deoxyribonucleic acid (DNA), and, where appropriate, ribonucleic acid (RNA).

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

The disclosure provides a number of polypeptide sequences in the sequence listing accompanying the present application, which can be used to design, synthesize and/or isolate polynucleotide sequences using the degeneracy of the genetic code or using publicly available databases to search for the coding sequences.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a starting material, but also intermediate and end product metabolites used in a pathway associated with a metabolically engineered microorganism as described herein.

"Transformation" refers to the process by which a vector is introduced into a host cell. Transformation (or transduction, or transfection), can be achieved by any one of a number of means including electroporation, microinjection, biolistics (or particle bombardment-mediated delivery), or agrobacterium mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For *E. coli* expression vectors, it is useful to include an *E. coli* origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than BLASTp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers and sequences for various genes, homologs and variants useful in the generation of recombinant microorganism and proteins for use in in vitro systems. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

It is well within the level of skill in the art to utilize the sequences and accession number described herein to identify homologs and isozymes that can be used or substituted for any of the polypeptides used herein. In fact, a BLAST search of any one of the sequences provide herein will identify a plurality of related homologs.

Culture conditions suitable for the growth and maintenance of a recombinant microorganism provided herein are known (see, e.g., "Culture of Animal Cells—A Manual of Basic Technique" by Freshney, Wiley-Liss, N.Y. (1994), Third Edition). The skilled artisan will recognize that such conditions can be modified to accommodate the requirements of each microorganism.

It is understood that a range of microorganisms can be modified to include all or part of a recombinant metabolic pathway suitable for the production of prenylated compounds or cannabinoids or cannabinoid precursors. It is also understood that various microorganisms can act as "sources" for genetic material encoding target enzymes suitable for use in a recombinant microorganism provided herein.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), 4-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Chemicals and Reagents. Yeast hexokinase and *Corynebacterium glutamicum* catalase were purchased from Sigma Aldrich. *Aerococcus viridians* pyruvate oxidase was purchased from A.G. scientific. All cofactors and reagents were purchased from either Sigma Aldrich or Thermo Fisher Scientific, with the exception of olivetolic acid, which was purchased from Santa Cruz Biotechnology and divarinic acid, which was purchased from Toronto Research Chemicals.

Cloning and purification of enzymes. The NphB gene was purchased as a gene block from IDT DNA, and cloned into a pET 28(+) vector using the Gibson Assembly method. The remaining enzymes were amplified from genomic DNA or a plasmid, and cloned into pET28(+) using the same Gibson assembly method. All plasmids were transformed into BL21 (DE3) Gold, and enzymes expressed in LB media with 50 μg/mL kanamycin. 1 L cultures were inoculated with 2 mL of a saturated culture in the same media, and grown to an $OD_{600}$ of 0.5-0.8 at 37° C. The cultures were induced with 1 mM IPTG, and expressed at 18° C. for 16 hours. The cells were harvested by centrifugation at 2,500×g, and resuspended in ~20 mL lysis buffer: 50 mM Tris [pH 8.0], 150 mM NaCl, and 10 mM imidazole. The cells were lysed using an Emulsiflex instrument. The lysate was clarified by centrifugation at 20,000×g, and the supernatant was batch bound to 1 mL NiNTA resin for 30 mins at 4° C. The resin was transferred to a gravity flow column. The resin was washed with 10 column volumes of wash buffer: 50 mM Tris [pH 8.0], 150 mM NaCl, and 10 mM imidazole. The protein was then eluted with 2 column volumes of elution buffer: 50 mM Tris [pH 8.0], 150 mM NaCl, 250 mM imidazole and 30% (v/v) glycerol. Enzymes were flash frozen in elution buffer using liquid $N_2$, and the enzyme stocks were stored at −80° C.

PDH Cell-free Reactions. The PDH reactions were assembled in two parts. First the co-factors and substrates were combined in one tube, and the enzymes were combined in another. The reactions were initiated by mixing the co-factors and enzymes in a final volume of 200 μL. The final substrate and co-factor concentrations were as follows: 500 mM glucose, 1 mM 1,6 fructose bisphosphate, 4 mM ATP, 0.5 mM 2,3 bisphosphoglycerate, 0.5 mM $NAD^+$, 1.5 mM CoA, 1.5 mM $NADP^+$, 0.5 mM TPP, 6 mM $MgCl_2$, 10 mM KCl, 50 mM Tris [pH 8.0] and 20 mM phosphate buffer [pH 8.0], 5 mM glutathione and 0.5-5 mM 1,6 DHN. The reactions were quenched at 24 hours.

PDH Activity Assays. PDH was assayed for activity in the presence of several aromatic polyketides. The vehicle control was 1% ethanol, and the activity was compared to an assay without the aromatic polyketides. The final reaction volume was 200 μL, and contained 2 mM $NAD^+$, 2 mM CoA, 1 mM TPP, 5 mM $MgCl_2$, 5 mM KCl, 50 mM Tris pH 8.0, and 5 μL of 1.25 mg/mL PDH. The reactions were set up in a 96-well plate. The aromatic polyketides were added to a final concentration of 1 mM and the ethanol control was added to a final concentration of 1% (v/v). The plate was incubated at room temperature for 10 minutes, and the reactions were initiated with 10 μL of 100 mM pyruvate. The absorbance at 340 nm was monitored for 10 minutes using an M200 spectrometer. Because the aromatic molecules had a background absorbance at 340 nm, the reactions were blanked using the reaction mixture and aromatic molecule, but instead of initiating the reaction with pyruvate, water was added. The initial rates were determined using the initial slope of a linear fit. The amount of NADH produced per unit time was calculated using Beer's law, and the extinction coefficient of $6.22\times10^3$ $M^{-1}cm^{-1}$. Reactions were performed in triplicate, and the average value and standard error were calculated.

PyOx/PTA Cell-free Reactions. The PyOx/PTA reactions were assembled in two pieces. First the co-factors and substrates were combined in one tube, and the enzymes were combined in another. The final co-factor and substrate concentrations in the 200 μL reaction were as follows: 500 mM glucose, 1 mM 1,6 fructose bisphosphate, 4 mM ATP, 0.5 mM 2,3 bisphosphoglycerate, 0.5 mM $NAD^+$, 1.5 mM CoA, 3 mM mM $NADP^+$, 0.5 mM TPP, 6 mM $MgCl_2$, 10 mM KCl, 50 mM Tris pH 8.0 and 50 mM phosphate buffer [pH 8.0]. The amount of enzyme added to each reaction is detailed in Table 3. The co-factors and enzymes were mixed to initiate the reaction, and a 500 μL nonane overlay was added to the top. The reactions were incubated at room temperature shaking gently on a gel shaker.

For 1,6 DHN/5-p-1,6 DHN: When the aromatic substrate was the varied component 0.5 to 5 mM of the aromatic substrate was added to the reaction, and the reactions were quenched at 24 hours. When time was the varied component, 5 mM of 1,6 DHN was added, and separate reactions were quenched at ~12, 24, 48 and 72 hours.

For olivetolate/CBGA: The optimization of the cannabinoid pathway showed that the same titers could be achieved with less glucose, so the glucose concentration was reduced to 150 mM. Additionally, increasing the NADP' concentration to 6 mM and decreasing the ATP concentration to 1 mM led to higher titers of CBGA. The olivetolate concentration was set at 5 mM. The amount of NphB added to the reaction was variable. The data shown in FIG. 2c utilized 1.5 mg/mL NphB, and the reactions were quenched at ~4, 8, 14, 24, 48, 72 and 96 hours. The data shown in FIG. 4a was achieved with 0.5 mg/mL of WT NphB and M23, and reactions were quenched at ~6, 9, 12, 24, 48, 72 and 96 hours.

For divarinic acid/CBGVA: The conditions were very similar to the general method above except 150 mM glucose, 1 mM ATP and 6 mM NADP' was used and the reactions were quenched at ~6, 9, 12, 24, and 48 hours. Additionally, the final concentration of the prenyl-transferase was 1 mg/mL, and we tested AtaPT, NovQ, and NphB with apigenin, daidzein, genistein, naringenin, and resveratrol. We also tested NphB with olivetol, olivetolate, and 1,6 DHN. The reactions were quenched at 24 h.

Quenching reactions. To quench the reactions, the aqueous and organic layer were transferred to a 1.5 mL microcentrifuge tube. The reaction vial was washed with 200 μL of ethyl acetate, which was then pooled with the reaction in the microcentrifuge tube. The samples were vortexed for 5-10 seconds and then centrifuged for 3 minutes at 13,000 rpm. The organic layer was removed, and the remaining aqueous layer was extracted 2 additional times with 200 μL of ethyl acetate. For each sample the organic extract was pooled, and then evaporated using a vacuum centrifuge. The samples were re-dissolved in methanol for HPLC analysis.

For olivetolate/CBGA: Due to the observed protein precipitation, the CBGA reactions shown in FIG. 4a were extracted in the presence of 0.12 g of urea (solid), to facilitate the extraction of CBGA. This was unnecessary for the WT NphB CBGA data in FIG. 2c because the proteins did not precipitate.

Quantification of products. The reactions were fractionated by reverse phase chromatography on a C18 column (4.6×100 mm) using a Thermo Ultimate 3000 HPLC. The column compartment temperature was set to 40° C., and the flow rate was 1 mL/min. The compounds were separated using a gradient elution with water +0.1% TFA (solvent A) and acetonitrile+0.1% TFA (solvent B) as the mobile phase. Solvent B was held at 20% for the first min. Then solvent B was increased to 95% B over 4 min, and 95% B was then held for 3 min. The column was then re-equilibrated to 20% B for three min, for a total run time of 11 min.

The cannabinoids (CBGA, CBDA, and CBDVA) were quantified using an external calibration curve derived from an analytical standard purchased from Sigma Aldrich. The 5-p-1,6-DHN and CBGVA nuclear magnetic resonance (NMR) samples were used to generate an external calibration curve because authentic standards were not available. A known concentration of the standard was dissolved in water, and then extracted using the method detailed above.

Quantify prenyl-products without authentic standards. Due to the lack of authentic standards for the prenyl-products prenyl-apigenin, prenyl-daidzein, prenyl-naringenin, prenyl-genistein, prenyl-resveratrol, and prenyl-olivetol, the prenyl-products were quantified based on substrate consumption. To generate a standard curve, serial dilutions of each aromatic substrate were subjected to the reaction mix, but to prevent product formation the prenyl-transferase was left out. Liquid chromatography-mass spectrometry was used to quantify the amount of substrate consumed by the reaction compared to the standard curve.

Electrospray ionisation time-of-flight measurements were carried out on a Waters LCT-Premier XE Time of Flight Instrument controlled by MassLynx 4.1 software (Waters Corporation, Milford, MA). The instrument was equipped with the Multi Mode Ionization source operated in the electrospray mode. A solution of Leucine Enkephalin (Sigma Chemical, L9133) was used in the Lock-Spray to obtain accurate mass measurements. Samples were infused using direct loop injection on a Waters Acquity UPLC system. Samples were separated on a Waters Acquity UPLC system using an Acquity BEH C18 1.7 μm column (50×2.1 mm) and were eluted with a gradient of 30-95% solvent B over 10 min (solvent A: water, solvent B: acetonitrile, both with 0.2% formic acid (vol/vol)). Mass spectra were recorded from a mass of 300-2000 Da.

NMR Spectroscopy. NMR spectroscopy was used to identify prenyl-products, and quantify 5-p-1,6-DHN.

For 1,6 DHN/5-p-1,6 DHN: The PyOx/PTA cell-free system was used to produce prenyl-DHN. 200 μL reactions were pooled, and extracted 3 times with an equivalent amount of nonane and then the nonane was evaporated. The product of the reactions was suspended in 500 μL of deuterated methanol ($CD_3OD$), with 2 mM 1,3,5-trimethoxybenzene (TMB) as an internal standard. Spectra were collected on an AV400 Bruker NMR spectrometer. The amount of the prenylated compound in the sample was determined with reference to the internal TMB standard. The proton signal from TMB (3H, s) at 6.05 ppm were compared with an aromatic proton corresponding to 5-p-1,6-DHN (1H, d) at 7.27 ppm.

For divarinic acid/CBGVA: NMR was also used to identify the product of the enzymatic system with divarinic acid as the aromatic substrate. The PyOx/PTA system was set up as detailed above, and the reactions were quenched at 24 hours. The reactions were extracted as detailed above, and analyzed on the HPLC. There was a new major peak at 6.7 minutes that was predicted to be the prenylated divarinic acid. The HPLC peak was purified, removed the solvent, and re-dissolved the pure component in 600 µL of CD$_3$OD. A proton spectrum collected with an AV500 Bruker NMR spectrometer was compared to a proton spectrum published by Shoyama et al. for CBGVA to confirm that CBGVA was the main product. Based on the paper by Shoyama et al the paper by Bohlman et al., it was concluded that the prenylation of divarinic acid occurs at the C3 carbon of divarinic acid.

Rosetta Design to modify the binding pocket of NphB to accept olivetolate. Olivetolate was placed in the active site of NphB in six different starting positions denoted as Olivetolate P1-6 in Table 4. ROSETTA was run 5 times for each olivetolate position for a total of 30 designs. The mutations predicted in each design are listed in Table 4. For each olivetolate position a consensus set of mutations (i.e., the most frequently chosen residue) was chosen to evaluate further: Consensus Group A through F (Table 4). The relative importance of each ROSSETTA suggested mutation was then evaluated. For each Consensus Group, the mutations were set back to WT residue, one at a time, and used ROSETTA to calculate the change in energy score (see Table 5). Those that caused the largest change in energy were deemed to be the most important mutants to include in the library for experimental testing.

TABLE 4

| | Olivetolate P1 | | | | | Consensus Mutations | Olivetolate P2 | | | | | Consensus Mutations | Olivetolate P3 | | | | | Consensus Mutations |
|---|---|---|---|---|---|---|---|---|---|---|---|---|---|---|---|---|---|---|
| Prediction # | 1 | 2 | 3 | 4 | 5 | Group A | 6 | 7 | 8 | 9 | 10 | Group B | 11 | 12 | 13 | 14 | 15 | Group C |
| V49 | I | T | I | I | I | I | T | S | S | S | T | S | N | | N | N | S | N |
| M162 | | | | | | | | | | | | | C | C | C | C | C | C |
| F213 | N | N | N | N | N | N | N | N | N | N | N | N | N | N | N | N | N | N |
| A232 | N | N | N | N | S | N | S | S | S | S | S | S | | | | | | |
| I234 | T | T | T | T | T | T | T | T | T | T | T | T | T | T | T | T | T | T |
| V271 | N | H | N | N | N | N | N | N | N | N | N | N | N | N | N | N | N | N |
| G286 | | | | | | | S | S | S | | S | S | S | | S | S | S | S |
| Y288 | A | D | A | A | H | A | N | N | N | N | N | N | S | A | S | S | N | S |
| L298 | I | I | I | I | I | I | R | R | R | R | R | R | R | R | R | R | R | R |
| Energy Score | | | | | | −404 | | | | | | −410 | | | | | | −405 |

| | Olivetolate P4 | | | | | Consensus Mutations | Olivetolate P5 | | | | | Consensus Mutations | Olivetolate P6 | | | | | Consensus Mutations |
|---|---|---|---|---|---|---|---|---|---|---|---|---|---|---|---|---|---|---|
| Prediction # | 16 | 17 | 18 | 19 | 20 | Group D | 21 | 22 | 23 | 24 | 25 | Group E | 26 | 27 | 28 | 29 | 30 | Group F |
| V49 | T | N | T | N | T | T | S | S | I | S | S | S | G | G | G | S | S | G |
| M162 | | | | | | | R | R | R | R | R | R | R | R | R | R | R | R |
| F213 | G | G | G | G | G | G | N | N | N | N | N | N | N | N | N | N | N | N |
| A232 | | | | | | | N | S | N | S | N | S | S | S | S | S | S | S |
| I234 | T | T | T | T | T | T | T | T | T | T | T | T | T | T | T | T | T | T |
| V271 | H | N | H | N | H | H | N | N | S | N | N | N | A | N | N | A | A | N |
| G286 | | | | | | | | | | | | | | | | | | |
| Y288 | D | S | N | S | D | N | N | N | N | N | N | N | N | N | N | A | A | N |
| L298 | I | I | I | I | I | I | I | A | N | A | N | A | G | V | V | G | G | V |
| Energy Score | | | | | | −402 | | | | | | −403 | | | | | | −398 |

TABLE 5

Olivetolate Position 1

| Amino Acid Position | Consensus Mutations Group A | WT | Energy Score of Mutant --> WT | Energy Difference |
|---|---|---|---|---|
| 49 | I | V | −403 | 1 |
| 213 | N | F | −391 | 13 |
| 232 | N | A | −401 | 3 |
| 234 | T | I | −382 | 22 |
| 271 | N | V | −395 | 9 |
| 288 | A | Y | −392 | 12 |
| 298 | I | L | −404 | 0 |
| Mutations with largest effect | | | | |
| I234T | | | | |
| F213N | | | | |
| Y288A | | | | |

Olivetolate Position 2

| Amino Acid Position | Consensus Mutations Group B | WT | Energy Score of Mutant --> WT | Energy Difference |
|---|---|---|---|---|
| 49 | S | V | −394 | 16 |
| 213 | N | F | −402 | 8 |
| 232 | S | A | −409 | 1 |
| 234 | T | I | −404 | 6 |
| 271 | N | V | −397 | 13 |
| 286 | S | G | −409 | 1 |
| 288 | N | Y | −401 | 9 |
| 298 | R | L | −408 | 2 |
| Mutations with largest effect | | | | |
| V49S | | | | |
| V271N | | | | |
| Y288N | | | | |

Olivetolate Position 3

| Amino Acid Position | Consensus Mutations Group C | WT | Energy Score of Mutant --> WT | Energy Difference |
|---|---|---|---|---|
| 49 | N | V | −391 | 14 |
| 162 | C | M | −404 | 1 |
| 213 | N | F | −390 | 15 |
| 234 | T | I | −400 | 5 |

TABLE 5-continued

| 271 | N | V | −396 | 9 |
|---|---|---|---|---|
| 286 | S | G | −404 | 1 |
| 288 | S | Y | −394 | 11 |
| 298 | R | L | −403 | 2 |

Mutations with largest effect
F213N
V49N
Y288S

Olivetolate Position 4

| Amino Acid Position | Consensus Mutations Group D | WT | Energy Score of Mutant --> WT | Energy Difference |
|---|---|---|---|---|
| 49 | T | V | −401 | 1 |
| 213 | G | F | −98 | 304 |
| 234 | T | I | −372 | 30 |
| 271 | H | V | −398 | 4 |
| 288 | N | Y | −381 | 21 |
| 298 | I | L | −401 | 1 |

Mutations with largest effect
F213G
I234T
Y288N

Olivetolate Position 5

| Amino Acid Position | Consensus Mutations Group E | WT | Energy Score of Mutant --> WT | Energy Difference |
|---|---|---|---|---|
| 49 | S | V | −398 | 5 |
| 162 | R | M | −402 | 1 |
| 213 | N | F | −318 | 85 |
| 232 | S | A | −327 | 76 |
| 234 | T | I | −398 | 5 |
| 271 | N | V | −391 | 12 |
| 288 | N | Y | −390 | 13 |
| 298 | A | L | −394 | 9 |

Mutations with largest effect
F213N
A232S
Y288N

Olivetolate Position 6

| Amino Acid Position | Consensus Mutations Group F | WT | Energy Score of Mutant --> WT | Energy Difference |
|---|---|---|---|---|
| 49 | G | V | −383 | 15 |
| 162 | R | M | −398 | 0 |
| 213 | N | F | −388 | 10 |
| 232 | S | A | −388 | 10 |
| 234 | T | I | −388 | 10 |
| 271 | N | V | −390 | 8 |
| 288 | N | Y | −367 | 31 |
| 298 | V | L | −397 | 1 |

Mutations with largest effect
Y288N
V49G

To model the olivetolic acid, the 4MX.sdf 3-D structure of olivetolate from the 5B09 crystal structure was used and hydrogen atoms were added to the structure assuming pH 7 using Open Babel 2.3.1. A rotamer library was generated for olivetolic acid using the Bio Chemical Library (BCL) molecule: Conformer Generator 3.5 using the PDB library. Finally, the aromatic bonds were manually annotated into the file before generating the parameter file read by Rosetta using the script main/source/python/public/molfile_to_params.py in the Rosetta 3.7 release. The parameter file for geranyl s-thioldiphosphate (GST) was generated without a rotamer library using the GST.sdf file from the 1ZB6 crystal structure. The olivetolic acid molecule was then manually placed into the co-crystal structure of NphB with GST and DHN (1ZB6) with the DHN and crystallographic waters removed using pymol. The olivetolic acid was placed in 6 different positions in the active site with the plane of the olivetolate aromatic ring parallel to the GST alkyl tail and the desired prenylation site 3.7 angstroms away from the eventual carbocation mirroring the placement of DHN in the 1ZB6 crystal structure. Residues 49, 162, 213, 224, 232, 233, 234, 271, 286, and 288 were allowed to be any amino acid during the Rosetta design with other sidechains held in a fixed position and the backbone fixed. The designed residues were in direct contact with the olivetolate and not in direct contact with GST. The fixed backbone script main/source/bin/fixbb.static.linuxgccrelease from the Rosetta 3.7 release was run with the all possible rotamers (−ex4), using the input sidechains (−use_input_sc), sidechains minimized after design (minimize_sidechains), the linear memnode interaction graph (−linmem_ig 10), and both with and without the ligand weighted score function (−score:weights ligand). From the identical starting point each design was run 5 times using the −nstruct input. From the set of mutations suggested by Rosetta, the mutations that occurred most frequently and contributed most to the Rosetta score function were chosen, creating a library of 22 mutants for experimental testing.

Initial NphB mutant library screening. For screening of the initial library, small scale expression and purifications were performed. 25 mL of LB media was inoculated with 25 uL of a saturated culture of BL21 DE3 Gold harboring the NphB expression plasmid. The cultures were incubated at 37° C. until the $OD_{600}$ reached 0.4-0.6. The expression of the NphB constructs were induced with the addition of 1 mM IPTG, followed by incubation for 18 hours at 18° C. Cells were harvested by centrifugation at 2500×g. The pellets were re-suspended in 500 μL of lysis buffer: 50 mM [Tris pH 8.0], 150 mM NaCl, and 5 mM imidazole and lysed by sonication. The cell lysate was clarified by centrifugation at 20,000×g for 10 minutes at 4° C., and the supernatant was incubated at 4° C. with 50 μL of NiNTA resin. A 96-well spin column plate was used to purify the NphB constructs. The supernatant/resin was applied to the column and centrifuged for 2 mins at 500×g. 500 μL of lysis buffer was then added, and the plate was centrifuged again for 1 minute at 500×g. The protein was eluted using 200 μL of elution buffer (50 mM Tris [pH 8.0], 150 mM NaCl, 250 mM imidazole and 30% (v/v) glycerol).

The enzymes were assayed under the following conditions: 2.5 mM geranyl pyrophosphate, 5 mM olivetolate, 5 mM $MgCl_2$, 50 mM Tris pH 8.0, ~0.1 mg/mL NphB mutant in a final volume of 100 μL. All enzymes were first diluted to 0.5 mg/mL using elution buffer so the final concentration of imidazole was the same in each reaction. The reactions were incubated for 12 hours at room temperature, then extracted 3 times with 100 μL of ethyl acetate. The organic extract was pooled for each reaction and the solvent was removed using a vacuum centrifuge. The samples were redissolved in 100 μL of methanol and subjected to HPLC analysis.

Focused NphB mutant library screening. For the focused library, 1 L scale expression and purification of the NphB constructs as described above was performed. The enzymes were assayed under the following conditions: 2.5 mM GPP, 5 mM olivetolate, 5 mM $MgCl_2$, 50 mM Tris pH 8.0 and ~1 mg/mL of NphB enzyme in a final volume of 100 μL. The reactions were incubated at room temperature for 1 hour. 40 μL of each reaction was quenched in 80 μL of acetonitrile. The samples were centrifuged for 5 minutes at 13,000 rpm, to remove precipitated proteins. The supernatant was analyzed using HPLC as described above.

Enzyme Kinetic Parameters. The reactions were set up under the following conditions: 50 mM Tris [pH 8.0], 2.5 mM GPP, 5 mM MgCl$_2$, ~27 μM enzyme, and olivetolate or divarinic acid was varied from 0.1 mM to 6 mM in a final volume of 200 μL. 40 μL of the reaction was quenched in 80 μl acetonitrile+0.1% TFA, at the time intervals detailed below. The reactions were centrifuged for 5 minutes at 13,000-16,060×g to pellet the protein, and the supernatant was analyzed using the HPLC method detailed above. The initial rate was plotted vs the concentration of substrate, and fit with the Michaelis-Menten equation to determine the kinetic parameters $k_{cat}$ and $K_M$ (OriginPro). Each Michaelis-Menten curve was performed in triplicate. The average and standard deviation of the kinetic parameters are reported.

For olivetolate/CBGA: For WT, M1, M10 and M30 the time course was 3, 6, 9, and 12 minutes. For mutant 25 the reactions were quenched at 1, 2, 4 and 8 minutes, and for M31 the reactions were quenched at 1, 2, 4 and 6 minutes.

For divarinic acid/CBGVA: For M31, the time course was 0.5, 1, 1.5 and 2 minutes. For M23, the time course was 5, 10, 15 and 20 minutes, and for WT NphB the time course was 8, 16, 24 and 32 minutes. The enzyme concentration for the mutants was ~27 μM, and the concentration of WT NphB was ~35 μM.

GC-MS characterization of isomer profile from WT NphB and M23. Samples were dissolved in 200 μL of ethyl acetate. GC-MS measurements were carried out using an Agilent Model 7693 Autosampler, 7890B Gas Chromatograph, and 7250 Q-TOF Mass Selective Detector in the Electron Ionization mode. Sample injection was carried out in split mode with inlet temperature set to 280° C. Separation was carried out on an Agilent HP5-MS column with dimensions 30 m×250 μm×0.25 μm. Ultra High Purity Grade He (Airgas) was used as carrier gas with the flow set to 1.1 mL/min in constant flow mode. The initial oven temperature was set to 120° C. for 1 min followed by a 20° C./min ramp to a final temperature of 300° C. which was maintained for 4 min. A 3.0 min solvent delay was used. EI energy was set to 15 eV. The MSD was set to scan the 50-500 m/z range. Data collection and analysis were performed using Mass Hunter Acquisition and Qualitative Analysis software (Agilent).

Due to the increased temperature of the GC inlet, CBGA undergoes spontaneous decarboxylation as described by Radwan et al, resulting in an M+ ion at 316 m/z. The retention time corresponding to the 316 m/z ion for the CBGA standard was 10.48 minutes.

Nonane-flow system for the extraction of CBGA from solution. A PyOx/PTA reaction was set up as detailed above. A 500 μL nonane overlay was added to the reaction in a 2 ml glass vial which was covered with 2 layers of breathable cell culture film. 2 needles were inserted into a 15 mL falcon tube at the ~750 μL mark and the 3.5 mL mark. Luer locks to tubing connectors were connected to the needles and Viton tubing was connected to the other end of the luer lock. Needles were connected to the other end of the tubing via a luer lock connector and inserted through the mesh covering so they were only touching the nonane layer and not the reaction. 2 mL of Tris buffer [pH 8.5] was added to the 15 mL conical tube, and 6 mL of nonane was added. The nonane was pumped through the system using a peristaltic pump such that the nonane flowed from the top of the reaction, through the buffered solution. The nonane pumped into the reservoir separated into the top layer of the 15 mL conical tube. The nonane from the top of the 15 mL conical tube was pumped into the top of the reaction vial. This essentially diluted the CBGA throughout the system driving the diffusion of CBGA into the nonane layer and out of the reaction.

Cloning CBDAS. A gene block of CBDAS was ordered from IDT codon optimized for *Pichia pastoris*. The signal sequence was removed by PCR amplifying from the 28$^{th}$ residue of the protein sequence (NPREN . . . ) through the end of the protein, with overhangs compatible with the pPICZα vector. The PCR product was cloned into the pPICZα vector digested with EcoRI and XbaI using the Gibson cloning method. The product of the assembly reaction was transformed into BL21 Gold (DE3) cells a clone with the correct sequence isolated. The plasmid was digested with PmeI for 2 hours, and then purified using the Qiagen PCR purification protocol. The plasmid was transformed into *Pichia pastoris* X33 using electroporation. Immediately following electroporation, the cells were incubated in 1 mL of cold 1 M sorbitol and 1 mL of YPD media without shaking for 2 hours. The cells were plated on YPDS plates with 500 μg/mL of zeocin. Colonies were screened using PCR for the presence of the CBDAS gene between the AOX1 promoter and terminator. For screening, the colonies were re-suspended in 15 μL of sterile water and 5 μL of the resuspended colony was transferred into a PCR tube with 0.2% SDS. The samples were heated for 10 minutes at 99° C., and then 1 μL was used as the template for PCR. Six colonies with positive colony PCR hits were screened for the expression of CBDAS.

CBDAS Expression Test. The six colonies were grown overnight at 30° C. to obtain a saturated culture. The overnight cultures were used to inoculate a 25 mL culture in BMGY media and grown to an OD of ~2. The cells were harvested by centrifugation at 2,000×g for 10 minutes. The cell pellet was re-suspended in 90 mL of BMMY media, and incubated at 30° C. for 5 days. Each day, 1 mL of the culture was removed for SDS-PAGE analysis, and 500 μL of methanol was added. On day 3 the cultures were screened for CBDAS activity. The assay conditions were as follows: 100 μL of 200 mM citrate buffer, 100 μM CBGA, 5 mM MgCl$_2$, 5 mM KCl, 1 mM FAD and 50 μL of the expression media in a final volume of 200 μL. The reactions were incubated overnight at room temperature and then extracted 3 times with 200 μL of ethyl acetate. The ethyl acetate extractions were pooled for each sample, and removed using a vacuum centrifuge. The samples were re-suspended in 200 μL of methanol and analyzed by HPLC. All clones produced active CBDAS.

The culture from three clones (~300 mL total), was collected to obtain CBDAS activity. The cells were pelleted by centrifuging at ~3,000×g for 20 minutes at 4° C. Then the supernatant was passed through a 0.22 μm filter. The media was concentrated and buffer exchanged into 100 mM citrate buffer pH 5.0 using a 50,000 MWCO protein concentrator from Millipore. The total protein in the media concentrate was determined to be 0.4 mg/mL using a Bradford assay, for a total yield of ~5 mg/L total protein.

Production of CBDVA and CBDA. To convert the precursors CBGA and CBGVA into CBDA and CBGVA respectively, a secondary reaction was set up with CBDAS synthase.

For CBGA/CBDA: A PyOx/PTA enzymatic system was set up as detailed above to produce CBGA. After 24 hours 200 μL of the nonane overlay from the CBGA reaction was transferred to a CBDAS reaction vessel. In the aqueous layer: 50 mM Hepes [pH 7.0], 5 mM MgCl$_2$, 5 mM KCl, 25 μM FAD, 0.1 mg/mL CBDAS concentrate. The reaction was incubated at 30° C. with gentle shaking. Reactions were quenched at 12, 24, 48, 72 and 96 hours.

For CBGVA/CBDVA: HPLC purified CBGVA was converted to CBDVA. The final reaction volume was 200 μL, with 50 mM Hepes [pH 7.0], 5 mM MgCl$_2$, 5 mM KCl, 25 μM FAD and 0.1 mg/mL (total protein) of CBDAS concentrate. A 200 μL nonane overlay was added, and the reactions were incubated at 30° C. with gentle shaking. The reactions were quenched at ~24, 48, 72 and 96 hours.

MatB Activity Assay. A coupled enzymatic assay was used to determine the activity of malonyl-CoA synthetase (MatB) from R. palustris (see, e.g., SEQ ID NO:82-83) in the presence of OA and DA. The reaction conditions were: 2.5 mM malonate, 2 mM ATP, 1 mM CoA, 2.5 mM phosphoenolpyruvate (PEP), 1 mM NADH, 5 mM MgCl$_2$, 10 mM KCl, 0.35 mg/mL ADK, 0.75 μg/mL MatB, 1.6 units of PK and 2.5 units of LDH, and 50 mM Tris [pH 8.0]. Background ATPase activity was controlled for by leaving out the substrate (malonate), and either 1% ethanol, 250 μM or 5 mM OA or 5 mM DA was added to the remaining reactions. The activity of MatB was determined by monitoring decreasing absorbance at 340 nm due to NADH consumption using an M2 SpectraMax. To ensure that MatB was limiting at 5 mM OA or DA, MatB was doubled to 1.5 μg/mL. The rate of the reaction doubled suggesting that MatB was the limiting component in the system. The rate of NADH consumption at 5 mM OA and 5 mM DA was normalized to the 1% ethanol control.

AAE3 Activity Assay. A coupled enzymatic assay, similar to the one above was used to determine the activity of acyl activating enzyme 3 (AAE3) (see, e.g., SEQ ID NOs: 70-71 and homologs—SEQ ID NO:72-75) in the presence of OA and DA. The conditions were the same as the MatB assay with the following modifications: 2.5 mM hexanoate was added in lieu of malonate, and 15 μg/mL of AAE3 was added in lieu of MatB. To ensure that AAE3 was limiting, AAE3 was doubled in the presence of 5 mM OA or DA. The rate of the reaction doubled indicating AAE3 is limiting.

ADK Activity Assay. A coupled enzymatic assay was used to determine the activity of adenylate kinase (ADK)(see, e.g., SEQ ID NO: in the presence of OA and DA. The conditions were similar to the MatB assay, with the following modifications: 2 mM AMP was added in lieu of malonate, CoA was not added, and 0.001 mg/mL of ADK was added. To ensure that ADK was the limiting reagent at 5 mM OA and DA, the amount of ADK was doubled. The 2-fold increase in rate suggested that ADK was the limiting factor.

CPK Activity Assay. A coupled enzymatic assay was used to determine the activity of creatine kinase (CPK) in the presence of OA or DA. The reaction conditions were: 5 mM Creatine Phosphate, 2 mM ADP, 5 mM glucose, 2 mM NADP', 5 mM MgCl$_2$, 5 mM KCl, 0.3 mg/mL Zwf, 0.1 mg/mL Sc Hex and 0.08 units CPK. The positive control reaction contained 1% ethanol, and either 5 mM of OA or DA was added to the remaining reactions. The absorbance of NADPH at 340 nm was monitored. To ensure that CPK was limiting was doubled at 5 mM OA and 5 mM DA. The resulting rate doubled, which indicates CPK is limiting even at high OA and DA.

OLS Activity Assay. Olivetol synthase (OLS)(see, e.g., SEQ ID NO:76-77) was assayed by setting up the following conditions: 200 μM malonyl CoA, 100 μM hexanoyl-CoA, 0.65 mg/mL OAS, in either 50 mM citrate buffer pH 5.5 or 50 mM Tris buffer pH 8.0. The reactions were initiated by the addition of OAS, and then they were quenched at 30 minutes by adding 150 μL of methanol to the 50 μL reaction. The samples were centrifuged at ~16,000×g for 2 minutes to pellet the proteins. The supernatant was analyzed using the HPLC.

For the inhibition experiments the conditions were altered to: 1 mM malonyl-CoA, 400 μM hexanoyl-CoA in 50 mM citrate buffer, pH 5.5 in a final volume of 200 μL. Either 1% ethanol, 250 μM OA or 1 mM DA was added to the reaction, and then the reactions were initiated by adding 0.65 mg/mL OLS. 50 μL aliquots were quenched at 2, 4, 6 and 8 minutes in 150 μL of methanol. The reactions were vortexed briefly and centrifuged at 16,000×g for 2 minutes to pellet the proteins. The supernatant was analyzed by HPLC. The raw peak areas of HTAL, PDAL and olivetol were summed and plotted against time to determine the rate. The rate of the OA supplemented reaction and the DA supplemented reaction were normalized to the ethanol control.

OLS/OAC Activity Assay. To produce OA, the same OLS conditions specified above were used, but olivetolic acid cyclase (OAC)(see, e.g., SEQ ID NO:78-79) was added to the reaction at 0.6 mg/mL. The reactions were quenched and analyzed in the same manner as the OLS assay. Acetyl-phosphate and BSA were added to the assays individually 5 mM-40 mM AcP and 10-30 mg/mL BSA final concentration.

Full pathway set up. The enzymes used in this study and the final concentration (mg/mL) can be found in Table 6 for the MatB path and Table 7 for the MdcA path. For the MatB path, the cofactors were added at the following concentrations: 150 mM glucose, 1 mM fructose bisphosphate, 2 mM ATP, 0.25 mM NAD+, 3 mM NADP+, 2 mM CoA, 0.25 mM 2,3-bisphosphoglycerate, 6 mM MgCl2, 10 mM KCl, 0.5 mM thiamine pyrophosphate, 50 mM phosphate pH 8.0, 5 mM hexanoate, 15 mM malonate, 5 mM creatine phosphate, and 50 mM Tris, pH 8.0. The reactions were initiated by the addition of the enzymes listed in Table 6. The reaction was incubated overnight at room temperature, and the reaction was quenched and extracted 3 times with 200 μL of ethyl acetate. The ethyl acetate was removed using a vacuum centrifuge. The sample was dissolved in 200 μL of methanol and analyzed using HPLC.

TABLE 6

Enzymes used in the full cannabinoid MatB pathway, with final enzyme concentrations
MatB Pathway

| Enzyme | mg/mL |
|---|---|
| Glycolysis | |
| Sc Hex | 0.02 |
| Gs PfkA | 0.32 |
| Sa Fba | 0.18 |
| Gs TpiA | 0.04 |
| Gs Pgi | 0.17 |
| Ec GapA | 0.05 |
| Gs GapM6 | 0.18 |
| Gs Pgk | 0.03 |
| Ec dPgm | 0.38 |
| Ec Eno | 0.08 |
| Ec PykF | 0.56 |
| Av PyOx | 1 unit |
| Gs PTA | 0.06 |
| Ll NoxE | 0.25 |
| Ca Catalase | 125 units |
| Mevalonate | |
| Re PhaA | 0.12 |
| Ef HMGS A110G | 0.22 |
| Ef HMGR | 0.58 |
| Mm MVK | 0.16 |
| Spne PMVK | 0.23 |

TABLE 6-continued

Enzymes used in the full cannabinoid MatB pathway, with final enzyme concentrations
MatB Pathway

| Enzyme | mg/mL |
|---|---|
| Spne MDC | 0.22 |
| Ec IDI | 0.23 |
| Gs FPPS S82F | 0.04 |
| SCL190 NphB | 0.45 |
| Gs Ppase | 0.16 |
| Olivetolate | |
| Rp MatB | 0.03 |
| Cs AAE3 | 0.18 |
| Cs OLS | 0.25 |
| Cs OAC | 0.87 |
| Gt ADK | 0.07 |
| Creatine Kinase | 2 units |

TABLE 7

Enzymes used in the full cannabinoid MdcA pathway with final enzyme concentrations
Transferase Pathway

| Enzyme | mg/mL |
|---|---|
| Glycolysis | |
| Sc Hex | 0.02 |
| Gs PfkA | 0.32 |
| Sa Fba | 0.18 |
| Gs TpiA | 0.04 |
| Gs Pgi | 0.17 |
| Ec GapDH | 0.05 |
| Gs GapM6 | 0.18 |
| Gs Pgk | 0.03 |
| Ttg dPgm | 0.09 |
| Ec EnoNH | 0.08 |
| Gs PykA | 0.13 |
| Av PyOx | 1 unit |

TABLE 7-continued

Enzymes used in the full cannabinoid MdcA pathway with final enzyme concentrations
Transferase Pathway

| Enzyme | mg/mL |
|---|---|
| Gs PTA | 0.06 |
| Ll NoxE | 0.25 |
| Ca Catalase | 125 units |
| Mevalonate | |
| Re PhaA | 0.12 |
| Ef HMGS-A110G | 0.43 |
| Ef HMGR | 0.58 |
| Mm MVK | 0.16 |
| Spne PMVK | 0.23 |
| Spne MDC | 0.19 |
| Ec IDI-CH | 0.23 |
| Gs FPPS S82F | 0.04 |
| SCL190 NphB31 | 0.68 |
| Gs PPase | 0.16 |
| Olivetolate | |
| Gs MdcA | 0.18 |
| Cs AAE3 | 0.12 |
| Cs OAS | 0.60 |
| Cs OAC | 0.87 |
| Gt ADK | 0.07 |
| Creatine Kinase | 2 units |

The enzymes for the MdcA path can be found in Table 7. The MdcA reaction was set up under the same cofactor conditions specified above with the following changes: 3 mM ATP, 0.25 mM AMP, 25 mM creatine phosphate and no Tris buffer.

The pathway of both the MatB and MdcA pathway are provided in FIG. 5A-B.

Certain embodiments of the invention have been described. It will be understood that various modifications may be made without departing from the spirit and scope of the invention. Other embodiments are within the scope of the following claims.

What is claimed is:

1. A recombinant, artificial, or engineered metabolic pathway, comprising:
   (i) conversion of pyruvate to acetyl phosphate;
   (ii) conversion of acetyl phosphate to acetyl-coA;
   (iii) a first cofactor-dependent enzyme that converts glyceraldehyde-3-phosphate to 1,3,-bisphosphoglycerate;
   (iv) a second cofactor-dependent enzyme that converts glyceraldehyde-3-phosphate to 1,3,-biphosphoglycerate, wherein the second cofactor-dependent enzyme is mutated to have its cofactor preference altered, wherein the second cofactor-dependent enzyme has dehydrogenase activity and uses NADP+ as a cofactor, and wherein the second cofactor-dependent enzymes has the sequence of SEQ ID NO:37, but has (1) a P191D mutation or (2) D34A/L35R/T36K mutations;
   (v) an enzyme that recycles a cofactor, wherein the cofactor is selected from the group consisting of NAD+/NADH, NADP+/NADPH, and FAD+/FADH; and
   (vi) a polypeptide that has prenyltransferase activity, wherein the polypeptide has a sequence that is at least 95% identical to SEQ ID NO:30 and has mutations selected from the group consisting of: Y228N; Y288A and F213H; Y288N and V49S; Y288S and V49N; Y288A and V49S; Y288N and G286S; Y288A, F213N and A232S; Y288N, F213G, V49T and V271H; Y288A and G286S; Y288A, G286S and A232S; Y288A, G286S, A232S and F213H; Y288V and G286S; Y288A and A232S; and Y288V and A232S.

2. The recombinant, artificial, or engineered metabolic pathway of claim 1, wherein the recombinant, artificial, or engineered metabolic pathway is in a cell-free system.

3. The recombinant, artificial, or engineered metabolic pathway of claim 1, wherein the first cofactor-dependent enzyme comprises dehydrogenase activity using NAD+ as the cofactor.

4. The recombinant, artificial, or engineered metabolic pathway of claim 1, wherein the enzyme that recycles the cofactor is an NAD (P) H oxidase.

5. The recombinant, artificial, or engineered metabolic pathway of claim 1, wherein the recombinant, artificial, or engineered metabolic pathway comprises one or more of the following enzymes:
   (i) hexokinase (Hex);
   (ii) Glucose-6-phosphate isomerase (Pgi);
   (iii) Phosphofructokinase (Pfk);
   (iv) Fructose-1,6-bisphosphate aldolase (Fba);
   (v) Triose phosphate isomerase (Tpi);
   (vi) Gald-3-P dehydrogenase (Gap);
   (vii) a mutant Gald-3-P dehydrogenase (mGap);
   (viii) NADH Oxidase (Nox)
   (ix) Phosphoglycerate Kinase (Pgk)
   (x) Phosphoglycerate Mutase (2,3 BPG dependent or Mn2+dependent) (dPgm or iPgm);
   (xi) Enolase (eno);
   (xii) Pyruvate Kinase (FBP dependent/pykF or AMP dependent/pykA);
   (xiii) Pyruvate Oxidase (PyOx);
   (xiv) Acetyl-phosphate transferase (PTA);
   (xv) Acetyl-CoA acetyltransferase (PhaA);
   (xvi) HMG-COA Synthase (HMGS);
   (xvii) HMG-COA Reductase (HMGR);
   (xviii) Mevalonate Kinase (MVK);
   (xix) Phosphomevalonate Kinase (PMVK);
   (xx) Diphosphomevalonate decarboxylase (MDC); and
   (xxi) Geranyl-PP synthase (GPPS) or Farnesyl-PP synthease mutant S82F.

6. The recombinant, artificial, or engineered metabolic pathway of claim 1, wherein the polypeptide having prenyltransferase activity converts 1-geranyl pyrophosphate to a prenyl-compound when a suitable substrate is present.

7. The recombinant, artificial, or engineered metabolic pathway of claim 6, wherein the suitable substrate is selected from the group consisting of apigenin, olivetolic acid, divarinic acid, resveratrol, and 2,4-dihydroxybenzoic acid or a derivative thereof.

8. The recombinant, artificial, or engineered metabolic pathway of claim 6, wherein the prenyl-compound is a cannabinoid.

9. A recombinant, artificial, or engineered metabolic pathway, comprising:
   (i) conversion of pyruvate to acetyl phosphate;
   (ii) conversion of acetyl phosphate to acetyl-coA;
   (iii) a first cofactor-dependent enzyme that converts glyceraldehyde-3-phosphate to 1,3,-bisphosphoglycerate;
   (iv) a second cofactor-dependent enzyme that converts glyceraldehyde-3-phosphate to 1,3,-biphosphoglycerate, wherein the second cofactor-dependent enzyme is mutated to have its cofactor preference altered;
   (v) an enzyme that recycles a cofactor, wherein the cofactor is selected from the group consisting of NAD+/NADH, NADP+/NADPH, and FAD+/FADH; and
   (vi) a polypeptide that has prenyltransferase activity, wherein the polypeptide has a sequence that is at least 95% identical to SEQ ID NO:30 and has mutations selected from the group consisting of: Y228N; Y288A and F213H; Y288N and V49S; Y288S and V49N; Y288A and V49S; Y288N and G286S; Y288A, F213N and A232S; Y288N, F213G, V49T and V271H; Y288A and G286S; Y288A, G286S and A232S; Y288A, G286S, A232S and F213H; Y288V and G286S; Y288A and A232S; and Y288V and A232S; wherein the recombinant, artificial, or engineered metabolic pathway is in a cell-free system.

10. The recombinant, artificial, or engineered metabolic pathway of claim 9, wherein the pathway is contacted with a suitable substrate is selected from the group consisting of apigenin, olivetolic acid, divarinic acid, resveratrol, and 2,4-dihydroxybenzoic acid or a derivative thereof.

11. The recombinant, artificial, or engineered metabolic pathway of claim 10, wherein the derivative of 2,4-dihydroxy benzoic acid is a compound of Formula I:

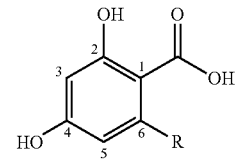

wherein R is H, $CH_3$, or X, wherein X is selected from a halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_{10})$alkyl, an optionally substituted $(C_2-C_{10})$alkenyl, an optionally substituted $(C_2-C_{10})$alkynyl, an optionally substituted $(C_1-C_{10})$ hetero-alkyl, an optionally substituted $(C_2-C_{10})$ hetero-alkenyl, an optionally substituted $(C_2-C_{10})$ hetero-alkynyl, an optionally substituted $(C_3-C_{10})$ cycloalkyl, an optionally substituted aryl, and an optionally substituted heterocycle.

12. The recombinant, artificial, or engineered metabolic pathway of claim 9, wherein the polypeptide having prenyltransferase activity converts 1-geranyl pyrophosphate to a prenyl-compound selected from a cannabinoid, a flavonoid, or a stilbenoid in the presence of a suitable substrate.

13. The recombinant, artificial, or engineered metabolic pathway of claim 12, wherein the suitable substrate is olivetolate and the prenyl-compound is cannabigerolic acid (CBGA), wherein the suitable substrate is divarinic acid and the prenyl-compound is cannabigerovarinic acid (CBGVA), or the suitable substrate is 2,4-dihydroxybenzoic acid or a derivative thereof and the prenyl-compound is CBGXA, wherein X is selected from a halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_{10})$alkyl, an optionally substituted $(C_2-C_{10})$alkenyl, an optionally substituted $(C_2-C_{10})$alkynyl, an optionally substituted $(C_1-C_{10})$ hetero-alkyl, an optionally substituted $(C_2-C_{10})$ hetero-alkenyl, an optionally substituted $(C_2-C_{10})$ hetero-alkynyl, an optionally substituted $(C_3-C_{10})$ cycloalkyl, an optionally substituted aryl, and an optionally substituted heterocycle.

14. A recombinant, artificial, or engineered metabolic pathway, comprising:
   (i) an enzyme that converts pyruvate to acetyl phosphate;
   (ii) an enzyme that converts acetyl phosphate to acetyl-coA;
   (iii) a first cofactor-dependent enzyme that converts glyceraldehyde-3-phosphate to 1,3,-bisphosphoglycerate;

(iv) a second cofactor-dependent enzyme that converts glyceraldehyde-3-phosphate to 1,3,-biphosphoglycerate, wherein the second cofactor-dependent enzyme is mutated to have its cofactor preference altered;

(v) an enzyme that recycles a cofactor, wherein the cofactor is selected from the group consisting of NAD+/NADH, NADP+/NADPH, and FAD+/FADH; and (vi) a polypeptide that has prenyltransferase activity, wherein the polypeptide has a sequence that is at least 95% identical to SEQ ID NO:30 and has mutations selected from the group consisting of: Y228N; Y288A and F213H; Y288N and V49S; Y288S and V49N; Y288A and V49S; Y288N and G286S; Y288A, F213N and A232S; Y288N, F213G, V49T and V271H; Y288A and G286S; Y288A, G286S and A232S; Y288A, G286S, A232S and F213H; Y288V and G286S; Y288A and A232S; and Y288V and A232S and convert 1-geranyl pyrophosphate to a prenyl-compound when a suitable substrate is present; wherein the suitable substrate is selected from the group consisting of olivetolic acid, divarinic acid, and 2,4-dihydroxybenzoic acid or a derivative thereof; wherein the recombinant, artificial, or engineered metabolic pathway is in a cell-free system.

15. The recombinant, artificial, or engineered metabolic pathway of claim 14, wherein the suitable substrate is olivetolate and the prenyl-compound is cannabigerolic acid (CBGA), wherein the suitable substrate is divarinic acid and the prenyl-compound is cannabigerovarinic acid (CBGVA), or the suitable substrate is 2,4-dihydroxybenzoic acid or a derivative thereof and the prenyl-compound is CBGXA, wherein X is selected from a halo, hydroxyl, cyano, nitro, ester, alkoxy, amino, thiol, sulfinyl, sulfonyl, sulfino, sulfo, thiocyanato, isothiocyanato, thial, borono, boronate, phosphate, aldehyde, carboxyl, carboxamido, azido, cyanato, isocyanato, an optionally substituted $(C_1-C_{10})$alkyl, an optionally substituted $(C_2-C_{10})$alkenyl, an optionally substituted $(C_2-C_{10})$alkynyl, an optionally substituted $(C_1-C_{10})$ hetero-alkyl, an optionally substituted $(C_2-C_{10})$ hetero-alkenyl, an optionally substituted $(C_2-C_{10})$ hetero-alkynyl, an optionally substituted $(C_3-C_{10})$ cycloalkyl, an optionally substituted aryl, and an optionally substituted heterocycle.

* * * * *

SEQUENCE LISTING

```
Sequence total quantity: 85
SEQ ID NO: 1            moltype = AA  length = 327
FEATURE                 Location/Qualifiers
source                  1..327
                        mol_type = protein
                        organism = synthetic construct
SEQUENCE: 1
MGSSHHHHHH SSGLVPRGSH MSEAADVERV YAAMEEAAGL GVACARDKI  YPLLSTFQDT   60
LVEGGSVVVF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSFSVYPTLN  240
WETGKIDRLC FAVISNDPTL VPSSDEGDIE KFHNYATKAP YAYVGEKRTL VYGLTLSPKE  300
EYYKLGAAYH ITDVQRGLLK AFDSLED                                    327

SEQ ID NO: 2            moltype = AA  length = 327
FEATURE                 Location/Qualifiers
source                  1..327
                        mol_type = protein
                        organism = synthetic construct
SEQUENCE: 2
MGSSHHHHHH SSGLVPRGSH MSEAADVERV YAAMEEAAGL GVACARDKI  YPLLSTFQDT   60
LVEGGSVVVF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSFSVYPTLN  240
WETGKIDRLC FAVISNDPTL VPSSDEGDIE KFHNYATKAP YAYVGEKRTL VYGLTLSPKE  300
EYYKLGANYH ITDVQRGLLK AFDSLED                                    327

SEQ ID NO: 3            moltype = AA  length = 327
FEATURE                 Location/Qualifiers
```

```
source                  1..327
                        mol_type = protein
                        organism = synthetic construct
SEQUENCE: 3
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSHSVYPTLN   240
WETGKIDRLC FAVISNDPTL VPSSDEGDIE KFHNYATKAP YAYVGEKRTL VYGLTLSPKE   300
EYYKLGAAYH ITDVQRGLLK AFDSLED                                      327

SEQ ID NO: 4           moltype = AA  length = 327
FEATURE                Location/Qualifiers
source                  1..327
                        mol_type = protein
                        organism = synthetic construct
SEQUENCE: 4
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSNSVYPTLN   240
WETGKIDRLC FAVISNDPTL VPSSDEGDIE KFHNYATKAP YAYVGEKRTL VYGLTLSPKE   300
EYYKLGAAYH ITDVQRGLLK AFDSLED                                      327

SEQ ID NO: 5           moltype = AA  length = 327
FEATURE                Location/Qualifiers
source                  1..327
                        mol_type = protein
                        organism = synthetic construct
SEQUENCE: 5
MGSSHHHHHH SSGLVPRGSH MSEAADVERV YAAMEEAAGL LGVACARDKI YPLLSTFQDT    60
LVEGGSVVSF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FAVISNDPTL VPSSDEGDIE KFHNYATKAP YAYVGEKRTL VYGLTLSPKE   300
EYYKLGANYH ITDVQRGLLK AFDSLED                                      327

SEQ ID NO: 6           moltype = AA  length = 327
FEATURE                Location/Qualifiers
source                  1..327
                        mol_type = protein
                        organism = synthetic construct
SEQUENCE: 6
MGSSHHHHHH SSGLVPRGSH MSEAADVERV YAAMEEAAGL LGVACARDKI YPLLSTFQDT    60
LVEGGSVVNF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FAVISNDPTL VPSSDEGDIE KFHNYATKAP YAYVGEKRTL VYGLTLSPKE   300
EYYKLGASYH ITDVQRGLLK AFDSLED                                      327

SEQ ID NO: 7           moltype = AA  length = 327
FEATURE                Location/Qualifiers
source                  1..327
                        mol_type = protein
                        organism = synthetic construct
SEQUENCE: 7
MGSSHHHHHH SSGLVPRGSH MSEAADVERV YAAMEEAAGL LGVACARDKI YPLLSTFQDT    60
LVEGGSVVSF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FAVISNDPTL VPSSDEGDIE KFHNYATKAP YAYVGEKRTL VYGLTLSPKE   300
EYYKLGAAYH ITDVQRGLLK AFDSLED                                      327

SEQ ID NO: 8           moltype = AA  length = 327
FEATURE                Location/Qualifiers
source                  1..327
                        mol_type = protein
                        organism = synthetic construct
SEQUENCE: 8
MGSSHHHHHH SSGLVPRGSH MSEAADVERV YAAMEEAAGL LGVACARDKI YPLLSTFQDT    60
LVEGGSVVTF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FAVISNDPTL VPSSDEGDIE KFHNYATKAP YAYVGEKRTL VYGLTLSPKE   300
EYYKLGANYH ITDVQRGLLK AFDSLED                                      327

SEQ ID NO: 9           moltype = AA  length = 327
FEATURE                Location/Qualifiers
source                  1..327
```

```
                              mol_type = protein
                              organism = synthetic construct
SEQUENCE: 9
MGSSHHHHHH SSGLVPRGSH MSEAADVERV YAAMEEAAGL LGVACARDKI YPLLSTFQDT      60
LVEGGSVVVF SMASGRHSTE LDFSISVPTS HGDPYATVVE KGLFPATGHP VDDLLADTQK     120
HLPVSMFAID GEVTGGFKKT YAFFPTDNMP GVAELSAIPS MPPAVAENAE LFARYGLDKV     180
QMTSMDYKKR QVNLYFSELS AQTLEAESVL ALVRELGLHV PNELGLKFCK RSFSVYPTLN     240
WETGKIDRLC FAVTSNDPTL VPSSDEGDIE KFHNYATKAP YAYVGEKRTL VYGLTLSPKE     300
EYYKLGANYH ITDVQRGLLK AFDSLED                                        327

SEQ ID NO: 10         moltype = AA   length = 327
FEATURE               Location/Qualifiers
source                1..327
                      mol_type = protein
                      organism = synthetic construct
SEQUENCE: 10
MGSSHHHHHH SSGLVPRGSH MSEAADVERV YAAMEEAAGL LGVACARDKI YPLLSTFQDT      60
LVEGGSVVVF SMASGRHSTE LDFSISVPTS HGDPYATVVE KGLFPATGHP VDDLLADTQK     120
HLPVSMFAID GEVTGGFKKT YAFFPTDNMP GVAELSAIPS MPPAVAENAE LFARYGLDKV     180
QMTSMDYKKR QVNLYFSELS AQTLEAESVL ALVRELGLHV PNELGLKFCK RSFSVYPTLN     240
WETGKIDRLC FAVISNDPTL VPSSDEGDIE KFHNYATKAP YAYVGEKRTL VYGLTLSPKE     300
EYYKLSANYH ITDVQRGLLK AFDSLED                                        327

SEQ ID NO: 11         moltype = AA   length = 327
FEATURE               Location/Qualifiers
source                1..327
                      mol_type = protein
                      organism = synthetic construct
SEQUENCE: 11
MGSSHHHHHH SSGLVPRGSH MSEAADVERV YAAMEEAAGL LGVACARDKI YPLLSTFQDT      60
LVEGGSVVGF SMASGRHSTE LDFSISVPTS HGDPYATVVE KGLFPATGHP VDDLLADTQK     120
HLPVSMFAID GEVTGGFKKT YAFFPTDNMP GVAELSAIPS MPPAVAENAE LFARYGLDKV     180
QMTSMDYKKR QVNLYFSELS AQTLEAESVL ALVRELGLHV PNELGLKFCK RSNSVYPTLN     240
WETGKIDRLC FAVISNDPTL VPSSDEGDIE KFHNYATKAP YAYVGEKRTL VYGLTLSPKE     300
EYYKLGANYH ITDVQRGLLK AFDSLED                                        327

SEQ ID NO: 12         moltype = AA   length = 327
FEATURE               Location/Qualifiers
source                1..327
                      mol_type = protein
                      organism = synthetic construct
SEQUENCE: 12
MGSSHHHHHH SSGLVPRGSH MSEAADVERV YAAMEEAAGL LGVACARDKI YPLLSTFQDT      60
LVEGGSVVVF SMASGRHSTE LDFSISVPTS HGDPYATVVE KGLFPATGHP VDDLLADTQK     120
HLPVSMFAID GEVTGGFKKT YAFFPTDNMP GVAELSAIPS MPPAVAENAE LFARYGLDKV     180
QMTSMDYKKR QVNLYFSELS AQTLEAESVL ALVRELGLHV PNELGLKFCK RSNSVYPTLN     240
WETGKIDRLC FAVTSNDPTL VPSSDEGDIE KFHNYATKAP YAYVGEKRTL VYGLTLSPKE     300
EYYKLGAAYH ITDVQRGLLK AFDSLED                                        327

SEQ ID NO: 13         moltype = AA   length = 327
FEATURE               Location/Qualifiers
source                1..327
                      mol_type = protein
                      organism = synthetic construct
SEQUENCE: 13
MGSSHHHHHH SSGLVPRGSH MSEAADVERV YAAMEEAAGL LGVACARDKI YPLLSTFQDT      60
LVEGGSVVNF SMASGRHSTE LDFSISVPTS HGDPYATVVE KGLFPATGHP VDDLLADTQK     120
HLPVSMFAID GEVTGGFKKT YAFFPTDNMP GVAELSAIPS MPPAVAENAE LFARYGLDKV     180
QMTSMDYKKR QVNLYFSELS AQTLEAESVL ALVRELGLHV PNELGLKFCK RSNSVYPTLN     240
WETGKIDRLC FAVISNDPTL VPSSDEGDIE KFHNYATKAP YAYVGEKRTL VYGLTLSPKE     300
EYYKLGASYH ITDVQRGLLK AFDSLED                                        327

SEQ ID NO: 14         moltype = AA   length = 327
FEATURE               Location/Qualifiers
source                1..327
                      mol_type = protein
                      organism = synthetic construct
SEQUENCE: 14
MGSSHHHHHH SSGLVPRGSH MSEAADVERV YAAMEEAAGL LGVACARDKI YPLLSTFQDT      60
LVEGGSVVVF SMASGRHSTE LDFSISVPTS HGDPYATVVE KGLFPATGHP VDDLLADTQK     120
HLPVSMFAID GEVTGGFKKT YAFFPTDNMP GVAELSAIPS MPPAVAENAE LFARYGLDKV     180
QMTSMDYKKR QVNLYFSELS AQTLEAESVL ALVRELGLHV PNELGLKFCK RSGSVYPTLN     240
WETGKIDRLC FAVTSNDPTL VPSSDEGDIE KFHNYATKAP YAYVGEKRTL VYGLTLSPKE     300
EYYKLGANYH ITDVQRGLLK AFDSLED                                        327

SEQ ID NO: 15         moltype = AA   length = 327
FEATURE               Location/Qualifiers
source                1..327
                      mol_type = protein
```

```
                    organism = synthetic construct
SEQUENCE: 15
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSNSVYPTLN   240
WETGKIDRLC FSVISNDPTL VPSSDEGDIE KFHNYATKAP YAYVGEKRTL VYGLTLSPKE   300
EYYKLGAAYH ITDVQRGLLK AFDSLED                                      327

SEQ ID NO: 16            moltype = AA    length = 327
FEATURE                  Location/Qualifiers
source                   1..327
                         mol_type = protein
                         organism = synthetic construct
SEQUENCE: 16
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSNSVYPTLN   240
WETGKIDRLC FSVISNDPTL VPSSDEGDIE KFHNYATKAP YAYVGEKRTL VYGLTLSPKE   300
EYYKLGANYH ITDVQRGLLK AFDSLED                                      327

SEQ ID NO: 17            moltype = AA    length = 327
FEATURE                  Location/Qualifiers
source                   1..327
                         mol_type = protein
                         organism = synthetic construct
SEQUENCE: 17
MGSSHHHHHH SSGLVPRGSH MSEAADVERV YAAMEEAAGL LGVACARDKI YPLLSTFQDT    60
LVEGGSVVTF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSGSVYPTLN   240
WETGKIDRLC FAVISNDPTL VPSSDEGDIE KFHNYATKAP YAYVGEKRTL VYGLTLSPKE   300
EYYKLGANYH ITDVQRGLLK AFDSLED                                      327

SEQ ID NO: 18            moltype = AA    length = 327
FEATURE                  Location/Qualifiers
source                   1..327
                         mol_type = protein
                         organism = synthetic construct
SEQUENCE: 18
MGSSHHHHHH SSGLVPRGSH MSEAADVERV YAAMEEAAGL LGVACARDKI YPLLSTFQDT    60
LVEGGSVVSF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FAVISNDPTL VPSSDEGDIE KFHNYATKAP YAYVGEKRTL NYGLTLSPKE   300
EYYKLGANYH ITDVQRGLLK AFDSLED                                      327

SEQ ID NO: 19            moltype = AA    length = 327
FEATURE                  Location/Qualifiers
source                   1..327
                         mol_type = protein
                         organism = synthetic construct
SEQUENCE: 19
MGSSHHHHHH SSGLVPRGSH MSEAADVERV YAAMEEAAGL LGVACARDKI YPLLSTFQDT    60
LVEGGSVVSF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSNSVYPTLN   240
WETGKIDRLC FAVISNDPTL VPSSDEGDIE KFHNYATKAP YAYVGEKRTL NYGLTLSPKE   300
EYYKLGANYH ITDVQRGLLK AFDSLED                                      327

SEQ ID NO: 20            moltype = AA    length = 327
FEATURE                  Location/Qualifiers
source                   1..327
                         mol_type = protein
                         organism = synthetic construct
SEQUENCE: 20
MGSSHHHHHH SSGLVPRGSH MSEAADVERV YAAMEEAAGL LGVACARDKI YPLLSTFQDT    60
LVEGGSVVTF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSGSVYPTLN   240
WETGKIDRLC FAVISNDPTL VPSSDEGDIE KFHNYATKAP YAYVGEKRTL HYGLTLSPKE   300
EYYKLGANYH ITDVQRGLLK AFDSLED                                      327

SEQ ID NO: 21            moltype = AA    length = 327
FEATURE                  Location/Qualifiers
source                   1..327
                         mol_type = protein
                         organism = synthetic construct
```

```
SEQUENCE: 21
MGSSHHHHHH SSGLVPRGSH MSEAADVERV YAAMEEAAGL LGVACARDKI YPLLSTFQDT   60
LVEGGSVVSF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSNSVYPTLN  240
WETGKIDRLC FSVTSNDPTL VPSSDEGDIE KFHNYATKAP YAYVGEKRTL NYGLTLSPKE  300
EYYKLGANYH ITDVQRGLLK AFDSLED                                     327

SEQ ID NO: 22            moltype = AA   length = 327
FEATURE                  Location/Qualifiers
source                   1..327
                         mol_type = protein
                         organism = synthetic construct
SEQUENCE: 22
MGSSHHHHHH SSGLVPRGSH MSEAADVERV YAAMEEAAGL LGVACARDKI YPLLSTFQDT   60
LVEGGSVVTF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSGSVYPTLN  240
WETGKIDRLC FAVTSNDPTL VPSSDEGDIE KFHNYATKAP YAYVGEKRTL HYGLTLSPKE  300
EYYKLGANYH ITDVQRGILK AFDSLED                                     327

SEQ ID NO: 23            moltype = AA   length = 327
FEATURE                  Location/Qualifiers
source                   1..327
                         mol_type = protein
                         organism = synthetic construct
SEQUENCE: 23
MGSSHHHHHH SSGLVPRGSH MSEAADVERV YAAMEEAAGL LGVACARDKI YPLLSTFQDT   60
LVEGGSVVVF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSFSVYPTLN  240
WETGKIDRLC FAVISNDPTL VPSSDEGDIE KFHNYATKAP YAYVGEKRTL VYGLTLSPKE  300
EYYKLSAAYH ITDVQRGLLK AFDSLED                                     327

SEQ ID NO: 24            moltype = AA   length = 327
FEATURE                  Location/Qualifiers
source                   1..327
                         mol_type = protein
                         organism = synthetic construct
SEQUENCE: 24
MGSSHHHHHH SSGLVPRGSH MSEAADVERV YAAMEEAAGL LGVACARDKI YPLLSTFQDT   60
LVEGGSVVVF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSFSVYPTLN  240
WETGKIDRLC FSVISNDPTL VPSSDEGDIE KFHNYATKAP YAYVGEKRTL VYGLTLSPKE  300
EYYKLSAAYH ITDVQRGLLK AFDSLED                                     327

SEQ ID NO: 25            moltype = AA   length = 327
FEATURE                  Location/Qualifiers
source                   1..327
                         mol_type = protein
                         organism = synthetic construct
SEQUENCE: 25
MGSSHHHHHH SSGLVPRGSH MSEAADVERV YAAMEEAAGL LGVACARDKI YPLLSTFQDT   60
LVEGGSVVVF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSHSVYPTLN  240
WETGKIDRLC FSVISNDPTL VPSSDEGDIE KFHNYATKAP YAYVGEKRTL VYGLTLSPKE  300
EYYKLSAAYH ITDVQRGLLK AFDSLED                                     327

SEQ ID NO: 26            moltype = AA   length = 327
FEATURE                  Location/Qualifiers
source                   1..327
                         mol_type = protein
                         organism = synthetic construct
SEQUENCE: 26
MGSSHHHHHH SSGLVPRGSH MSEAADVERV YAAMEEAAGL LGVACARDKI YPLLSTFQDT   60
LVEGGSVVVF SMASGRHSTE LDFSISVPTS HGDPYATVVE KGLFPATGHP VDDLLADTQK  120
HLPVSMFAID GEVTGGFKKT YAFFPTDNMP GVAELSAIPS MPPAVAENAE LFARYGLDKV  180
QMTSMDYKKR QVNLYFSELS AQTLEAESVL ALVRELGLHV PNELGLKFCK RSFSVYPTLN  240
WETGKIDRLC FAVISNDPTL VPSSDEGDIE KFHNYATKAP YAYVGEKRTL VYGLTLSPKE  300
EYYKLSAVYH ITDVQRGLLK AFDSLED                                     327

SEQ ID NO: 27            moltype = AA   length = 327
FEATURE                  Location/Qualifiers
source                   1..327
                         mol_type = protein
SEQUENCE: 27
```

```
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FSVISNDPTL VPSSDEGDIE KFHNYATKAP YAYVGEKRTL VYGLTLSPKE   300
EYYKLSAVYH ITDVQRGLLK AFDSLED                                      327

SEQ ID NO: 28          moltype = AA  length = 328
FEATURE                Location/Qualifiers
source                 1..328
                       mol_type = protein
                       organism = synthetic construct
SEQUENCE: 28
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FSAVISNDPT LVPSSDEGDI EKFHNYATKA PYAYVGEKRT LVYGLTLSPK   300
EEYYKLGAAY HITDVQRGLL KAFDSLED                                     328

SEQ ID NO: 29          moltype = AA  length = 328
FEATURE                Location/Qualifiers
source                 1..328
                       mol_type = protein
                       organism = synthetic construct
SEQUENCE: 29
MGSSHHHHHH SSGLVPRGSH MSEAADVERV YAAMEEAAGL LGVACARDKI YPLLSTFQDT    60
LVEGGSVVVF SMASGRHSTE LDFSISVPTS HGDPYATVVE KGLFPATGHP VDDLLADTQK   120
HLPVSMFAID GEVTGGFKKT YAFFPTDNMP GVAELSAIPS MPPAVAENAE LFARYGLDKV   180
QMTSMDYKKR QVNLYFSELS AQTLEAESVL ALVRELGLHV PNELGLKFCK RSFSVYPTLN   240
WETGKIDRLC FSAVISNDPT LVPSSDEGDI EKFHNYATKA PYAYVGEKRT LVYGLTLSPK   300
EEYYKLGAVY HITDVQRGLL KAFDSLED                                     328

SEQ ID NO: 30          moltype = AA  length = 307
FEATURE                Location/Qualifiers
source                 1..307
                       mol_type = protein
                       organism = Streptomyces sp.
SEQUENCE: 30
MSEAADVERV YAAMEEAAGL LGVACARDKI YPLLSTFQDT LVEGGSVVVF SMASGRHSTE    60
LDFSISVPTS HGDPYATVVE KGLFPATGHP VDDLLADTQK HLPVSMFAID GEVTGGFKKT   120
YAFFPTDNMP GVAELSAIPS MPPAVAENAE LFARYGLDKV QMTSMDYKKR QVNLYFSELS   180
AQTLEAESVL ALVRELGLHV PNELGLKFCK RSFSVYPTLN WETGKIDRLC FAVISNDPTL   240
VPSSDEGDIE KFHNYATKAP YAYVGEKRTL VYGLTLSPKE EYYKLGAYYH ITDVQRGLLK   300
AFDSLED                                                            307

SEQ ID NO: 31          moltype = AA  length = 449
FEATURE                Location/Qualifiers
source                 1..449
                       mol_type = protein
                       organism = Geobacillus thermodenitrificans
SEQUENCE: 31
MTHIRFDYSK ALAFFGEHEL TYLRDAVKVA HHSLHEKTGV GNDFLGWLDW PVNYDKEEFA    60
RIKQAAKKIQ SDSDVLLVIG IGGSYLGARA AIEMLHHSFY NALPKEKRST PQIIFVGNNI   120
SSTYMKDVID FLEGKDFSIN VISKSGTTTE PAIAFRIFRK LLEDKYGKEE ARRRIYATTD   180
RARGALRTLA DEEGYETFVI PDDIGGRYSV LTAVGLLPIA ASGADIDAMM EGAAKAREDF   240
SRSELEENAA YQYAAIRNIL YNKGKTIELL VNYEPALHYF AEWWKQLFGE SEGKDQKGIY   300
PASADFSTDL HSLGQYIQEG RRDLFETVLK LEEPRHELVI EAEESDLDGL NYLAGQTVDF   360
VNTKAFEGTL LAHTDGGVPN LVVTLPKLDE YTFGYLVYFF EKACAMSGYL LGVNPFDQPG   420
VEAYKKNMFA LLGKPGYEEL KDELEKRLK                                    449

SEQ ID NO: 32          moltype = AA  length = 319
FEATURE                Location/Qualifiers
source                 1..319
                       mol_type = protein
                       organism = Geobacillus stearothermophilus
SEQUENCE: 32
MKRIGVLTSG GDSPGMNAAI RSVVRKAIYH GVEVYGVYHG YAGLIAGNIK KLEVGDVGDI    60
IHRGGTILYT ARCPEFKTEE GQKKGIEQLK KHGIEGLVVI GGDGSYQGAK KLTEHGFPCV   120
GVPGTIDNDI PGTDFTIGFD TALNTVIDAI DKIRDTATSH ERTYVIEVMG RHAGDIALWS   180
GLAGGAETIL IPEADYDMND VIARLKRGHE RGKKHSIIIV AEGVGSGVDF GRQIQEATGF   240
ETRVTVLGHV QRGGSPTAFD RVLASRLGAR AVELLLEGKG GRCVGIQNNQ LVDHDIAEAL   300
ANKHTIDQRM YALSKELSI                                               319

SEQ ID NO: 33          moltype = AA  length = 309
FEATURE                Location/Qualifiers
source                 1..309
                       mol_type = protein
                       organism = Escherichia coli
```

```
SEQUENCE: 33
MVRIYTLTLA PSLDSATITP QIYPEGKLRC TAPVFEPGGG GINVARAIAH LGGSATAIFP    60
AGGATGEHLV SLLADENVPV ATVEAKDWTR QNLHVHVEAS GEQYRFVMPG AALNEDEFRQ   120
LEEQVLEIES GAILVISGSL PPGVKLEKLT QLISAAQKQG IRCIVDSSGE ALSAALAIGN   180
IELVKPNQKE LSALVNRELT QPDDVRKAAQ EIVNSGKAKR VVVSLGPQGA LGVDSENCIQ   240
VVPPPVKSQS TVGAGDSMVG AMTLKLAENA SLEEMVRFGA AAGSAATLNQ GTRLCSHDDT   300
QKIYAYLSR                                                           309

SEQ ID NO: 34           moltype = AA   length = 319
FEATURE                 Location/Qualifiers
source                  1..319
                        mol_type = protein
                        organism = Geobacillus stearothermophilus
SEQUENCE: 34
MKRIGVLTSG GDSPGMNAAI RSVVRKAIYH GVEVYGVYHG YAGLIAGNIK KLEVGDVGDI    60
IHRGGTILYT ARCPEFKTEE GQKKGIEQLK KHGIEGLVVI GGDGSYQGAK KLTEHGFPCV   120
GVPGTIDNDI PGTDFTIGFD TALNTVIDAI DKIRDTATSH ERTYVIEVMG RHAGDIALWS   180
GLAGGAETIL IPEADYDMND VIARLKRGHE AGKKHSIIIV AEGVGSGVDF GRQIQEATGF   240
ETRVTVLGHV QRGGSPTAFD RVLASRLGAR AVELLLEGKG GRCVGIQNNQ LVDHDIAEAL   300
ANKHTIDQRM YALSKELSI                                                319

SEQ ID NO: 35           moltype = AA   length = 359
FEATURE                 Location/Qualifiers
source                  1..359
                        mol_type = protein
                        organism = Escherichia coli
SEQUENCE: 35
MSKIFDFVKP GVITGDDVQK VFQVAKENNF ALPAVNCVGT DSINAVLETA AKVKAPVIVQ    60
FSNGGASFIA GKGVKSDVPQ GAAILGAISG AHHVHQMAEH YGVPVILHTD HCAKKLLPWI   120
DGLLDAGEKH FAATGKPLFS SHMIDLSEES LQENIEICSK YLERMSKIGM TLEIELGCTG   180
GEEDGVDNSH MDASALYTQP EDVDYAYTEL SKISPRFTIA ASFGNVHGVY KPGNVVLTPT   240
ILRDSQEYVS KKHNLPHNSL NFVPHGGSGS TAQEIKDSVS YGVVKMNIDT DTQWATWEGV   300
LNYYKANEAY LQGQLGNPKG EDQPNKKYYD PRVWLRAGQT SMIARLEKAF QELNAIDVL   359

SEQ ID NO: 36           moltype = AA   length = 255
FEATURE                 Location/Qualifiers
source                  1..255
                        mol_type = protein
                        organism = Escherichia coli
SEQUENCE: 36
MRHPLVMGNW KLNGSRHMVH ELVSNLRKEL AGVAGCAVAI APPEMYIDMA KREAEGSHIM    60
LGAQNVDLNL SGAFTGETSA AMLKDIGAQY IIIGHSERRT YHKESDELIA KKFAVLKEQG   120
LTPVLCIGET EAENEAGKTE EVCARQIDAV LKTQGAAAFE GAVIAYEPVW AIGTGKSATP   180
AQAQAVHKFI RDHIAKVDAN IAEQVIIQYG GSVNASNAAE LFAQPDIDGA LVGGASLKAD   240
AFAVIVKAAE AAKQA                                                    255

SEQ ID NO: 37           moltype = AA   length = 335
FEATURE                 Location/Qualifiers
source                  1..335
                        mol_type = protein
                        organism = Geobacillus stearothermophilus
SEQUENCE: 37
MAVKVGINGF GRIGRNVFRA ALKNPDIEVV AVNDLTDANT LAHLLKYDSV HGRLDAEVSV    60
NGNNLVVNGK EIIVKAERDP ENLAWGEIGV DIVVESTGRF TKREDAAKHL EAGAKKVIIS   120
APAKNEDITI VMGVNQDKYD PKAHHVISNA SCTTNCLAPF AKVLHEQFGI VRGMMTTVHS   180
YTNDQRILDL PHKDLRRARA AAESIIPTTT GAAKAVALVL PELKGKLNGM AMRVPTPNVS   240
VVDLVAELEK EVTVEEVNAA LKAAAEGELK GILAYSEEPL VSRDYNGSTV SSTIDALSTM   300
VIDGKMVKVV SWYDNETGYS HRVVDLAAYI ASKGL                              335

SEQ ID NO: 38           moltype = AA   length = 335
FEATURE                 Location/Qualifiers
source                  1..335
                        mol_type = protein
                        organism = synthetic construct
SEQUENCE: 38
MAVKVGINGF GRIGRNVFRA ALKNPDIEVV AVNDLTDANT LAHLLKYDSV HGRLDAEVSV    60
NGNNLVVNGK EIIVKAERDP ENLAWGEIGV DIVVESTGRF TKREDAAKHL EAGAKKVIIS   120
APAKNEDITI VMGVNQDKYD PKAHHVISNA SCTTNCLAPF AKVLHEQFGI VRGMMTTVHS   180
YTNDQRILDL DHKDLRRARA AAESIIPTTT GAAKAVALVL PELKGKLNGM AMRVPTPNVS   240
VVDLVAELEK EVTVEEVNAA LKAAAEGELK GILAYSEEPL VSRDYNGSTV SSTIDALSTM   300
VIDGKMVKVV SWYDNETGYS HRVVDLAAYI ASKGL                              335

SEQ ID NO: 39           moltype = AA   length = 335
FEATURE                 Location/Qualifiers
source                  1..335
                        mol_type = protein
                        organism = synthetic construct
SEQUENCE: 39
MAVKVGINGF GRIGRNVFRA ALKNPDIEVV AVNARKDANT LAHLLKYDSV HGRLDAEVSV    60
```

```
NGNNLVVNGK EIIVKAERDP ENLAWGEIGV DIVVESTGRF TKREDAAKHL EAGAKKVIIS  120
APAKNEDITI VMGVNQDKYD PKAHHVISNA SCTTNCLAPF AKVLHEQFGI VRGMMTTVHS  180
YTNDQRILDL PHKDLRRARA AAESIIPTTT GAAKAVALVL PELKGKLNGM AMRVPTPNVS  240
VVDLVAELEK EVTVEEVNAA LKAAAEGELK GILAYSEEPL VSRDYNGSTV SSTIDALSTM  300
VIDGKMVKVV SWYDNETGYS HRVVDLAAYI ASKGL                            335

SEQ ID NO: 40           moltype = AA   length = 394
FEATURE                 Location/Qualifiers
source                  1..394
                        mol_type = protein
                        organism = Geobacillus stearothermophilus
SEQUENCE: 40
MNKKTIRDVD VRGKRVFCRV DFNVPMEQGA ITDDTRIRAA LPTIRYLIEH GAKVILASHL  60
GRPKGKVVEE LRLDAVAKRL GELLERPVAK TNEAVGDEVK AAVDRLNEGD VLLLENVRFY  120
PGEEKNDPEL AKAFAELADL YVNDAFGAAH RAHASTEGIA HYLPAVAGFL MEKELEVLGK  180
ALSNPDRPFT AIIGGAKVKD KIGVIDNLLE KVDNLIIGGG LAYTFVKALG HDVGKSLLEE  240
DKIELAKSFM EKAKEKGVRF YMPVDVVVAD RFANDANTKV VPIDAIPADW SALDIGPKTR  300
ELYRDVIRES KLVVWNGPMG VFEMDAFAHG TKAIAEALAE ALDTYSVIGG GDSAAAVEKF  360
GLADKMDHIS TGGGASLEFM EGKQLPGVVA LEDK                             394

SEQ ID NO: 41           moltype = AA   length = 470
FEATURE                 Location/Qualifiers
source                  1..470
                        mol_type = protein
                        organism = Geobacillus thermodenitrificans
SEQUENCE: 41
MAKQQIGVIG LAVMGKNLAL NIESRGYSVA VYNRSREKTD EFLEEAKGKN IVGTYSIEEF  60
VNALEKPRKI LLMVKAGAPT DATIEQLKPY LEKGDILIDG GNTYFKDTQR RNEELAKLGI  120
HFIGTGVSGG EEGALKGPSI MPGGQKEAHE LVRPIFEAIA AKVDGEPCTT YIGPDGAGHY  180
VKMVHNGIEY GDMQLIAEAY FLLKHVLGMD AAELHEVFAD WNKGELNSYL IEITADIFTK  240
IDDETGKPLV DVILDKAGQK GTGKWTSQNA LDLGVPLPII TESVFARFIS AMKDERVKAS  300
KLLSGPAVKP FEGDRDHFIE AVRRALYMSK ICSYAQGFAQ MKAASDEYNW NLRYGDIAMI  360
FRGGCIIRAQ FLQKIKEAYD RDPALPNLLL DPYFKNIVES YQDSLREIVA TAAMRGIPVP  420
AFASALAYYD SYRNEVLPAN LIQAQRDYFG AHTYERVDKE GIFHTEWLAK             470

SEQ ID NO: 42           moltype = AA   length = 437
FEATURE                 Location/Qualifiers
source                  1..437
                        mol_type = protein
                        organism = Escherichia coli
SEQUENCE: 42
MSKIVKIIGR EIIDSRGNPT VEAEVHLEGG FVGMAAAPSG ASTGSREALE LRDGDKSRFL  60
GKGVTKAVAA VNGPIAQALI GKDAKDQAGI DKIMIDLDGT EKKSKFGANA ILAVSLANAK  120
AAAAAKGMPL YEHIAELNGT PGKYSMPVPM MNIINGGEHA DNNVDIQEFM IQPVGAKTVK  180
EAIRMGSEVF HHLAKVLKAK GMNTAVGDEG GYAPNLGSND EALAVIAEAV KAAGYELGKD  240
ITLAMDCAAS EFYKDGKYVL AGEGNKAFTS EEFTHFLEEL TKQYPIVSIE DGLDESDWDG  300
FAYQTKVLGD KIQLVGDDLF VTNTKILKEG IEKGIANSYL IKFNQIGSLT ETLAAIKMAK  360
DAGYTAVISH RSGETEDATI ADLAVGTAAG QIKTGSMSRS DRVAKYNQLI RIEEALGEKA  420
RTTVVKRSKA RHKTDFI                                                437

SEQ ID NO: 43           moltype = AA   length = 587
FEATURE                 Location/Qualifiers
source                  1..587
                        mol_type = protein
                        organism = Geobacillus stearothermophilus
SEQUENCE: 43
MKRKTKIVCT IGPASESVDK LVQLMEAGMN VARLNFSHGD HEEHGRRIAN IREAAKRTGR  60
TVAILLDTKG PEIRTHNMEN GAIELKEGSK LVISMSEVLG TPEKISVTYP SLIDDVSVGA  120
KILLDDGLIS LEVNAVDKQA GEIVTTVLNG GVLKNKKGVN VPGVKVNLPG ITEKDRADIL  180
FGIRQGIDFI AASFVRRASD VLEIRELLEA HDALHIQIIA KIENEEGVAN IDEILEAADG  240
LMVARGDLGV EIPAEEVPLI QKLLIKKCNM LGKPVITATQ MLDSMQRNPR PTRAEASDVA  300
NAIFDGTDAV MLSGETAAGQ YPVEAVKTMH QIALRTEQAL EHRDILSQRT KESQTTITDA  360
IGQSVAHTAL NLDVAAIVTP TVSGKTPQMV AKYRPKAPII AVTSNEAVSR LRALVWGVYT  420
KEAPHVNTTD EMLDVAVDAA VRSGLVKHGD LVVITAGVPV GETGSTNLMK VHVISDLLAK  480
GQGIGRKSAF GKAVVAKTAE EARQKMVDGG ILVTVSTDAD MMPAIEKAAA IITEEGGLTS  540
HAAVVGLSLG IPVIVGVENA TTLFKDGQEI TVDGGFGAVY RGHASVL                587

SEQ ID NO: 44           moltype = AA   length = 475
FEATURE                 Location/Qualifiers
source                  1..475
                        mol_type = protein
                        organism = Zymomonas mobilis
SEQUENCE: 44
MTEGLFPRGR KVRVVSTLGP ASSTAEQIRD RFLAGADVFR INMSHGTHDE KKVIVDNIRA  60
LEKEFNRPTT ILFDLQGPKL RVGDFKEGKV QLKEGQTFTF DQDPTLGDET RVNLPHPEIF  120
KALDKGHRLL LDDGKIVVRC VESSPTKIVT RVEVPGPLSD HKGFNVPDVV IPLAALTPKD  180
RKDLDFALKE KADVWALSFV QRVEDVIEAK ELIKGRAPLL VKLEKPAAIE NLESILAATD  240
AVMVARGDLG VECLPESVPP TQKRIVERSR QLGKPVVVAT AMLESMIKAP APTRAEVSDV  300
ANAIYEGADG IMLSAESAAG DWPHEAVNMM HRIASYVENA PGYIERVRFT PTPAEPTTVD  360
```

```
ALAENASKTA ETVGAKAIIV FTETGKTAQR VSRARPVPAPI LSLTPDAEVA RRLGLVWGAQ    420
PVQVSTVKTL DEAKKLAAET AKKYGFAKAG DKLVVVAGEP FGKAGTTNIV DVIEA          475

SEQ ID NO: 45           moltype = AA  length = 531
FEATURE                 Location/Qualifiers
source                  1..531
                        mol_type = protein
                        organism = Oryctolagus cuniculus
SEQUENCE: 45
MSKSHSEAGS AFIQTQQLHA AMADTFLEHM CRLDIDSAPI TARNTGIICT IGPASRSVET     60
LKEMIKSGMN VARMNFSHGT HEYHAETIKN VRTATESFAS DPILYRPVAV ALDTKGPEIR    120
TGLIKGSGTA EVELKKGATL KITLDNAYME KCDENILWLD YKNICKVVDV GSKVYVDDGL    180
ISLQVKQKGP DFLVTEVENG GFLGSKKGVN LPGAAVDLPA VSEKDIQDLK FGVEQDVDMV    240
FASFIRKAAD VHEVRKILGE KGKNIKIISK IENHEGVRRF DEILEASDGI MVARGDLGIE    300
IPAEKVFLAQ KMIIGRCNRA GKPVICATQM LESMIKKPRP TRAEGSDVAN AVLDGADCIM    360
LSGETAKGDY PLEAVRMQHL IAREAEAAMF HRKLFEELAR ASSHSTDLME AMAMGSVEAS    420
YKCLAAALIV LTESGRSAHQ VARYRPRAPI IAVTRNHQTA RQAHLYRGIF PVVCKDPVQE    480
AWAEDVDLRV NLAMNVGKAR GFFKKGDVVI VLTGWRPGSG FTNTMRVVPV P             531

SEQ ID NO: 46           moltype = AA  length = 592
FEATURE                 Location/Qualifiers
source                  1..592
                        mol_type = protein
                        organism = Aerococcus viridans
SEQUENCE: 46
MSDNKINIGL AVMKILESWG ADTIYGIPSG TLSSLMDAMG EEENNVKFLQ VKHEEVGAMA     60
AVMQSKFGGN LGVTVGSGGP GASHLINGLY DAAMDNIPVV AILGSRPQRE LNMDAFQELN    120
QNPMYDHIAV YNRRVAYAEQ LPKLVDEAAR MAIAKRGVAV LEVPGDFAKV EIDNDQWYSS    180
ANSLRKYEPI APAAQDIDAA VELLNNSKRP VIYAGIGTMG HGPAVQELAR KIKAPVITTG    240
KNFETFEWDF EALTGSTYRV GWKPANETIL EADTVLFAGS NPPFSEVEGT FRNVDNFIQI    300
DIDPAMLGKR HHADVAILGD AGLAIDEILN KVDAVEESAW WTANLKNIAN WREYINMLET    360
KEEGDLQFYQ VYNAINNHAD EDAIYSIDVG NSTQTSIRHL HMTPKNMWRT SPLFATMGIA    420
IPGGLGAKNT YPDRQVWNII GDGAFSMTYP DVVTNVRYNM PVINVVFSNT EYAFIKNKYE    480
DTNKNLFGVD FTDVDYAKIA EAQGAKGFTV SRIEDMDRVM AEAVAANKAG HTVVIDCKIT    540
QDRPIPVETL KLDSKLYSED EIKAYKERYE AANLVPFREY LEAEGLESKY IK            592

SEQ ID NO: 47           moltype = AA  length = 393
FEATURE                 Location/Qualifiers
source                  1..393
                        mol_type = protein
                        organism = Cupriavidus necator H16
SEQUENCE: 47
MTDVVIVSAA RTAVGKFGGS LAKIPAPELG AVVIKAALER AGVKPEQVSE VIMGQVLTAG     60
SGQNPARQAA IKAGLPAMVP AMTINKVCGS GLKAVMLAAN AIMAGDAEIV VAGGQNMSA     120
APHVLPGSRD GFRMGDAKLV DTMIVDGLWD VYNQYHMGIT AENVAKEYGI TREAQDEFAV    180
GSQNKAEAAQ KAGKFDEEIV PVLIPQRKGD PVAFKTDEFV RQGATLDSMS GLKPAFDKAG    240
TVTAANASGL NDGAAAVVVM SAAKAKELGL TPLATIKSYA NAGVDPKVMG MGPVPASKRA    300
LSRAEWTPQD LDLMEINEAF AAQALAVHQQ MGWDTSKVNV NGGAIAIGHP IGASGCRILV    360
TLLHEMKRRD AKKGLASLCI GGGMGVALAV ERK                                 393

SEQ ID NO: 48           moltype = AA  length = 383
FEATURE                 Location/Qualifiers
source                  1..383
                        mol_type = protein
                        organism = Enterococcus faecalis
SEQUENCE: 48
MTIGIDKISF FVPPYYIDMT ALAEARNVDP GKFHIGIGQD QMAVNPISQD IVTFAANAAE     60
AILTKEDKEA IDMVIVGTES SIDESKAAAV VLHRLMGIQP FARSFEIKEA CYGATAGLQL    120
AKNHVALHPD KKVLVVAADI AKYGLNSGGE PTQGAGAVAM LVASEPRILA LKEDNVMLTQ    180
DIYDFWRPTG HPYPMVDGPL SNETYIQSFA QVWDEHKKRT GLDFADYDAL AFHIPYTKMG    240
KKALLAKISD QTEAEQERIL ARYEESIIYS RRVGNLYTSS LYLGLISLLE NATTLTAGNQ    300
IGLFSYGSGA VAEFFTGELV AGYQNHLQKE THLALLDNRT ELSIAEYEAM FAETLDTDID    360
QTLEDELKYS ISAINNTVRS YRN                                             383

SEQ ID NO: 49           moltype = AA  length = 803
FEATURE                 Location/Qualifiers
source                  1..803
                        mol_type = protein
                        organism = Enterococcus faecalis
SEQUENCE: 49
MKTVVIIDAL RTPIGKYKGS LSQVSAVDLG THVTTQLLKR HSTISEEIDQ VIFGNVLQAG     60
NGQNPARQIA INSGLSHEIP AMTVNEVCGS GMKAVILAKQ LIQLGEAEVL IAGGIENMSQ    120
APKLQRFNYE TESYDAPFSS MMYDGLTDAF SGQAMGLTAE NVAEKYHVTR EEQDQFSVHS    180
QLKAAQAQAE GIFADEIAPL EVSGTLVEKD EGIRPNSSVE KLGTLKTVFK EDGTVTAGNA    240
STINDGASAL IIASQEYAEA HGLPYLAIIR DSVEVGIDPA YMGISPIKAI QKLLARNQLT    300
TEEIDLYEIN EAFAATSIVV QRELALPEEK VNIYGGGISL GHAIGATGAR LLTSLSYQLN    360
QKEKKYGVAS LCIGGGLGLA MLLERPQQKK NSRFYQMSPE ERLASLLNEG QISADTKKEF    420
ENTALSSQIA NHMIENQISE TEVPMGVGLH LTVDETDYLV PMATEEPSVI AALSNGAKIA    480
QGFKTVNQQR LMRGQIVFYD VADAESLIDE LQVRETEIFQ QAELSYPSIV KRGGGLRDLQ    540
```

```
YRAFDESFVS VDFLVDVKDA MGANIVNAML EGVAELFREW FAEQKILFSI LSNYATESVV   600
TMKTAIPVSR LSKGSNGREI AEKIVLASRY ASLDPYRAVT HNKGIMNGIE AVVLATGNDT   660
RAVSASCHAF AVKEGRYQGL TSWTLDGEQL IGEISVPLAL ATVGGATKVL PKSQAAADLL   720
AVTDAKELSR VVAAVGLAQN LAALRALVSE GIQKGHMALQ ARSLAMTVGA TGKEVEAVAQ   780
QLKRQKTMNQ DRALAILNDL RKQ                                          803

SEQ ID NO: 50         moltype = AA  length = 301
FEATURE               Location/Qualifiers
source                1..301
                      mol_type = protein
                      organism = Methanosarcina mazei Go1
SEQUENCE: 50
MVSCSAPGKI YLFGEHAVVY GETAIACAVE LRTRVRAELN DSITIQSQIG RTGLDFEKHP    60
YVSAVIEKMR KSIPINGVFL TVDSDIPVGS GLGSSAAVTI ASIGALNELF GFGLSLQEIA   120
KLGHEIEIKV QGAASPTDTY VSTFGGVVTI PERRKLKTPD CGIVIGDTGV FSSTKELVAN   180
VRQLRESYPD LIEPLMTSIG KISRIGEQLV LSGDYASIGR LMNVNQGLLD ALGVNILELS   240
QLIYSARAAG AFGAKITGAG GGGCMVALTA PEKCNQVAEA VAGAGGKVTI TKPTEQGLKV   300
D                                                                  301

SEQ ID NO: 51         moltype = AA  length = 335
FEATURE               Location/Qualifiers
source                1..335
                      mol_type = protein
                      organism = Streptococcus pneumoniae
SEQUENCE: 51
MIAVKTCGKL YWAGEYAILE PGQLALIKDI PIYMRAEIAF SDSYRIYSDM FDFAVDLRPN    60
PDYSLIQETI ALMGDFLAVR GQNLRPFSLA IYGKMEREGK KFGLGSSGSV VVLVVKALLA   120
LYNLSVDQNL LFKLTSAVLL KRGDNGSMGD LACIAAEDLV LYQSFDRQKV AAWLEEENLA   180
TVLERDWGFS ISQVKPTLEC DFLVGWTKEV AVSSHMVQQI KQNINQNFLT SSKETVVSLV   240
EALEQGKSEK IIEQVEVASK LLEGLSTDIY TPLLRQLKEA SQDLQAVAKS SGAGGGDCGI   300
ALSFDAQSTK TLKNRWADLG IELLYQERIG HDDKS                             335

SEQ ID NO: 52         moltype = AA  length = 344
FEATURE               Location/Qualifiers
source                1..344
                      mol_type = protein
                      organism = Streptococcus pneumoniae
SEQUENCE: 52
MYHSLGNQFD TRTRTSRKIR RERSCSDMDR EPVTVRSYAN IAIIKYWGKK KEKEMVPATS    60
SISLTLENMY TETTLSPLPA NVTADEFYIN GQLQNEVEHA KMSKIIDRYR PAGEGFVRID   120
TQNNMPTAAG LSSSSSGLSA LVKACNAYFK LGLDRSQLAQ EAKFASGSSS RSFYGPLGAW   180
DKDSGEIYPV ETDLKLAMIM LVLEDKKKPI SSRDGMKLCV ETSTTFDDWV RQSEKDYQDM   240
LIYLKENDFA KIGELTEKNA LAMHATTKTA SPAFSYLTDA SYEAMDFVRQ LREKGEACYF   300
TMDAGPNVKV FCQEKDLEHL SEIFGQRYRL IVSKTKDLSQ DDCC                   344

SEQ ID NO: 53         moltype = AA  length = 297
FEATURE               Location/Qualifiers
source                1..297
                      mol_type = protein
                      organism = Geobacillus stearothermophilus
SEQUENCE: 53
MAQLSVEQFL NEQKQAVETA LSRYIERLEG PAKLKKAMAY SLEAGGKRIR PLLLLSTVRA    60
LGKDPAVGLP VACAIEMIHT YSLIHDDLPS MDNDDLRRGK PTNHKVFGEA MAILAGDGLL   120
TYAFQLITEI DDERIPPSVR LRLIERLAKA AGPEGMVAGQ AADMEGEGKT LTLSELEYIH   180
RHKTGKMLQY SVHAGALIGG ADARQTRELD EFAAHLGLAF QIRDDILDIE GAEEKIGKPV   240
GSDQSNNKAT YPALLSLAGA KEKLAFHIEA AQRHLRNADV DGAALAYICE LVAARDH      297

SEQ ID NO: 54         moltype = DNA  length = 789
FEATURE               Location/Qualifiers
source                1..789
                      mol_type = other DNA
                      organism = Escherichia coli
CDS                   1..789
                      protein_id = 84
                      translation = MQVDLLGSAQSAHALHLFHQHSPLVHCMTNDVVQTFTANTLLALGA
                      SPAMVIETEEASQFAAIASALLINVGTLTQPRAQAMRAAVEQAKSSQTPWTLDPVAVGA
                      LDYRRHFCHELLSFKPAAIRGNASEIMALAGIANGGRGVDTTDAAANAIPAAQTLARET
                      GAIVVVTGEMDYVTDGHRIIGIHGGDPLMTKVVGTGCALSAVVAACCALPGDTLENVAS
                      ACHWMKQAGERAVARSEGPGSFVPHFLDALWQLTQEVQA
SEQUENCE: 54
atgcaagtcg acctgctggg ttcagcgcaa tctgcgcacg cgttacacct ttttcaccaa    60
cattcccctc ttgtgcactg catgaccaat gatgtggtgc aaacctttac cgccaatacc   120
ttgctggcgc tcggtgcatc gccagcgatg ttatcgaaa ccgaagaggc cagtcagttt   180
gcggcgatcg ccagtgcctt gttgattaac gttggcacac tgacgcagcc acgcgctcag   240
gcgatgcgtg ctgccgttga gcaagcaaaa agctctcaaa cacccctgga cgcttgatcca   300
gtagcggtgg gtgcgctcga ttatcgccgc cattttgtc atgaactttt atcttttaaa    360
ccggcagcga tacgtggtaa tgcttcggaa atcatggcat tagctggcat tgctaatggc   420
ggacggggag tggataccac tgacgccgca gctaacgcga taccgctgc acaaacactg   480
gcacgggaaa ctggcgcaat cgtcgtggtc actggcgaga tggattatgt taccgatgga   540
```

-continued

```
catcgtatca ttggtattca cggtggtgat ccgttaatga ccaaagtggt aggaactggc    600
tgtgcattat cggcggttgt cgctgcctgc tgtgcgttac caggcgatac gctgaaaaat    660
gtcgcatctg cctgtcactg gatgaaacaa gccggagaac gcgcagtcgc cagaagcgag    720
gggccaggca gttttgttcc acatttcctt gatgcgctct ggcaattgac gcaggaggtg    780
caggcatga                                                             789

SEQ ID NO: 55          moltype = AA  length = 262
FEATURE                Location/Qualifiers
source                 1..262
                       mol_type = protein
                       organism = Escherichia coli
SEQUENCE: 55
MQVDLLGSAQ SAHALHLFHQ HSPLVHCMTN DVVQTFTANT LLALGASPAM VIETEEASQF     60
AAIASALLIN VGTLTQPRAQ AMRAAVEQAK SSQTPWTLDP VAVGALDYRR HFCHELLSFK    120
PAAIRGNASE IMALAGIANG GRGVDTTDAA ANAIPAAQTL ARETGAIVVV TGEMDYVTDG    180
HRIIGIHGGD PLMTKVVGTG CALSAVVAAC CALPGDTLEN VASACHWMKQ AGERAVARSE    240
GPGSFVPHFL DALWQLTQEV QA                                             262

SEQ ID NO: 56          moltype = DNA  length = 819
FEATURE                Location/Qualifiers
source                 1..819
                       mol_type = other DNA
                       organism = Bacillus subtilis
CDS                    1..819
SEQUENCE: 56
atggatgcac aatcagcagc aaaatgtctt acgctgtcc gccggcatag cccactggtg      60
catagcataa ccaacaatgt cgtaacgaat tcacagcaa acggcctgct cgcgctcggc     120
gcatcgcccg ttatggcgta cgcaaaagaa gaggtcgccg atatggcgaa aattgcgggt    180
gcactcgttt aaatatcgg aacactgagc aaggagtcag tcgaagcgat gatcatcgcg     240
ggaaaatcag ctaatgaaca tggcgttccc gtcattcttg atcctgtcgg tgccggagca    300
acaccgttcc gcactgaatc ggcacgtgac atcattcgtg aggtcgcgcct tgctgcaatc    360
agaggaaatg cggcggaaat tgcccatacc gtcggcgtga ccgattggct gatcaaaggt    420
gttgatgcgg gtgaaggtgg aggcgacatc atccggctgg ctcagcaggc ggcacaaaag    480
ctaaacacgg tcattgcgat aactggtgaa gttgatgtca tagccgacac gtcacatgta    540
tacaccttc ataacggcca caagctgctg acaaaagtga caggcgccgg ttgcctgctg     600
acttccgtcg tcggtgcgtt tgcgctgtg aagaaaatc cattgtttgc tgctattgcg     660
gccatttctt cgtatgggt cgccgctcag cttgccgcac agcagacggc tgacaaaggc    720
cctggaagct ttcagattga attgctgaac aagctttcaa ctgttactga acaagacgtc    780
caagaatggg cgactataga aagggtgact gtctcatga                            819

SEQ ID NO: 57          moltype = AA  length = 272
FEATURE                Location/Qualifiers
source                 1..272
                       mol_type = protein
                       organism = Bacillus subtilis
SEQUENCE: 57
MDAQSAAKCL TAVRRHSPLV HSITNNVVTN FTANGLLALG ASPVMAYAKE EVADMAKIAG     60
ALVLNIGTLS KESVEAMIIA GKSANEHGVP VILDPVGAGA TPFRTESARD IIREVRLAAI    120
RGNAAEIAHT VGVTDWLIKG VDAGEGGGDI IRLAQQAAQK LNTVIAITGE VDVIADTSHV    180
YTLHNGHKLL TKVTGAGCLL TSVVGAFCAV EENPLFAAIA AISSYGVAAQ LAAQQTADKG    240
PGSFQIELLN KLSTVTEQDV QEWATIERVT VS                                   272

SEQ ID NO: 58          moltype = DNA  length = 783
FEATURE                Location/Qualifiers
source                 1..783
                       mol_type = other DNA
                       organism = Methanocaldococcus jannaschii
CDS                    1..783
                       protein_id = 85
                       translation = MLTILKLGGSILSDKNVPYSIKWDNLERIAMEIKNALDYYKNQNKE
                       IKLILVHGGGAFGHPVAKKYLKIEDGKKIFINMEKGFWEIQRAMRRFNNIIDTLQSYD
                       IPAVSIQPSSFVVFGDKLIFDTSAIKEMLKRNLVPVIHGDIVIDDKNGYRIISGDDIVP
                       YLANELKADLILYATDVDGVLIDNKPIKRIDKNNIYKILNYLSGSNSIDVTGGMKYKID
                       MIRKNKCRGFVFNGNKANNIYKALLGEVEGTEIDFSE
SEQUENCE: 58
atgttgacta ttcttaagtt ggggagggagc attctgtccg ataaaaacgt tccatatagc     60
attaagtggg ataacttaga acgtattgct atggaaatca aaaacgcgtt agattattac    120
aagaaccaaa ataaagaaat taagcttatt ctggtacatg gcggcgggc atttgggcat    180
ccagtggcca agaaaatacct gaagattgaa gacggcaaaa aaattttcat caacatgaa    240
aaaggattct gggagattca gcgtgcgatg cgccgtttta ataacatcat catcgacacg    300
cttcagagtt acgatatccc agcggtctcg attcaacctt ccagctttgt tgttttggc     360
gacaaattga tcttcgacac ctctgcgatc aaagagatgt tgaaacgcaa ccttgtaccc    420
gttatccatg gggatatcgt cattgacgat aaaaatgggt accgtattat cagcggtgac    480
gacatccatg catatttagc caatgaactg aaggcagatt taatcctttta tgcaaccgac    540
gtggacggcg tattgattga caacaagccc attaaacgca ttgataagaa taatatctac    600
aagattttga attatcttc gggtagcaat tcaattgacg tcacgggggg gatgaaatac    660
aagatcgaca tgatccgtaa aaacaaatgc cgtggtttcg tgtttaatgg caacaaggca    720
aacaacattt ataaggcgct gcttggggaa gtcgaggta ccgaaatcga cttttctgaa    780
taa                                                                   783
```

```
SEQ ID NO: 59          moltype = AA   length = 260
FEATURE                Location/Qualifiers
source                 1..260
                       mol_type = protein
                       organism = Methanocaldococcus jannaschii
SEQUENCE: 59
MLTILKLGGS ILSDKNVPYS IKWDNLERIA MEIKNALDYY KNQNKEIKLI LVHGGGAFGH   60
PVAKKYLKIE DGKKIFINME KGFWEIQRAM RRFNNIIIDT LQSYDIPAVS IQPSSFVVFG  120
DKLIFDTSAI KEMLKRNLVP VIHGDIVIDD KNGYRIISGD DIVPYLANEL KADLILYATD  180
VDGVLIDNKP IKRIDKNNIY KILNYLSGSN SIDVTGGMKY KIDMIRKNKC RGFVFNGNKA  240
NNIYKALLGE VEGTEIDFSE                                              260

SEQ ID NO: 60          moltype = DNA   length = 744
FEATURE                Location/Qualifiers
source                 1..744
                       mol_type = other DNA
                       organism = Methanothrix themoacetophila
CDS                    1..744
SEQUENCE: 60
ttaaagattt tgaaattggg cggtagcatt attacggata agagccgctt agctactgca   60
cgtctggatc aaatttcacg tatcgcacac gaaatctcag gcatcgagaa cctgattgtt  120
gttcacggag ccggttcttt tggtcacatc catgccaaaa atttcggtct tccggaacgt  180
ttctcaggag aagggttact gaaaacacat ctgtcggtct cggatttgaa tcgtatcgtc  240
gttgaagctc ttcatgatgc aggggtggac gcgctgccct tgcaccccct tatcaagtgta  300
gtccttcgtg acggacgcat ccaccatatg tctaccgagg tcattacgga aatgcttcgt  360
cgtgatgtag tgccggtatt acatggggat gttgcgatgg acctgtcaaa gggtgccggc  420
attgtaagtg gagaccagtt ggtttcgtat atggcacgta ctctgggagc tggtatggtc  480
gctatgggga ccgatgtcga cggggttatg atcgatggtc gtgtccttag ttgcattaca  540
cctaatgaca tgcactcttt ggagagtcac ttattacccg caaaaggggt agacgttgga  600
ggtggaatgc gcggtaaact ggcggaatta gtagagctgg caggcattgg aattgattcc  660
cgtatttta atgccggcgt tgctggtaat gtacgccgtg ctttgtctgg ggagtcgtta  720
ggaactttga ttactggacg ctaa                                         744

SEQ ID NO: 61          moltype = AA   length = 247
FEATURE                Location/Qualifiers
source                 1..247
                       mol_type = protein
                       organism = Methanothrix themoacetophila
SEQUENCE: 61
LKILKLGGSI ITDKSRLATA RLDQISRIAH EISGIENLIV VHGAGSFGHI HAKNFGLPER   60
FSGEGLLKTH LSVSDLNRIV VEALHDAGVD ALPLHPLSSV VLRDGRIHHM STEVITEMLR  120
RDVVPVLHGD VAMDLSKGAG IVSGDQLVSY MARTLGAGMV AMGTDVDGVM IDGRVLSCIT  180
PNDMHSLESH LLPAKGVDVT GGMRGKLAEL VELAGIGIDS RIFNAGVAGN VRRALSGESL  240
GTLITGR                                                            247

SEQ ID NO: 62          moltype = DNA   length = 543
FEATURE                Location/Qualifiers
source                 1..543
                       mol_type = other DNA
                       organism = Escherichia coli
CDS                    1..543
SEQUENCE: 62
atgcaaaccg agcatgtcat tttattggac gagcaaggag aaccaattgg aactttagaa   60
aaatacgctg cacatacagc ggacacccgc ttacatcttg cttttttctag ttggctgttt  120
aacgataagg gtcaattatt agtgacgcgc cgtgcgctga gcaaaaaagc atggccgggt  180
gtttggacga cagtgtttg cggacacccc caactgggag aatccaatga ggatgcggta  240
attgccgtt gtcgctatga attgggtgtg gagattacgc caccgacacc gatctaccct  300
gatttccgtt atcgcgctac ggatccttca gtattgttga aaatgaagt gcccagtg  360
tttgccgcgc gcacaacttc tgcgcttcaa atcaacccag acgaggtcat ggattaccaa  420
tggtgtgatc ttgctgacgt actgcacggg attgacgcga caccgtgggc ttttagtccc  480
tggatggtta tgcaagcgac aaatgaagaa gcacgtaagc gccttcaggc gtttactcag  540
taa                                                                543

SEQ ID NO: 63          moltype = AA   length = 180
FEATURE                Location/Qualifiers
source                 1..180
                       mol_type = protein
                       organism = Escherichia coli
SEQUENCE: 63
MQTEHVILLD EQGEPIGTLE KYAAHTADTR LHLAFSSWLF NDKGQLLVTR RALSKKAWPG   60
VWTNSVCGHP QLGESNEDAV IRRCRYELGV EITPPTPIYP DFRYRATDPS GIVENEVCPV  120
FAARTTSALQ INPDEVMDYQ WCDLADVLHG IDATPWAFSP WMVMQATNEE ARKRLQAFTQ  180

SEQ ID NO: 64          moltype = DNA   length = 894
FEATURE                Location/Qualifiers
source                 1..894
                       mol_type = other DNA
                       organism = Geobacillus stearothermophilus
```

| CDS | 1..894 |
|---|---|

SEQUENCE: 64

```
atggcgcagc tttcagttga acagtttctc aacgagcaaa aacaggcggt ggaaacagcg    60
ctctcccgtt atatagagcg cttagaaggg ccggcgaagc tgaaaaaggc gatggcgtac   120
tcattggacg ccggcggcaa acgaatccgt ccgttgctgc ttctgtccac cgttcgggcg   180
ctcggcaaag acccggcggt cggattgccc gtcgcctgcg cgattgaaat gatccatacg   240
tacttttttga tccatgatga tttgccgagc atggacaacg atgatttgcg gcgcggcaag   300
ccgacgaacc ataaagtgtt cggcgaggcg atggccatct ggcggggga cgggttgttg   360
acgtacgcgt ttcaattgat caccgaaatc gacgatgagc gcatccctcc ttccgtccgg   420
cttcggctca tcgaacggct ggcgaaagcg gccggtccgg aagggatggt cgccggtcag   480
gcagccgata tggaaggaga ggggaaaacg ctgacgcttt cggagctcga atacattcat   540
cggcataaaa ccgggaaaat gctgcaatac agcgtgcacg ccggcgcctt gatcggcggc   600
gctgatgccc ggcaaacgcg ggagcttgac gaattcgccg cccatctagg ccttgccttt   660
caaattcgcg atgatattct cgatattgaa ggggcagaag aaaaaatcgg caagccgcct   720
ggcagccgacc aaagcaacaa caaagcgacg tatccagcgt tgctgtcgct tgccggcgcg   780
aaggaaaagt tggcgttcca tatcgaggcg gcgcagcgcc atttacggaa cgctgacgtt   840
gacggcgccg cgctcgccta tatttgcgaa ctggtcgccg cccgcgacca ttaa          894
```

| SEQ ID NO: 65 | moltype = AA   length = 297 |
|---|---|
| FEATURE | Location/Qualifiers |
| source | 1..297 |
| | mol_type = protein |
| | organism = Geobacillus stearothermophilus |

SEQUENCE: 65

```
MAQLSVEQFL NEQKQAVETA LSRYIERLEG PAKLKKAMAY SLEAGGKRIR PLLLLSTVRA    60
LGKDPAVGLP VACAIEMIHT YFLIHDDLPS MDNDDLRRGK PTNHKVFGEA MAILAGDGLL   120
TYAFQLITEI DDERIPPSVR LRLIERLAKA AGPEGMVAGQ AADMEGEGKT LTLSELEYIH   180
RHKTGKMLQY SVHAGALIGG ADARQTRELD EFAAHLGLAF QIRDDILDIE GAEEKIGKPV   240
GSDQSNNKAT YPALLSLAGA KEKLAFHIEA AQRHLRNADV DGAALAYICE LVAARDH      297
```

| SEQ ID NO: 66 | moltype = DNA   length = 924 |
|---|---|
| FEATURE | Location/Qualifiers |
| source | 1..924 |
| | mol_type = other DNA |
| | organism = synthetic construct |

SEQUENCE: 66

```
atgtccgagg cggccgacgt ggagcgtgtt tatgctgcta tggaagaagc tgcgggtctg    60
ctgggagtgg catgtgctcg tgataagatt tatcccttc tttcaacctt ccaggataca   120
ttggttgaag gtgcagtgt ggtagtgttt agcatggcta gtggacgcca cagcacggaa   180
ctggacttta gtatttcagt acccacgtcc catggtgacc catacgcaac tgtcgtcgaa   240
aagggggctgt tccctgcaac aggccatcct gttgacgatc ttttggctga tacgcagaag   300
cacctgcctg ttttctatgtt cgccattgat ggagaagtca ccggaggttt caaaaaaact   360
tatgctttct ttccaactga taatatgcca ggtgtggccg agttgagtgc catccccagt   420
atgccaccgg cggtcgcgga aaacgccgaa ttattcgcgc gttatgggtt agataaggtg   480
cagatgacgt caatggacta caagaagcgc aggtcaatt tgtacttctc tgagttaagt   540
gcacagactt tagaagccga gtctgtcctt gcgcttgttc gtgaactggg tttgcacgtg   600
ccgaacgaac tgggtcttaa attttgcaag cgctcctttt ccgtttatcc gacactgaac   660
tgggaaacag ggaaaattga tcgtttatgt tttgcggtga tttcaaacga ccctaccttg   720
gtaccaagtt cggacgaagg ggacattgaa aaatttcaca actacgcgac gaaggcgccg   780
tacgcatacg tcgcgaaaaa gcgtacgctg gtttacgggt tgacgctgag tcccaaagag   840
gaatactata aattaagcgc agcgtaccat atcaccgatg tacaacgcgg actgctgaag   900
gcctttgata gccttgaaga ctaa                                          924
```

| SEQ ID NO: 67 | moltype = DNA   length = 924 |
|---|---|
| FEATURE | Location/Qualifiers |
| source | 1..924 |
| | mol_type = other DNA |
| | organism = synthetic construct |

SEQUENCE: 67

```
atgtccgagg cggccgacgt ggagcgtgtt tatgctgcta tggaagaagc tgcgggtctg    60
ctgggagtgg catgtgctcg tgataagatt tatcccttc tttcaacctt ccaggataca   120
ttggttgaag gtgcagtgt ggtagtgttt agcatggcta gtggacgcca cagcacggaa   180
ctggacttta gtatttcagt acccacgtcc catggtgacc catacgcaac tgtcgtcgaa   240
aagggggctgt tccctgcaac aggccatcct gttgacgatc ttttggctga tacgcagaag   300
cacctgcctg ttttctatgtt cgccattgat ggagaagtca ccggaggttt caaaaaaact   360
tatgctttct ttccaactga taatatgcca ggtgtggccg agttgagtgc catccccagt   420
atgccaccgg cggtcgcgga aaacgccgaa ttattcgcgc gttatgggtt agataaggtg   480
cagatgacgt caatggacta caagaagcgc aggtcaatt tgtacttctc tgagttaagt   540
gcacagactt tagaagccga gtctgtcctt gcgcttgttc gtgaactggg tttgcacgtg   600
ccgaacgaac tgggtcttaa attttgcaag cgctcctttt ccgtttatcc gacactgaac   660
tgggaaacag ggaaaattga tcgtttatgt tttagcgtga tttcaaacga ccctaccttg   720
gtaccaagtt cggacgaagg ggacattgaa aaatttcaca actacgcgac gaaggcgccg   780
tacgcatacg tcgcgaaaaa gcgtacgctg gtttacgggt tgacgctgag tcccaaagag   840
gaatactata aattaagcgc agtgtaccat atcaccgatg tacaacgcgg actgctgaag   900
gcctttgata gccttgaaga ctaa                                          924
```

| SEQ ID NO: 68 | moltype = DNA   length = 924 |
|---|---|
| FEATURE | Location/Qualifiers |
| source | 1..924 |

```
                        mol_type = other DNA
                        organism = synthetic construct
CDS                     1..924
SEQUENCE: 68
atgtcggaag ctgccgatgt agaacgtgtc tacgccgcca tcgaagaagc cgcaggtttg    60
ttggggtcg catgcgcacg cgataagatt tggcccttgc tgtcaacatt ccaggatacc    120
ttggttgagg gtggaagcgt agttgttttt agcatggcct cggggcgtca ctcaacggag   180
ctggacttct caatttccgt cccgcctagt catggcgatc cgtacgcgat tgtggtggaa   240
aagggcttgt tccggcaac tggacatcca gttgatgaac ttctggcgga cattcagaag    300
catcttcccg tatctatgtt tgcgattgac ggggaagtta ccgggggtt caaaaaaact    360
tatgcgttct tcccgaccga taacatgccc ggtgtcgcgg aactggcggc catcccatcg   420
atgcctcctg cagtcgctga aaatgctgaa ctgttcgcgc gttatggcct ggacaaggta   480
caaatgacct cgatggatta taaaaaacgt caagtgaacc tgtatttctc cgaactgtcg   540
gctcagacgc tggaagctga atcagtactt gctttagtcc gtgaactggg tcttcatgtc   600
ccaaacgagc tgggtctgaa attttgcaaa cgctccttct cagtataccc aacattaaac   660
tgggacacct cgaagattga ccgcctttgc ttctctgtaa tcagtacaga tccgacactt   720
gtacctagct cagacgaggg agacattgaa aaatttcaca attcgctac aaaggccccc    780
tatgcatatg ttggagaaaa gcgtacactt gtttacggct tgactttatc tcccaaagag   840
gagtattata aattgggtgc cgtttaccac attactgacg tacaacgcaa acttttgaag   900
gcgttcgaca gccttgagga ttaa                                          924

SEQ ID NO: 69           moltype = AA   length = 307
FEATURE                 Location/Qualifiers
source                  1..307
                        mol_type = protein
                        organism = synthetic construct
SEQUENCE: 69
MSEAADVERV YAAIEEAAGL LGVACARDKI WPLLSTFQDT LVEGGSVVVF SMASGRHSTE    60
LDFSISVPPS HGDPYAIVVE KGLFPATGHP VDDLLADIQK HLPVSMFAID GEVTGGFKKT   120
YAFFPTDNMP GVAELAAIPS MPPAVAENAE LFARYGLDKV QMTSMDYKKR QVNLYFSELS   180
AQTLEAESVL ALVRELGLHV PNELGLKFCK RSFSVYPTLN WDTSKIDRLC FSVISTDPTL   240
VPSSDEGDIE KFHNYATKAP YAYVGEKRTL VYGLTLSPKE EYYKLGAVYH ITDVQRKLLK   300
AFDSLED                                                             307

SEQ ID NO: 70           moltype = DNA   length = 1632
FEATURE                 Location/Qualifiers
source                  1..1632
                        mol_type = other DNA
                        organism = Cannabis sativa
CDS                     1..1632
SEQUENCE: 70
atggaaaaga gtggctacgg acgcgacggt atttaccgta gcctgcgtcc tcctttacac    60
ctgccaaaca ataacaattt gagtatggtc tcattcctgt tccgtaacag cagcagctat   120
ccacagaaac cggcgttgat cgatagcgag actaatcaaa ttttatcttt tagtcatttt   180
aaaagcaccg tgatcaaggt ctcccatggc ttccttaaac cgggggatca aaagaatgac   240
gtggttttaa tctacgcacc caattcgatc cactttcccg tatgcttcct tggcattatt   300
gcttctgggg cgatcgccac tacttcaaat ccattataca ccgtgagtga gttgtcgaaa   360
caagtaaagg actcgaaccc taaattgatt atcacagtcc ctcagttatt ggaaaaggtc   420
aagggtttca atctgccaac tatccttatc ggccctgatt ctgagcagga atcgtctagt   480
gataaagtaa tgactttcaa tgatctggtc aatctgggag aagttcgggt agcgaattc    540
cctatcgtcg acgatttcaa gcaatccgac accgccgaca tgttgtactc aagtggcaaa   600
acaggtatga gcaagggggt cgttctgacg cacaaaatt ttattgcctc atcgttgatg    660
gtaacaatgg aacaggactt ggtcggcgag atggacaatg tgttcctgtg tttccttcct   720
atgttttcacg tctttggctt agccattatt acgtatgctc agttacagcg cggtaatacc   780
tgtgattttcaa tggcccgctt tgacttggaa aagatgttaa aagtgttga aagtacaaa    840
gttaccacc tttgggtcgt acccccagtt atcttagcgt tgtcgaagaa ctcaatggtc    900
aaaaaattca atttgtcatc catcaagtat attggttcag cgctgcgcc attaggaaag    960
gatctgatga agaatgctc taaggtggtt ccttacggaa tcgtggctca aggatatggc   1020
atgacggaaa cgtgcgaat cgtatccatg gaagacatcc gcggcgggaa acgcaattca   1080
gggtcggccg gaatgttggc aagtgggga gaagctcaga tcgtgagtgt ggacacctta   1140
aaacccttc ccccgaatca attagggaa atctgggtaa aagtccaaa tatgatgcaa     1200
ggctatttca acaatcctca agcgaccaaa cttaccattg ataaaagggg ttgggttcat   1260
actggcgact tggggtattt cgacgaagac ggacacttat atgttgtaga ccgtattaag   1320
gagcttatta aatacaaggg attccaagtt gcgcctgcga aactgggga attattagtt    1380
agtcaccccg agatcttaga cgcggtagtt attcccttcc ccgatgctga ggcaggcgaa   1440
gtcccggtgg catacgttgt tcgctcgcct aacagttcgt tgaccgaaaa tgacgttaaa   1500
aaattcatcg ccggtcaggt cgcctccttt aagcgtctgc gcaaggttac ttttattaat   1560
tccgtcccca gagcgcaag tgggaagatt ctgccgcg agcttattca aaaggttcgc     1620
tctaacatgt aa                                                       1632

SEQ ID NO: 71           moltype = AA   length = 543
FEATURE                 Location/Qualifiers
source                  1..543
                        mol_type = protein
                        organism = Cannabis sativa
SEQUENCE: 71
MEKSGYGRDG IYRSLRPPLH LPNNNNLSMV SFLFRNSSSY PQKPALIDSE TNQILSFSHF    60
KSTVIKVSHG FLNLGIKKND VVLIYAPNSI HFPVCFLGII ASGAIATTSN PLYTVSELSK   120
QVKDSNPKLI ITVPQLLEKV KGFNLPTILI GPDSEQESSS DKVMTFNDLV NLGGSSGSEF   180
```

```
PIVDDFKQSD TAALLYSSGT TGMSKGVVLT HKNFIASSLM VTMEQDLVGE MDNVFLCFLP   240
MFHVFGLAII TYAQLQRGNT VISMARFDLE KMLKDVEKYK VTHLWVVPPV ILALSKNSMV   300
KKFNLSSIKY IGSGAAPLGK DLMEECSKVV PYGIVAQGYG MTETCGIVSM EDIRGGKRNS   360
GSAGMLASGV EAQIVSVDTL KPLPPNQLGE IWVKGPNMMQ GYFNNPQATK LTIDKKGWVH   420
TGDLGYFDED GHLYVVDRIK ELIKYKGFQV APAELEGLLV SHPEILDAVV IPFPDAEAGE   480
VPVAYVVRSP NSSLTENDVK KFIAGQVASF KRLRKVTFIN SVPKSASGKI LRRELIQKVR   540
SNM                                                                 543

SEQ ID NO: 72           moltype = DNA   length = 2163
FEATURE                 Location/Qualifiers
source                  1..2163
                        mol_type = other DNA
                        organism = Cannabis sativa
CDS                     1..2163
SEQUENCE: 72
atgggtaaga attacaagtc cctggactct gttgtggcct ctgacttcat agccctaggt    60
atcacctctg aagttgctga gactccat ggtagactgg ccgagatcgt gtgtaattat    120
ggcgctgcca ctccccaaac atggatcaat attgccaacc atattctgtc gcctgaccat    180
cccttctccc tgcaccagat gctcttctat ggttgctata aagactttgg acctgccct    240
cctgcttgga tacccgaccc ggagaaagta aagtccacca atctgggcgc acttttggag    300
aagcgaggaa aagagttttt gggagtcaag tataaggatc ccatttcaag cttttctcat    360
ttccaagaat tttctgtaag aaaccctgag tgtgtattga acagtact aatggatgag    420
atgaagataa gttttcaaa ggatccagaa tgtatattgc gtagagatga ttaataat    480
ccaggggta gtgaatggct tccaggaggt tatcttaact cagcaaagaa ttgcttgaat    540
gtaaatagta acaagaaatt gaatgataca atgattgtat ggcgtgatga aggaaatgat    600
gatttgcctc taaacaaatt gacacttgac caattgcaag aacgtgtttg gttagttggt    660
tatgcactg aagaaatggg tttgagaag ggttgtgcaa ttgcaattga tatgccaatg    720
catgtggatg ctgtggttat ctatctagct attgttcttg cgggatatgt agttgtttct    780
attgctgata gtttttctgc tcctgaaata tcaacaagac ttcgactatc aaaagcaaaa    840
gccattttta cacaggatca tattattcgt gggaagaagc ctcttccctt atacagtaga    900
gttgtggaag ccaagtctcc catgccatt gttattcctt gtagtggctc taatattggt    960
gcagaattgc gtgatggcga tatttcttgg gattacttc tagaaagagc aaaagagttt   1020
aaaaattgtg aatttactgc tagagaacaa ccagttgatg cctatacaaa catcctcttc   1080
tcatctggaa caacagggga gccaaaggca attccatgga ctcaagctac tccttaaaa   1140
gcagctgcag atgggtggag ccatttggac attaggaag gtgatgtcat tgtttggccc   1200
actaatcttg gttggatgat gggtcctgg ctggtctatg cttcactcct taatggggct   1260
tctattgcct tgtataatgg atcaccactt gttctggct tgccaaatt tgtgcaggat   1320
gctaaagtaa caatgctagg tgtggtccct agtattgttc gatcatgaa aagtaccaat   1380
tgtgttagtg gctatgattg gtccaccatc cgttgcttt cctcttctgg tgaagcatct   1440
aatgtagatg aataccatg gttgatgggg agagcaaact acaagccgt tatcgaaatg   1500
tgtggtggca cagaaattgg tggtgcattt tctgctggct cttcttaca agctcaatca   1560
ttatcttcat ttagttcaca atgtatgggt tgcactttat acatacttga caagaatggt   1620
tatccaatgc ctaaaaacaa accaggaatt ggtgaattga cgcttggtcc agtcatgttt   1680
ggagcatcga agactctgtt gaatggtaat caccatgatg tttatttaa gggaatgcct   1740
acattgaatg gagaggtttt aaggaggcat ggggacattt ttgagcttac atctaatggt   1800
tattatcatg cacatggtcg tgcagatgat acaatgaata ttggaggcat caagattagt   1860
tccatagaga ttgaacgagt ttgtaatgaa gttgatgaca gagttttcga gacaactgat   1920
attggagtgc cacctttggg cggtggacct gagcaattag taattttctt tgtattaaaa   1980
gattcaaatg atacaactat tgacttaaat caattgaggt tatctttcaa cttgggttta   2040
cagaagaaac taaatcctct gttcaaggtc actcgtgttg tgcctcttc atcacttccg   2100
agaacagcaa ccaacaagat catgagaagg gtttgcgcc agcaatttc tcactttgaa   2160
tga                                                               2163

SEQ ID NO: 73           moltype = AA   length = 720
FEATURE                 Location/Qualifiers
source                  1..720
                        mol_type = protein
                        organism = Cannabis sativa
SEQUENCE: 73
MGKNYKSLDS VVASDFIALG ITSEVAETLH GRLAEIVCNY GAATPQTWIN IANHILSPDL    60
PFSLHQMLFY GCYKDFGPAP PAWIPDPEKV KSTNLGALLE KRGKEFLGVK YKDPISSFSH   120
FQEFSVRNPE VYWRTVLMDE MKISFSKDPE CILRRDDINN PGGSEWLPGG YLNSAKNCLN   180
VNSNKKLNDT MIVWRDEGND DLPLNKLTLD QLRKRVWLVG YALEEMGLEK GCAIAIDMPM   240
HVDAVVIYLA IVLAGYVVS IADSFSAPEI STRLRLSKAK AIFTQDHIIR GKKRIPLYSR   300
VVEAKSPMAI VIPCSGSNIG AELRDGDISW DYFLERAKEF KNCEFTAREQ PVDAYTNILF   360
SSGTTGEPKA IPWTQATPLK AAADGWSHLD IRKGDVIVWP TNLGWMMGPW LVYASLLNGA   420
SIALYNGSPL VSGFAKFVQD AKVTMLGVVP SIVRSWKSTN CVSGYDWSTI RCFSSSGEAS   480
NVDEYLWLMG RANYKPVIEM CGGTEIGGAF SAGSFLQAQS LSSFSSQCMG CTLYILDKNG   540
YPMPKNKPGI GELALGPVMF GASKTLNGNH HHDVYFKGMP TLNGEVLRRH GDIFELTSNG   600
YYHAHGRADD TMNIGGIKIS SIEIERVCNE VDDRVFETTA IGVPPLGGGP EQLVIFFVLK   660
DSNDTTIDLN QLRLSFNLGL QKKLNPLFKV TRVVPLSSLP RTATNKIMRR VLRQQFSHFE   720

SEQ ID NO: 74           moltype = DNA   length = 1695
FEATURE                 Location/Qualifiers
source                  1..1695
                        mol_type = other DNA
                        organism = Cannabis sativa
CDS                     1..1695
SEQUENCE: 74
```

```
atggaagtac tgaaggaggt tgcgaaggaa ggtagcgcag cccgtgaagg tgtcgctatt    60
cgcgccgacc agaaatcgta cagctataag caattgatct cctccgcgca gtcgatctgc   120
tcactgttat gcggtactga acttaaagcg attcacgaag ccgggaaaca agctcgtcct   180
agcgcgtcta tcaatgggc cggggtcac ggccacttgg gaggagctcg tattggaatt    240
gttgctaagc cgtcggcaga attttgtagcc ggtgttttga gtacgtggt atctggtgga   300
gttgcggttc cccttgcact gtcttacccg gaggcggaat tactgcatgt catgaacgat   360
tcagatatca gcatgatctt gagcacggaa gaccatcaag aactgatgca aaatattgct   420
gccaagactt ccgcacagtt ttccttaatt ccatctgtgc cgtcgtcgtg ctcacaagaa   480
gtagcggtcg atcatcgtca gaccggtgac atctctaccg actctatctt gcttaaccgc   540
gagatctcta acgagaatcc cgcacttatc gtctatacgt cggggacgac aggcaagccg   600
aagggcgtcg ttcacacaca ccaatcaatt tctgcacagg ttcagacgtt agccaaggca   660
tgggagtata ctcctgccga tcaattctta cactgcttac cgctgcatca tgtgcatggg   720
ctgtttaacg cactgttcgc gccccttac gcgcgttcaa cagttgaatt tctgccgaaa    780
ttttctgtcc gcggtatttg gcaacgctgg cgcgaatcct acccaacgtc agagacgaaa   840
gccaatgact gcattacggt atttacagga gttcccacca tgtacacgcg tctgattcaa   900
ggatatgaag ctatggatcc agagttaaaa gaggcctctg catctgctgc taagcagctg   960
cgccttatga tgtgtggttc ctctgcgctg ccagttcctg tcatgcagca gtggcaaacc  1020
atcaccggcc accgtcttct ggaacgttac ggaatgacca aatttgtcat ggcaatttct  1080
aaccccttga aggtgagcg caaatccggt actgtcggaa agccgtttcc aggtgtagag   1140
gtgcgcattt tagcagagga tgaaacggc gatgatgcta ccggggtggg agagctgtgc   1200
gtacgcagtc cgtcccttt caaagagtat ggcgtttgc ccgaggtcac aaaagcctcc    1260
tttacagacg acggcttttt caaaaccggc gacgcaggca aggtcgatga ggacggttac  1320
tacgtgattc tgggccgtac tagcgcagat attatgaaag ttggaggcta taagctgtct  1380
gctctggaaa tcgagtcggt ccttctggaa caccccgactg tcgaggaatg ctgtgtcttg  1440
ggacttcccg acaaggatta tggggaagcc gtatccgcaa tcattgtacc ggcagccgag  1500
gcgaagaaga aacgcgaaga ggagtcacgc cccgccatta gtcttgagga actgttctca  1560
tgggcacagc acaaacttgc cccctacaaa ctgcccacgc gtttattcct gtgggactct  1620
ttacctcgca acgcaatggg gaaagtcaac aaaaaagagc tgaagaaaaa actgacagtt  1680
gagcaaggta tttaa                                                    1695

SEQ ID NO: 75           moltype = AA   length = 564
FEATURE                 Location/Qualifiers
source                  1..564
                        mol_type = protein
                        organism = Cannabis sativa
SEQUENCE: 75
MEVLKEVAKE GSAAREGVAI RADQKSYSYK QLISSAQSIC SLLCGTELKA IHEAGKQARP    60
SASINGAGGH GHLGGARIGI VAKPSAEFVA GVLGTWLSGG VAVPLALSYP EAELLHVMND   120
SDISMILSTE DHQELMQNIA AKTSAQFSLI PSVPSSCSQE VAVDHRQTGD ISTDSILLNR   180
EISNENPALI VYTSGTTGKP KGVVHTHQSI SAQVQTLAKA WEYTPADQFL HCLPLHHVHG   240
LFNALFAPLY ARSTVEFLPK FSVRGIWQRW RESYPTSETK ANDCITVFTG VPTMYTRLIQ   300
GYEAMDPELK EASASAAKQL RLMMCGSSAL PVPVMQQWQT ITGHRLLERY GMTEFVMAIS   360
NPLKGERKSG TVGKPFPGVE VRILAEDENG DDATGVGELC VRSPSLFKEY WRLPEVTKAS   420
FTDDGFFKTG DAGKVDEDGY YVILGRTSAD IMKVGGYKLS ALEIESVLLE HPTVEECCVL   480
GLPDKDYGEA VSAIIVPAAE AKKKREEESR PAISLEELFS WAQHKLAPYK LPTRLFLWDS   540
LPRNAMGKVN KKELKKKLTV EQGI                                          564

SEQ ID NO: 76           moltype = DNA   length = 1158
FEATURE                 Location/Qualifiers
source                  1..1158
                        mol_type = other DNA
                        organism = Cannabis sativa
CDS                     1..1158
SEQUENCE: 76
atgaatcatc tgcgtgctga aggaccagct tccgtattgg caattggaac agctaaccct    60
gagaacattc ttcttcagga tgagtttccc gactattact tccgcgtgac aaagagcgaa   120
cacatgacac agcttaaaga gaagttccgt aagatctgtg acaaaagcat gatccgcaaa   180
cgtaactgct tccttaacga ggagcatctg aagcagaatc ccgtcttgt tgaacatgag    240
atgcagacct ggatgctcg ccaggacatg ttggttgttg aggtcccta aagctgggcaa    300
gatgcgtgtg caaaagcgat taaagagtgg gggcagccta aaagcaaaat tactcatctg   360
attttcacaa gcgccagtac aaccgatatg cccggtgcgg actaccattg tgcaaaatta   420
ttgggtttat cgccttcagt aaaacgtgtt atgatgtacc agttaggatg ctacggtggt   480
ggcaccgtac ttcgtattgc gaaggacatc gccgagaaca caaaggagc ccgtgtactt    540
gctgtatgtt gtgatatcat ggcgtgcctt ttcgcggcc tcagcgagag tgaccttgag   600
ttacttgtgg ggcaggccat cttcggagac ggtgccgcag ccgtcattgt tggcgcagag   660
cccgatgaat ccgttggcga gcgcccgatc tttgagcttg taagtacagg acaaactatc   720
ttgcccaact ctgaggggac tatcggcgga catattcgtg aggcgggctt gatttttgac   780
cttcacaagg atgttccaat gcttatctcc aataatatcg aaaaatgtct tatcgaagca   840
ttcactccga ttggtatctc cgattggaat tcgattttt ggatcaccca tcctggtggg    900
aaagctattt tagacaaggt ggaggagaaa ttacatctta agtcagataa gtttgtcgac   960
agtcgccacg tgttgtcgga acatggcaac atgtcatcgt caaccgtctt gttcgttatg  1020
gacgaattac gtaaacgcag tttagaagag gtaagagta cgacggggga cgggttcgag   1080
tggggagtct tattcgggtt cggtccagga ttgacagtga aacgcgtcgt ggttcgcagt  1140
gtccccatta agtactaa                                                1158

SEQ ID NO: 77           moltype = AA   length = 385
FEATURE                 Location/Qualifiers
source                  1..385
                        mol_type = protein
```

```
                              organism   = Cannabis sativa
SEQUENCE: 77
MNHLRAEGPA   SVLAIGTANP   ENILLQDEFP   DYYFRVTKSE   HMTQLKEKFR   KICDKSMIRK      60
RNCFLNEEHL   KQNPRLVEHE   MQTLDARQDM   LVVEVPKLGK   DACAKAIKEW   GQPKSKITHL     120
IFTSASTTDM   PGADYHCAKL   LGLSPSVKRV   MMYQLGCYGG   GTVLRIAKDI   AENNKGARVL     180
AVCCDIMACL   FRGPSESDLE   LLVGQAIFGD   GAAAVIVGAE   PDESVGERPI   FELVSTGQTI     240
LPNSEGTIGG   HIREAGLIFD   LHKDVPMLIS   NNIEKCLIEA   FTPIGISDWN   SIFWITHPGG     300
KAILDKVEEK   LHLKSDKFVD   SRHVLSEHGN   MSSSTVLFVM   DELRKRSLEE   GKSTTGDGFE     360
WGVLFGFGPG   LTVERVVVRS   VPIKY                                                385

SEQ ID NO: 78             moltype = DNA   length = 306
FEATURE                   Location/Qualifiers
source                    1..306
                          mol_type = other DNA
                          organism = Cannabis sativa
CDS                       1..306
SEQUENCE: 78
atggcagtca aacacttgat cgtgttaaag ttcaaagatg aaatcacaga ggctcagaag    60
gaagaatttt tcaagacgta tgtaaacctt gttaatatca tccccgctat gaaggatgtg   120
tattggggta aagacgtgac acagaagaac aaagaggaag ctacacgca catcgtagag    180
gtcacatttg agagcgtcga aactattcag gattacatca ttcatcccgc acacgttgga   240
ttcgggggatg tgtatcgctc tttctgggaa aaattgctga tcttcgacta tacaccgcgt   300
aagtaa                                                              306

SEQ ID NO: 79             moltype = AA   length = 101
FEATURE                   Location/Qualifiers
source                    1..101
                          mol_type = protein
                          organism = Cannabis sativa
SEQUENCE: 79
MAVKHLIVLK   FKDEITEAQK   EEFFKTYVNL   VNIIPAMKDV   YWGKDVTQKN   KEEGYTHIVE      60
VTFESVETIQ   DYIIHPAHVG   FGDVYRSFWE   KLLIFDYTPR   K                          101

SEQ ID NO: 80             moltype = DNA   length = 654
FEATURE                   Location/Qualifiers
source                    1..654
                          mol_type = other DNA
                          organism = Geobacillus thermodenitrificans
CDS                       1..654
SEQUENCE: 80
atgaatttag tgctgatggg gctgccaggt gccggcaaag gcacgcaagc cgagaaaatc    60
gtagaaacat atggaatccc acatatttca accggggata tgtttcgggc ggcgatgaaa   120
gaaggcacac cgttaggatt gcaggcaaaa gaatatatcg accgtggtga tcttgttccg   180
gatgaggtga cgatcggtat cgtccgtgaa cggttaagca agacgactg ccaaaacggc    240
ttttttgcttg acggattccc acgcacggtt gcccaagcgg aggcgctgga agcgatgctg   300
gctgaaatcg gccgcaagct tgactatgtc atccatatcg atgttcgcca agatgtgtta   360
atggagcgcc tcacaggcag acgaaatttgt cgcaactgcg gagcgacata ccatcttgtt   420
tttcacccac cggctcagcc aggcgtatgt gataaatgcg gtggcgagct ttatcagcgc   480
cctgacgata tgaagcaac agtgcgaat cggcttgagg tgaatacgaa acaaatgaag     540
ccattgctgc atttctatga gcaaaaaggc tatttgcgtc acattaacgg cgaacaagaa   600
atggaaaaag tgtttagcga cattcgcgaa ttgctcgggg gacttactcg ataa          654

SEQ ID NO: 81             moltype = AA   length = 217
FEATURE                   Location/Qualifiers
source                    1..217
                          mol_type = protein
                          organism = Geobacillus thermodenitrificans
SEQUENCE: 81
MNLVLMGLPG   AGKGTQAEKI   VETYGIPHIS   TGDMFRAAMK   EGTPLGLQAK   EYIDRGDLVP      60
DEVTIGIVRE   RLSKDDCQNG   FLLDGFPRTV   AQAEALEAML   AEIGRKLDYV   IHIDVRQDVL     120
MERLTGRRIC   RNCGATYHLV   FHPPAQPGVC   DKCGGELYQR   PDDNEATVAN   RLEVNTKQMK     180
PLLDFYEQKG   YLRHINGEQE   MEKVFSDIRE   LLGGLTR                                 217

SEQ ID NO: 82             moltype = DNA   length = 1512
FEATURE                   Location/Qualifiers
source                    1..1512
                          mol_type = other DNA
                          organism = Rhodopseudomonas palustris
CDS                       1..1512
SEQUENCE: 82
atgaacgcca acctgttcgc ccgcctgttc gataagctcg acgaccccca caagctcgcg    60
atcgaaaccg cggccgggga caagatcagc tacgccgagc tggtggcgcg gcgggccgc    120
gtcgccaacg tgctggtggc acgcggcctg caggtcggcg accgcgttgc ggcgcaaacc   180
gagaagtcgg tggaagcgct ggtgctgtat ctcgccacgg ccctcgtgtat               240
ctgccgctca acaccgccta cgctgcac gagctcgatt acttcatcac cgatgccgag     300
ccgaagatcg tggtgcgcga tccgtccaag cgcgacggga tcgcggcgat tgccgccaag   360
gtcggcgcca cggtggagac gcttggcccc gacggtcggg gctcgctcac cgatgcgca    420
gctggagcca gcgaggcgtt cgccacgatc gaccgcggcg ccgatgatct ggcggcgatc   480
ctctacacct cagggacgac cggccgctcc aagggcgcga tgctcagcca cgacaatttg   540
```

```
gcgtcgaact cgctgacgct ggtcgattac tggcgcttca cgccggatga cgtgctgatc      600
cacgcgctgc cgatctatca cacccatgga ttgttcgtgg ccagcaacgt cacgctgttc      660
gcgcgcggat cgatgatctt cctgccgaag ttcgatcccg acaagatcct cgacctgatg      720
gcgcgcgcca ccgtgctgat gggtgtgccg acgttctaca cgcggctctt gcagagcccg      780
cggctgacca aggagacgac gggccacatg aggctgttca tctccgggtc ggcgccgctg      840
ctcgccgata cgcatcgcga atggtcggcg aagaccggtc acgccgtgct cgagcgctac      900
ggcatgaccg agaccaacat gaacacctcg aacccgtatg acggcgaccg cgtccccggc      960
gcggtcggcc cggcgctgcc cggcgtttcg gcgcgcgtga ccgatccgga aaccggcaag     1020
gaactgccgc gcggcgacat cggatgatc gaggtgaagg gcccgaacgt gttcaagggc      1080
tactggcgga tgccggagaa gaccaagtct gaattccgcg acgacggctt cttcatcacc     1140
ggcgacctcg gcaagatcga cgagcgcggc tacgtccaca tcctcggccg cggcaaggat     1200
ctggtgatca ccgcggctt caacgtctat ccgaaggaaa tcgagagcga gatcgacgcc      1260
atgccggcg tggtcgaatc cgcggtgatc ggcgtgccgc acgccgattt cggcgagggc      1320
gtcactgccg tggtggtgcg cgacaagggt gccacgatcg acgaagcgca ggtgctgcac     1380
ggcctcgacg gtcagctcgc caagttcaag atgccgaaga agtgatctt cgtcgacgac      1440
ctgccgcgca acaccatggg caaggtccag aagaacgtcc tgcgcgagac ctacaaggac     1500
atctacaagt aa                                                         1512

SEQ ID NO: 83          moltype = AA  length = 503
FEATURE                Location/Qualifiers
source                 1..503
                       mol_type = protein
                       organism = Rhodopseudomonas palustris
SEQUENCE: 83
MNANLFARLF DKLDDPHKLA IETAAGDKIS YAELVARAGR VANVLVARGL QVGDRVAAQT       60
EKSVEALVLY LATVRAGGVY LPLNTAYTLH ELDYFITDAE PKIVVCDPSK RDGIAAIAAK      120
VGATVETLGP DGRGSLTDAA AGASEAFATI DRGADDLAAI LYTSGTTGRS KGAMLSHDNL      180
ASNSLTLVDY WRFTPDDVLI HALPIYHTHG LFVASNVTLF ARGSMIFLPK FDPDKILDLM      240
ARATVLMGVP TFYTRLLQSP RLTKETTGHM RLFISGSAPL LADTHREWSA KTGHAVLERY      300
GMTETNMNTS NPYDGDRVPG AVGPALPGVS ARVTDPETGK ELPRGDIGMI EVKGPNVFKG      360
YWRMPEKTKS EFRDDGFFIT GDLGKIDERG YVHILGRGKD LVITGGFNVY PKEIESEIDA      420
MPGVVESAVI GVPHADFGEG VTAVVVRDKG ATIDEAQVLH GLDGQLAKFK MPKKVIFVDD      480
LPRNTMGKVQ KNVLRETYKD IYK                                             503

SEQ ID NO: 84          moltype = AA  length = 262
FEATURE                Location/Qualifiers
source                 1..262
                       mol_type = protein
                       organism = Escherichia coli
SEQUENCE: 84
MQVDLLGSAQ SAHAHLFHQ HSPLVHCMTN DVVQTFTANT LLALGASPAM VIETEEASQF       60
AAIASALLIN VGTLTQPRAQ AMRAAVEQAK SSQTPWTLDP VAVGALDYRR HFCHELLSFK      120
PAAIRGNASE IMALAGIANG GRGVDTTDAA ANAIPAAQTL ARETGAIVVV TGEMDYVTDG      180
HRIIGIHGGD PLMTKVVGTG CALSAVVAAC CALPGDTLEN VASACHWMKQ AGERAVARSE     240
GPGSFVPHFL DALWQLTQEV QA                                              262

SEQ ID NO: 85          moltype = AA  length = 260
FEATURE                Location/Qualifiers
source                 1..260
                       mol_type = protein
                       organism = Methanocaldococcus jannaschii
SEQUENCE: 85
MLTILKLGGS ILSDKNVPYS IKWDNLERIA MEIKNALDYY KNQNKEIKLI LVHGGGAFGH       60
PVAKKYLKIE DGKKIFINME KGFWEIQRAM RRFNNIIIDT LQSYDIPAVS IQPSSFVVFG      120
DKLIFDTSAI KEMLKRNLVP VIHGDIVIDD KNGYRIISGD DIVPYLANEL KADLILYATD      180
VDGVLIDNKP IKRIDKNNIY KILNYLSGSN SIDVTGGMKY KIDMIRKNKC RGFVFNGNKA      240
NNIYKALLGE VEGTEIDFSE                                                 260
```